US012390220B2

(12) United States Patent
Scott et al.

(10) Patent No.: US 12,390,220 B2
(45) Date of Patent: Aug. 19, 2025

(54) SURGICAL STAPLER CARTRIDGE HAVING RAISED SURFACE TO PROMOTE BUTTRESS ADHESION

(71) Applicant: Cilag GmbH International, Zug (CH)

(72) Inventors: Gregory G Scott, Cincinnati, OH (US); Nicholas Fanelli, Morrow, OH (US); Kevin M. Fiebig, Cincinnati, OH (US); John P. May, Mason, OH (US); Nicholas A. Wilson, Montgomery, OH (US); Devanathan Raghavan, Mason, OH (US); Jeffery D. Bruns, Cincinnati, OH (US); Pierre R. Mesnil, Newport, KY (US); Scott A. Jenkins, Mason, OH (US); Kristin L. Jambor, Cincinnati, OH (US); Cory G. Kimball, Hamilton, OH (US); Anil K. Nalagatla, Mason, OH (US); Shannon L. Jones, Cincinnati, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/588,206

(22) Filed: Feb. 27, 2024

(65) Prior Publication Data
US 2024/0382202 A1 Nov. 21, 2024

Related U.S. Application Data

(60) Provisional application No. 63/467,648, filed on May 19, 2023.

(51) Int. Cl.
*A61B 17/072* (2006.01)
(52) U.S. Cl.
CPC .. *A61B 17/07207* (2013.01); *A61B 17/07292* (2013.01); *A61B 2017/07264* (2013.01);
(Continued)

(58) Field of Classification Search
CPC ............... A61B 17/07207; A61B 17/07292
See application file for complete search history.

(56) References Cited

U.S. PATENT DOCUMENTS 8,453,914 B2 6/2013 Laurent et al.
9,186,142 B2 11/2015 Fanelli et al.
(Continued)

FOREIGN PATENT DOCUMENTS

EP 2319424 A1 5/2011

OTHER PUBLICATIONS

U.S. Appl. No. 18/588,094, entitled "Incompatible Staple Cartridge Use Prevention Features for Surgical Stapler," Filed Feb. 27, 2024.
(Continued)

*Primary Examiner* — Nathaniel C Chukwurah
(74) *Attorney, Agent, or Firm* — FROST BROWN TODD LLP

(57) ABSTRACT

A stapling assembly for a surgical instrument includes a body extending along a longitudinal axis and having an upper deck, a plurality of pockets extending through the upper deck for receiving respective staples and arranged in at least two longitudinal rows, a plurality of staple drivers, and a staple driver actuator. The stapling assembly also includes a plurality of pocket extenders extending upwardly from the upper deck. Each pocket extender has a respective top surface. The stapling assembly further includes at least one upwardly-facing surface configured to contact an adhesive of an adjunct for securing the adjunct to the stapling assembly. The at least one upwardly-facing surface is disposed at least partially between at least a portion of the upper deck and the top surfaces of the plurality of pocket extenders, and spans laterally at least partially across at least two longitudinal rows of the plurality of pockets.

20 Claims, 37 Drawing Sheets

(52) U.S. Cl.
CPC ............... *A61B 2017/07271* (2013.01); *A61B 2017/07278* (2013.01); *A61B 2017/07285* (2013.01)

(56) References Cited

U.S. PATENT DOCUMENTS

| | | | |
|---|---|---|---|
| 9,717,497 B2 | 8/2017 | Zerkle et al. | |
| 9,808,248 B2 | 11/2017 | Hoffman | |
| 9,839,421 B2 | 12/2017 | Zerkle et al. | |
| 9,861,361 B2 * | 1/2018 | Aronhalt | A61B 17/00491 |
| 10,092,292 B2 | 10/2018 | Boudreaux et al. | |
| 10,130,359 B2 | 11/2018 | Hess et al. | |
| 10,166,023 B2 | 1/2019 | Vendely et al. | |
| 10,349,939 B2 | 7/2019 | Shelton, IV et al. | |
| 10,905,418 B2 | 2/2021 | Shelton, IV et al. | |
| 11,166,724 B2 | 11/2021 | McGiveron et al. | |
| 11,229,433 B2 | 1/2022 | Schings et al. | |
| 11,298,132 B2 | 4/2022 | Shelton, IV et al. | |
| 2012/0074198 A1 | 3/2012 | Huitema et al. | |
| 2013/0214030 A1 * | 8/2013 | Aronhalt | A61B 17/07207 227/176.1 |
| 2015/0297225 A1 * | 10/2015 | Huitema | A61B 17/105 227/176.1 |
| 2015/0297229 A1 | 10/2015 | Schellin et al. | |
| 2016/0089137 A1 | 3/2016 | Hess et al. | |
| 2017/0056004 A1 | 3/2017 | Shelton, IV et al. | |
| 2022/0346854 A1 | 11/2022 | Shelton, IV et al. | |
| 2022/0387027 A1 | 12/2022 | Shelton, IV et al. | |

OTHER PUBLICATIONS

U.S. Appl. No. 18/588,147, entitled "Surgical Stapler Cartridge Having Intermediate Raised Tissue Engagement Protrusions," Filed Feb. 27, 2024.
U.S. Appl. No. 18/588,175, entitled "Surgical Stapler Cartridge Having Tissue Engagement Protrusions with Enlarged Engagement Surface," Filed Feb. 27, 2024.
U.S. Appl. No. 18/588,240, entitled "Surgical Stapler Cartridge Having Cartridge Retention Features," Filed Feb. 27, 2024.
U.S. Appl. No. 18/588,269, entitled "Surgical Stapler Anvil Having Staple Forming Pockets with Laterally Varying Orientations," Filed Feb. 27, 2024.
U.S. Appl. No. 18/588,684, entitled "Method of Surgical Stapling," Filed Feb. 27, 2024.
U.S. Appl. No. 18/588,147.
U.S. Appl. No. 18/588,175.
U.S. Appl. No. 18/588,240.
U.S. Appl. No. 18/588,269.
U.S. Appl. No. 18/588,684.
U.S. Appl. No. 18/758,887.
International Search Report and Written Opinion dated Jul. 12, 2024 for Application No. PCT/IB2024/054891, 19 pgs.

* cited by examiner

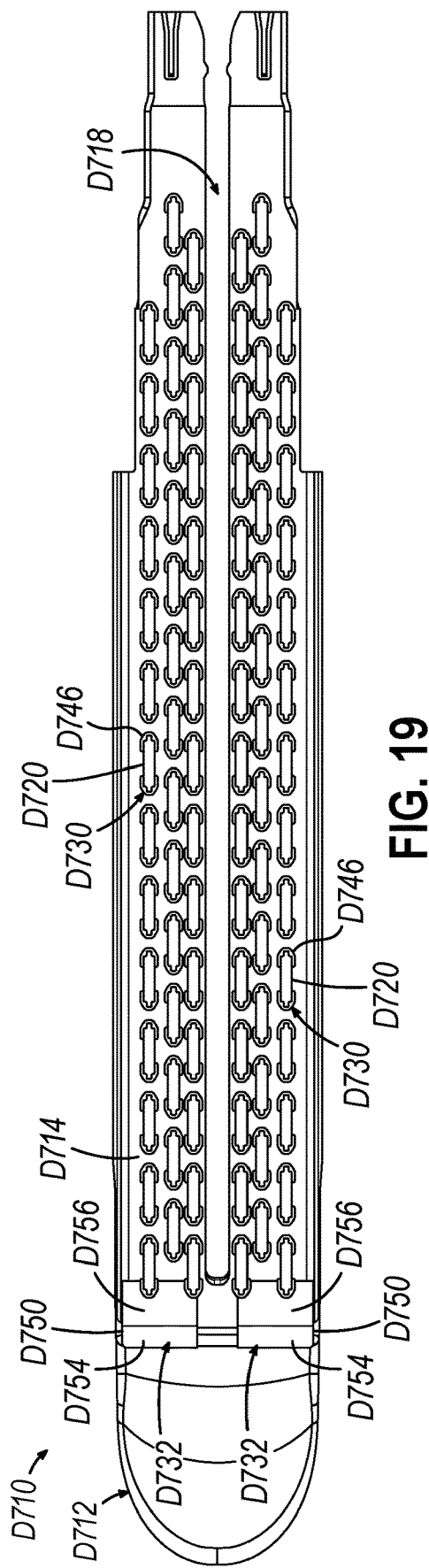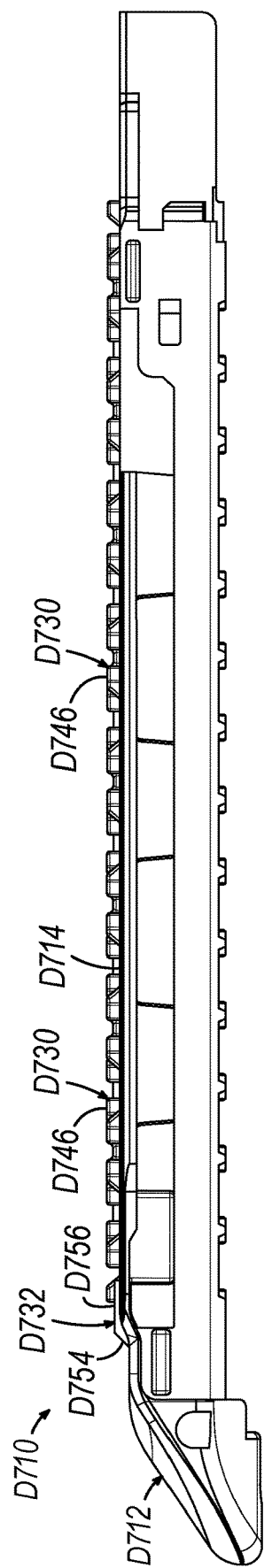
FIG. 19
FIG. 20

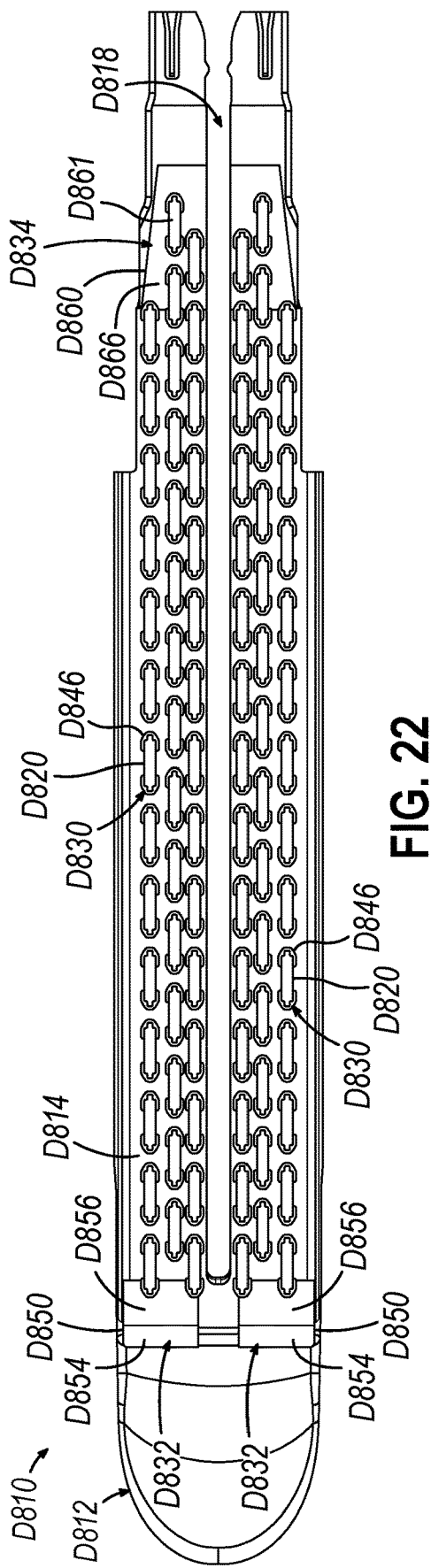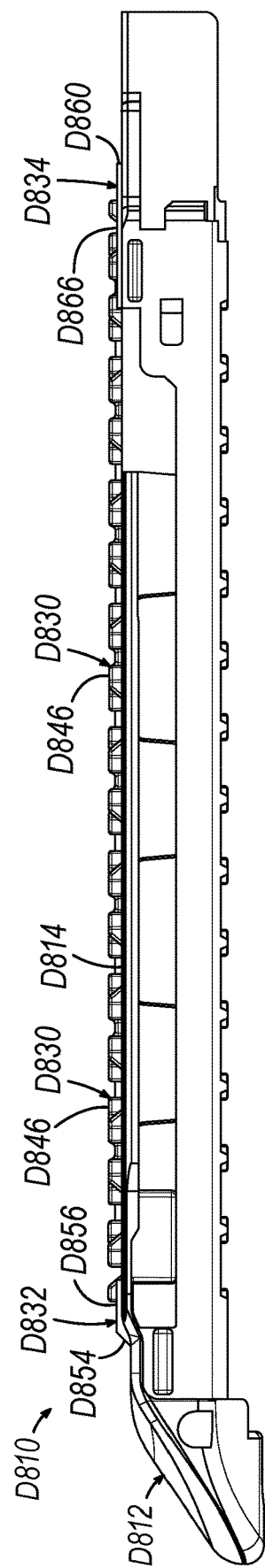
FIG. 22
FIG. 23

SURGICAL STAPLER CARTRIDGE HAVING RAISED SURFACE TO PROMOTE BUTTRESS ADHESION

PRIORITY

This application claims the benefit of U.S. Pat. App. No. 63/467,648, entitled "Surgical Stapler Cartridge Having Raised Surface to Promote Buttress Adhesion," filed May 19, 2023, the disclosure of which is incorporated by reference herein.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion or other type of body portion, which is manipulated by the clinician or robotic operator. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

The stapling assembly (e.g., cartridges) of a surgical stapler may include raised features that extend upwardly from a deck thereof for enhancing the gripping of tissue by the stapling assembly when the end effector is closed, and/or for guiding the legs of the staples as the legs exit the respective staple openings during deployment of the staples. For example, such raised features may extend upwardly from the deck at or near proximal and distal ends of each cartridge pocket and may be referred to as pocket extenders. In some instances, it may also be desirable to adhere an adjunct material, such as a buttress, to the stapling assembly for deployment with the staples to reinforce the mechanical fastening of tissue provided by the deployed staples. Typically, such adjunct material is adhered directly to the deck via an adhesive material. However, the height of the aforementioned raised gripping features may result in suboptimal adhesion of the adjunct material to the stapling assembly, such as by inhibiting the adhesive material from reaching the deck. The surgical staplers of the present disclosure seek to provide improved adhesion of buttresses and other adjunct materials to stapling assemblies having such raised gripping features.

While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate examples of the invention, and, together with the general description of the invention given above, and the detailed description of the examples given below, serve to explain the principles of the present invention.

FIG. 19 depicts a top plan view of the staple cartridge of FIG. 18;

FIG. 20 depicts a side elevational view of the staple cartridge of FIG. 18;

FIG. 22 depicts a top plan view of the staple cartridge of FIG. 21;

FIG. 23 depicts a side elevational view of the staple cartridge of FIG. 21;

Figure 1:
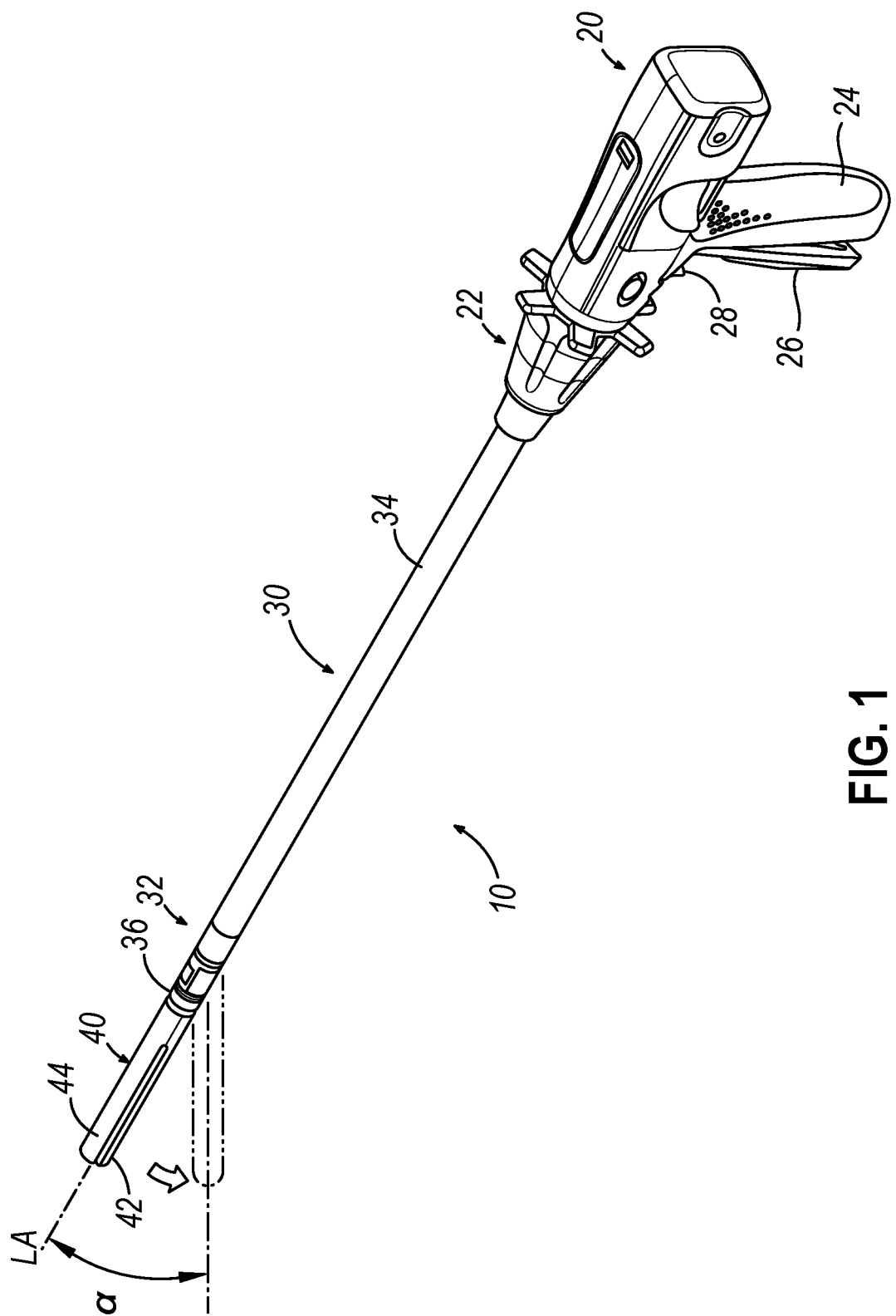
FIG. 1 depicts a perspective view of an example of a surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

Furthermore, the terms "about," "approximately," "substantially," and the like as used herein in connection with any numerical values, ranges of values, and/or geometric/positional quantifications are intended to encompass the exact value(s) referenced as well as a suitable tolerance that enables the referenced feature or combination of features to function for the intended purpose described herein. For example, "substantially parallel" encompasses nominally parallel structures.

As used herein in connection with any examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

I. OVERVIEW OF SURGICAL STAPLER FEATURES

FIGS. 1-6 depict an illustrative surgical stapler (10) that is sized for insertion through a trocar cannula or a surgical incision (e.g., thoracotomy, etc.) to a surgical site in a patient for performing a surgical procedure. Surgical stapler (10) includes a body exemplified as a handle assembly (20), a shaft (30) that extends distally from handle assembly (20) along a longitudinal axis (LA) and distally terminates at an articulation joint (32), and an end effector (40) operatively coupled with shaft (30) via articulation joint (32).

Once end effector (40) and articulation joint (32) are inserted distally through the cannula passageway of a trocar, articulation joint (32) may be remotely articulated, as depicted in phantom in FIG. 1, by an articulation control exemplified as a rotatable knob (22) of handle assembly (20), such that end effector (40) may be deflected from the longitudinal axis (LA) at a desired angle (a). Articulation joint (32) and related features for manipulating articulation joint (32) may be further configured in accordance with the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety.

End effector (40) includes a lower jaw exemplified as a cartridge jaw (42) configured to removably receive a staple cartridge (70) (also referred to as a "reload"), and an upper jaw exemplified as an anvil jaw (44) (also referred to as an "anvil") that pivots relative to cartridge jaw (42) to clamp tissue therebetween. In other versions, end effector (40) may be alternatively configured such that cartridge jaw (42) pivots relative to anvil jaw (44). Unless otherwise described, the term "pivot" (and variations thereof) as used herein in connection with the relative motion between jaws (42, 44) encompasses but is not necessarily limited to pivotal movement about a fixed axis. For instance, in some versions, anvil jaw (44) may pivot about an axis that is defined by a pin (or similar feature) that slidably translates along an elongate slot or channel as anvil jaw (44) moves toward cartridge jaw (42). Such translation may occur before, during, or after the pivotal motion. It should therefore be understood that such combinations of pivotal and translational movement are encompassed by the term "pivot" and variations thereof as used herein with reference to the relative motion between jaws (42, 44).

As shown in FIG. 1, handle assembly (20) includes a pistol grip (24) and a closure trigger (26). Closure trigger (26) is pivotable toward pistol grip (24) to cause clamping, or closing, of anvil jaw (44) toward cartridge jaw (42) of end effector (40). Such closing of anvil jaw (44) is provided through a closure tube (34) and a closure ring (36) of shaft (30), which both longitudinally translate relative to handle assembly (20) in response to pivoting of closure trigger (26) relative to pistol grip (24). Closure tube (34) extends along the length of shaft (30); and closure ring (36) is positioned distal to articulation joint (32). Articulation joint (32) is operable to transmit longitudinal movement from closure tube (34) to closure ring (36) to actuate anvil jaw (44) relative to cartridge jaw (42).

Handle assembly (20) also includes a firing trigger (28). An elongate actuator (not shown) extends longitudinally through shaft (30) and transmits a longitudinal firing motion from handle assembly (20) to a firing member (also referred to herein as a firing driver) exemplified as a firing beam (46) in response to actuation of firing trigger (28). As a result, firing beam (46) translates distally through a firing stroke to cause stapling and severing of tissue clamped by end effector (40), as will be described in greater detail below. Though not shown, handle assembly (20) may further include a motor operable to actuate such firing assembly components of surgical stapler (10) in response to actuation of firing trigger (28) by a user, for example as disclosed in U.S. Pat. No. 8,453,914, entitled "Motor-Driven Surgical Cutting Instrument with Electric Actuator Directional Control Assembly," issued Jun. 4, 2013, the disclosure of which is incorporated by reference herein in its entirety.

As shown in FIGS. 2-5, firing beam (46) includes a proximal beam portion (48) and a distal knife portion (50), where distal knife portion (50) may be integrally formed with a distal end of proximal beam portion (48), or separately formed and thereafter securely affixed to the distal end of proximal beam portion (17). Distal knife portion (50) includes a transversely oriented upper protrusion exemplified as an upper pin (52), a transversely oriented lower protrusion exemplified as a cap (54), a transversely oriented middle protrusion exemplified as a middle pin (56), and a distally presented cutting edge (58). Upper pin (52) is slidable within a longitudinal anvil jaw slot (62) of anvil jaw (44) and cap (54) is slidable along a lower surface of cartridge jaw (42) defined by a longitudinal cartridge jaw slot (64). Middle pin (56) is slidable along a top surface of cartridge jaw (42) and cooperates with cap (54) to stabilize and guide distal knife portion (50) along a longitudinal firing stroke. Firing beam (46) may be further configured and operable in accordance with the teachings of U.S. Pat. No. 9,717,497, entitled "Lockout Feature for Movable Cutting Member of Surgical Instrument," issued Aug. 1, 2017, the disclosure of which is incorporated by reference herein in its entirety.

Figure 2:
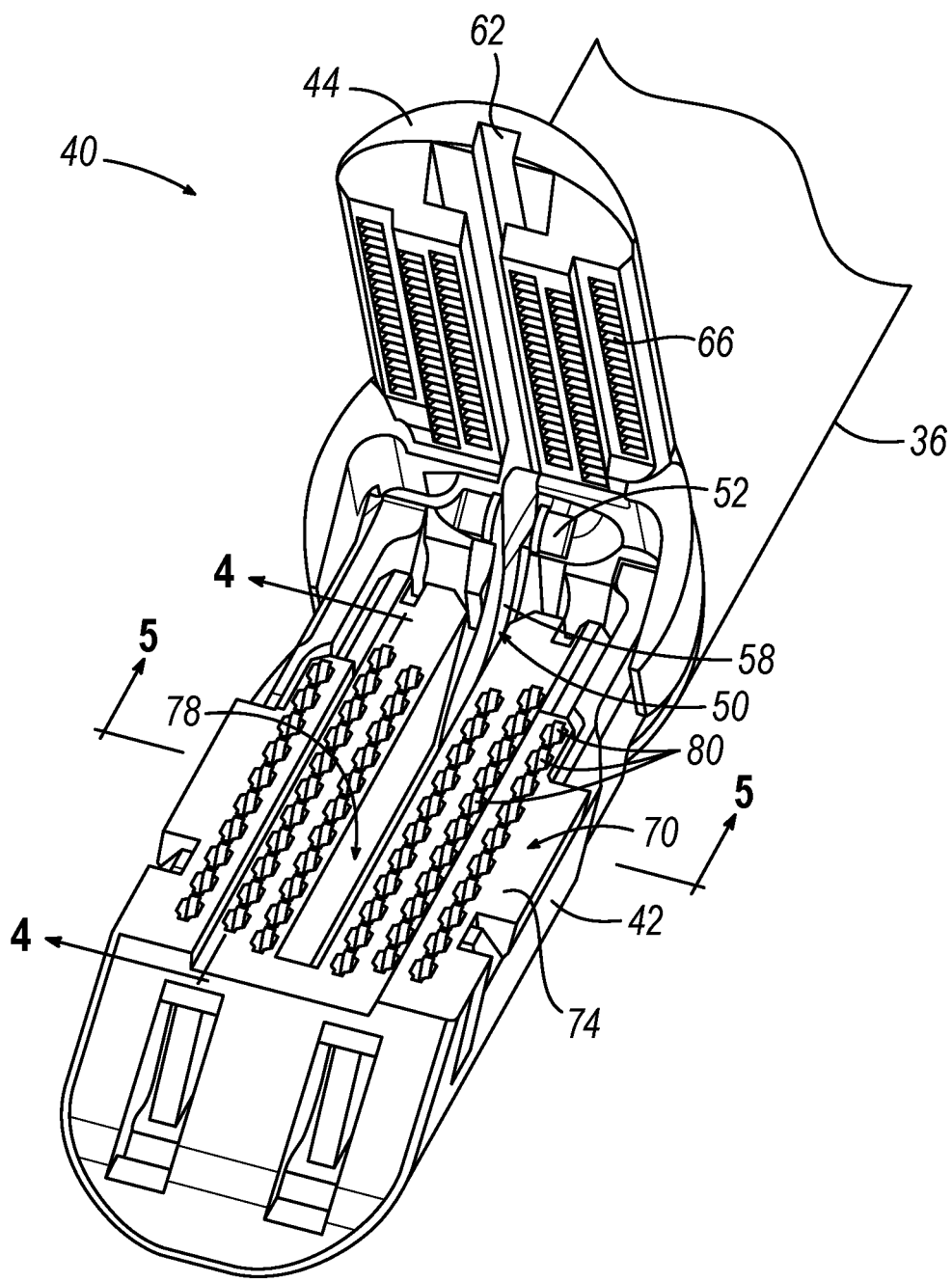
FIG. 2 depicts a perspective view of an end effector of the surgical stapler of FIG. 1, shown in an open state.
Figure 3:
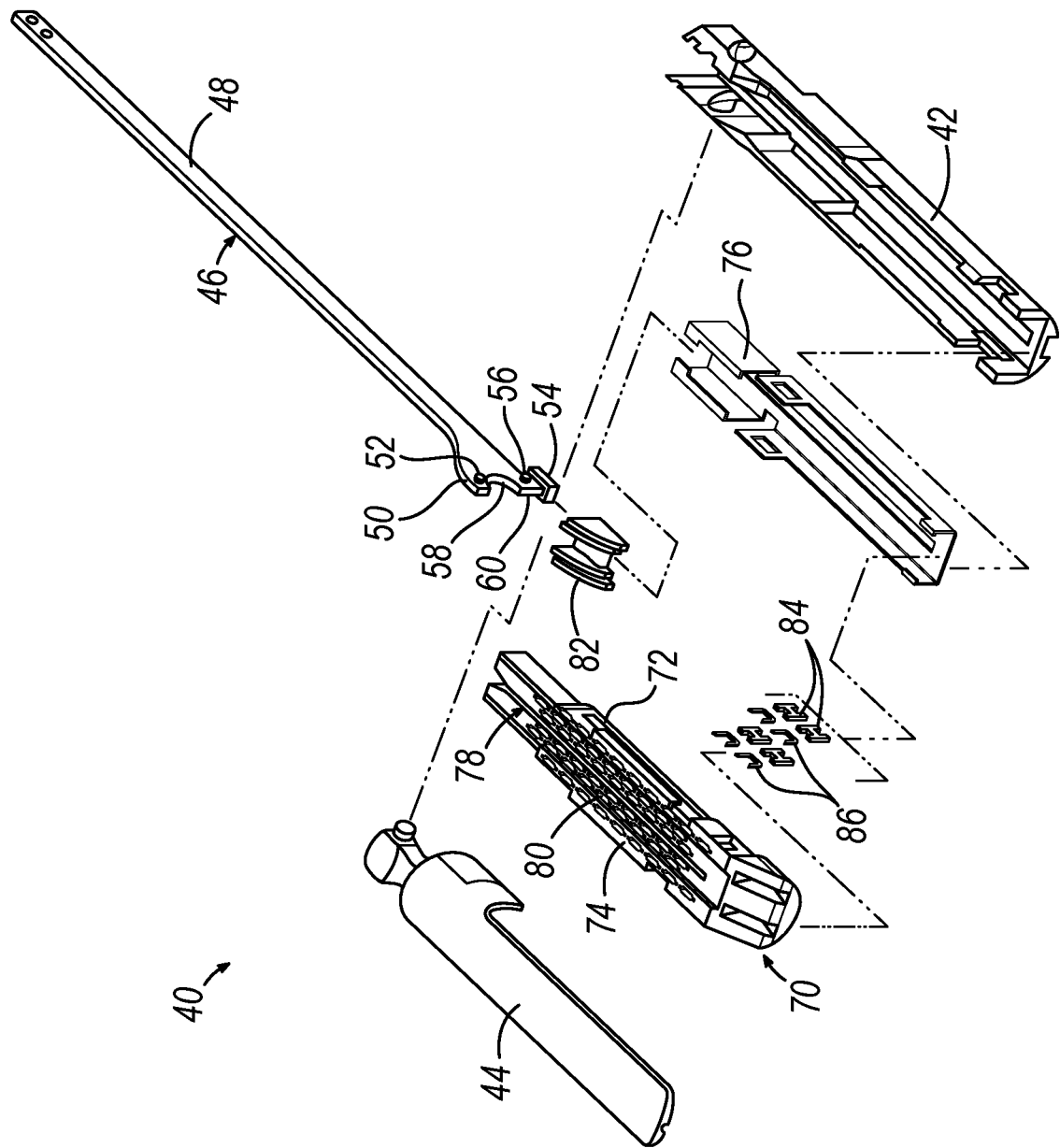
FIG. 3 depicts an exploded perspective view of the end effector of FIG. 2.

FIG. 2 shows anvil jaw (44) pivoted to an open state with firing beam (46) proximally positioned, which permits an unspent (i.e., unfired) staple cartridge (70) to be removably installed into a channel of cartridge jaw (42). As best seen in FIGS. 2-3, staple cartridge (70) includes a cartridge body (72) that presents an upper deck (74) defining a first stapling surface, and a lower pan (76) (also referred to as a "tray") coupled to an underside of cartridge body (72). A vertical knife slot (78) extends longitudinally through cartridge body (72) and is configured to slidably receive distal knife portion (50) of firing beam (46). In the present version, three rows of cartridge pockets (80) (also referred to as "staple openings," "staple apertures," or "staple cavities") are formed through upper deck (74) along each lateral side of knife slot (78).

Figure 4A:
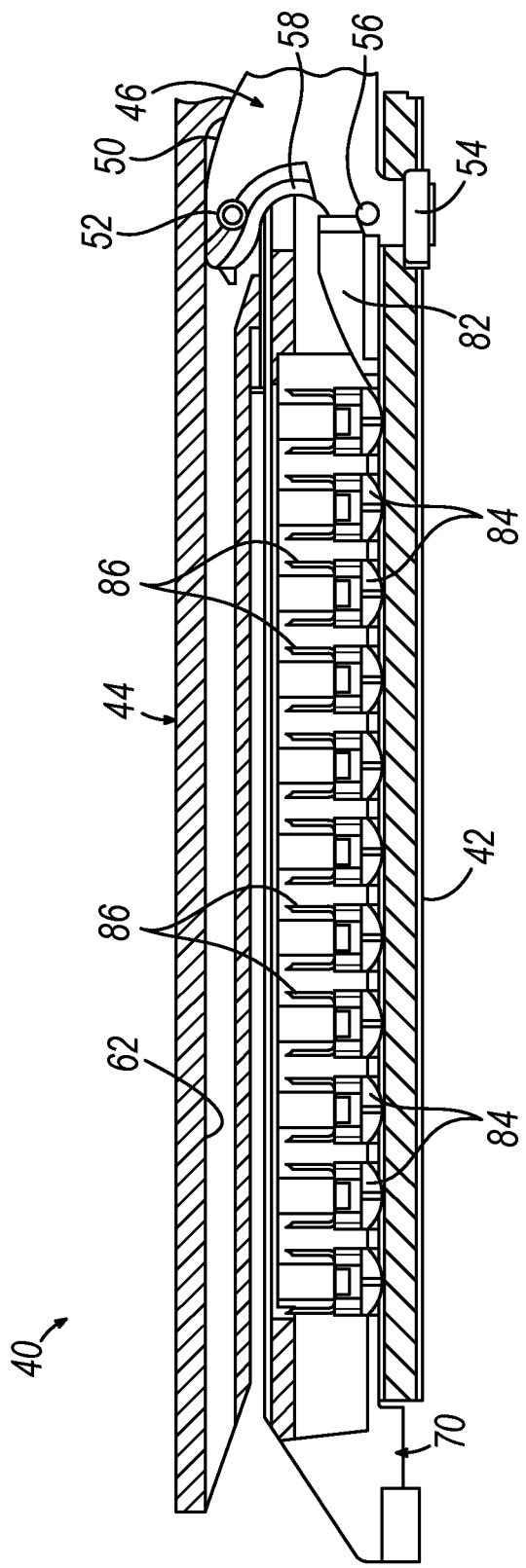
FIG. 4A depicts a side cross-sectional view of the end effector of FIG. 2, taken along line 4-4 of FIG. 2, showing a firing beam and sled in a proximal unfired position.
Figure 4B:
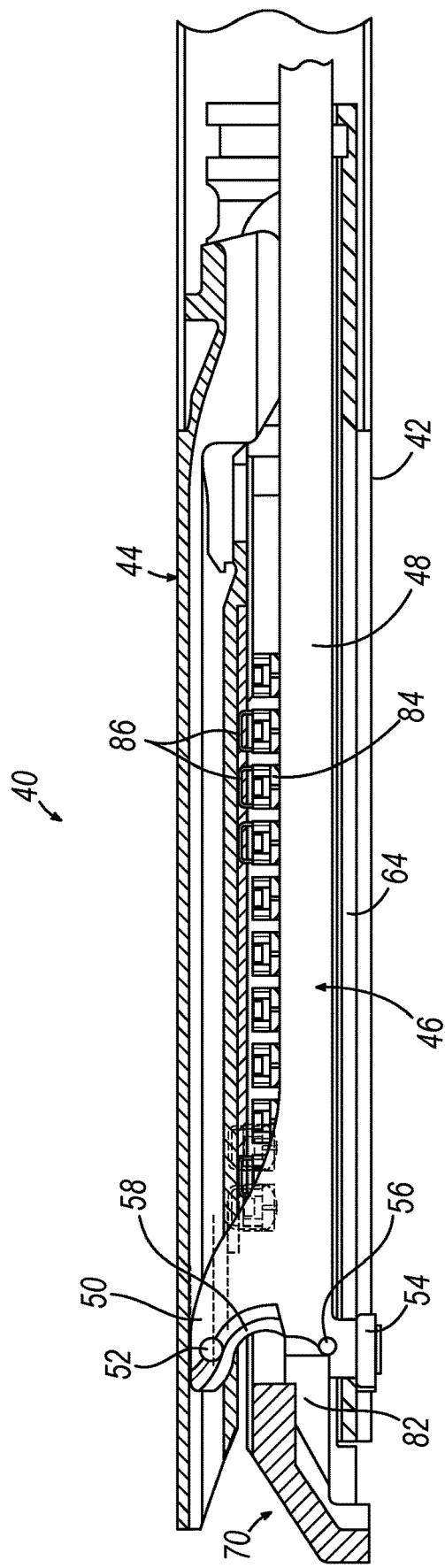
FIG. 4B depicts a side cross-sectional view of the end effector of FIG. 2, taken along line 4-4 of FIG. 2, showing the firing beam and sled in a distal fired position.
Figure 5:
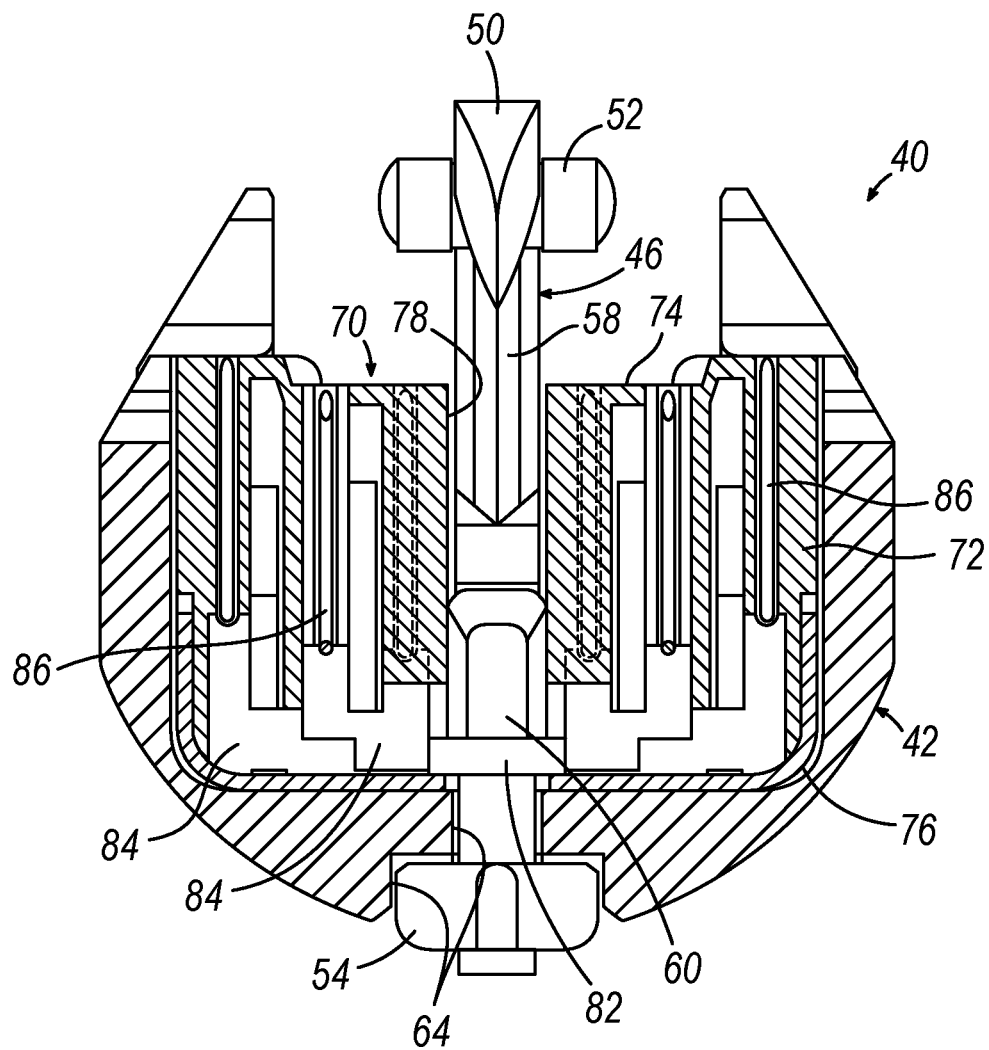
FIG. 5 depicts an end cross-sectional view of the end effector of FIG. 2, taken along line 5-5 of FIG. 2 and omitting an upper anvil jaw, showing further details of a distal knife portion of the firing beam and the sled.

As shown in FIGS. 3-5, staple cartridge (70) further includes a sled (82) (also referred to as a "wedge sled") and a plurality of staple drivers (84) that are movably captured between cartridge body (72) and pan (76). Each staple driver (84) is aligned with and movable vertically within a respective cartridge pocket (80). Staples (86) are positioned within respective cartridge pockets (80) above respective staple drivers (84). During a firing stroke, sled (82) is actuated longitudinally within staple cartridge (70) by distal knife portion (50) from a proximal position shown in FIG. 4A to a distal position shown in FIG. 4B. Angled cam surfaces of sled (82) cam staple drivers (84) vertically upwardly within cartridge pockets (80) to drive staples (86) upwardly above deck (74), thereby ejecting staples (86) from cartridge pockets (80) and toward anvil jaw (44).

More specifically, with end effector (40) closed as shown in FIGS. 4A-4B, firing beam (46) is actuated distally into engagement with anvil jaw (44) by directing upper pin (52) into longitudinal anvil slot (62). A distal end projection (60) (see FIG. 5) of distal knife portion (50) of firing beam (46) engages a proximal end of sled (82) and drives sled (82) distally as distal knife portion (50) is advanced distally through staple cartridge (70) in response to actuation of firing trigger (28). During such firing, distal knife portion (50) advances distally along knife slot (78) of staple cartridge (70) so that cutting edge (58) severs tissue clamped between staple cartridge (70) and anvil jaw (44).

As shown in FIGS. 4A-4B, middle pin (56) and distal end projection (60) together actuate staple cartridge (70) by entering into knife slot (78), driving sled (82) into camming contact with staple drivers (84) to thereby actuate staple drivers (84) upwardly, which in turn drives staples (86) outwardly through cartridge pockets (80), through clamped tissue, and into forming contact with staple forming pockets (66) (see FIG. 2) on a second stapling surface defined by anvil jaw (44). Such stapling of tissue prompted by the camming interaction between sled (82) and staple drivers (84) is performed concurrently with the severing of tissue performed by cutting edge (58). However, it will be appreciated that for each longitudinal section of tissue clamped by end effector (40), staples (86) may be ejected into the tissue slightly before cutting edge (58) severs the tissue to ensure that the tissue is stapled and thus sealed before being severed. FIG. 4B depicts firing beam (46) fully distally translated at the end of a firing stroke after the tissue clamped by end effector (40) has been stapled and severed.

Staple cartridge (70) and anvil jaw (44) may be further configured and operable in accordance with the teachings of U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; U.S. Pat. No. 10,092,292, entitled "Staple Forming Features for Surgical Stapling Instrument," issued Oct. 9, 2018; and/or U.S. Pat. No. 10,130,359, entitled "Method for Forming a Staple," issued Nov. 20, 2018, the disclosure of each of which is incorporated by reference herein in its entirety.

Figure 6:
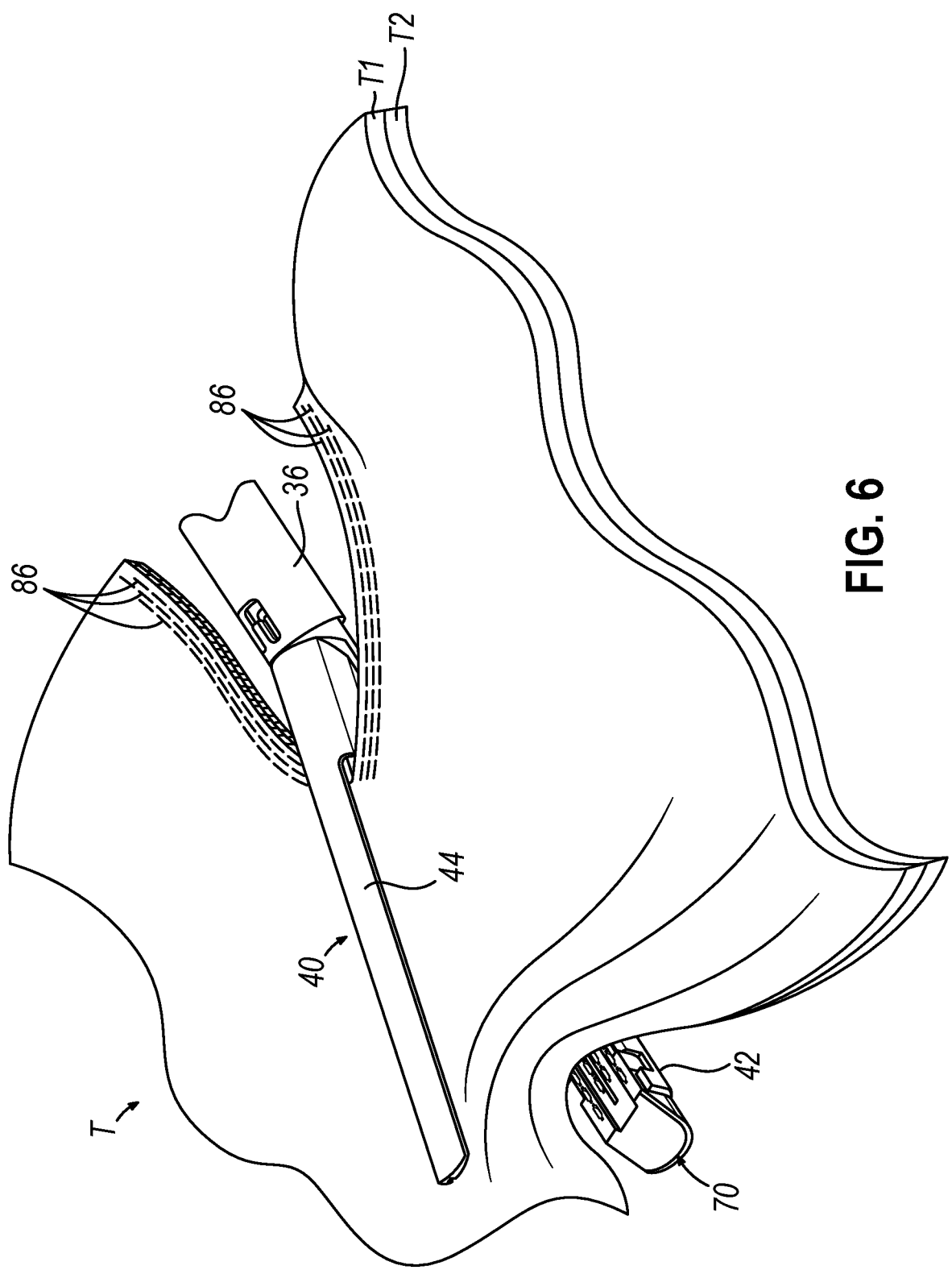
FIG. 6 depicts a perspective view of the end effector of FIG. 2, shown after having been fired once on a first section of tissue and being positioned to clamp and fire on a second section on tissue.

FIG. 6 shows end effector (40) having been actuated through a single firing stroke on tissue (T) having first and second layers (T1, T2). Cutting edge (58) (see FIGS. 2-5) has cut through tissue (T) while staple drivers (84) have driven three alternating rows of staples (86) through tissue (T) on each side of the cut line produced by cutting edge (58). After the first firing stroke is complete, end effector (40) is withdrawn from the patient, spent staple cartridge (70) is replaced with a new unspent staple cartridge (70), and end effector (40) is then again inserted into the patient to reach the stapling site for further cutting and stapling. This process may be repeated until the desired quantity and pattern of firing strokes across the tissue (T) has been completed.

II. EXAMPLES OF BUTTRESS ASSEMBLIES

In some instances, it may be desirable to equip end effector (40) of surgical stapler (10) with an adjunct material, such as a buttress, to reinforce the mechanical fastening of tissue (T) provided by staples (86). Such a buttress may prevent the applied staples (86) from pulling through the tissue (T) and may otherwise reduce a risk of tissue (T) tearing at or near the site of applied staples (86). In addition to or as an alternative to providing structural support and integrity to a line of staples (86), a buttress may provide various other kinds of effects such as spacing or gap-filling, administration of therapeutic agents, and/or other effects. In some instances, a buttress may be provided on upper deck (74) of staple cartridge (70). As described above, deck (74) houses staples (86), which are driven by staple driver (84). In some other instances, a buttress may be provided on the surface of anvil (44) that faces staple cartridge (70). It should also be understood that a first buttress may be provided on upper deck (74) of staple cartridge (70) while a second buttress is provided on anvil (44) of the same end effector (40).

Various examples of forms that a buttress may take will be described in greater detail below. Various ways in which a buttress may be secured to a staple cartridge (70) or an anvil (44) will also be described in greater detail below. Exemplary buttress assemblies, exemplary materials and techniques for applying buttress assemblies, and exemplary buttress applier cartridges may be configured in accordance with at least some of the teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and/or U.S. Pat. No. 11,166,724, entitled "Adhesive Distribution on Buttress for Surgical Stapler," issued Nov. 9, 2021, the disclosures of which are incorporated by reference herein.

A. First Example of a Buttress Assembly

Figure 7:
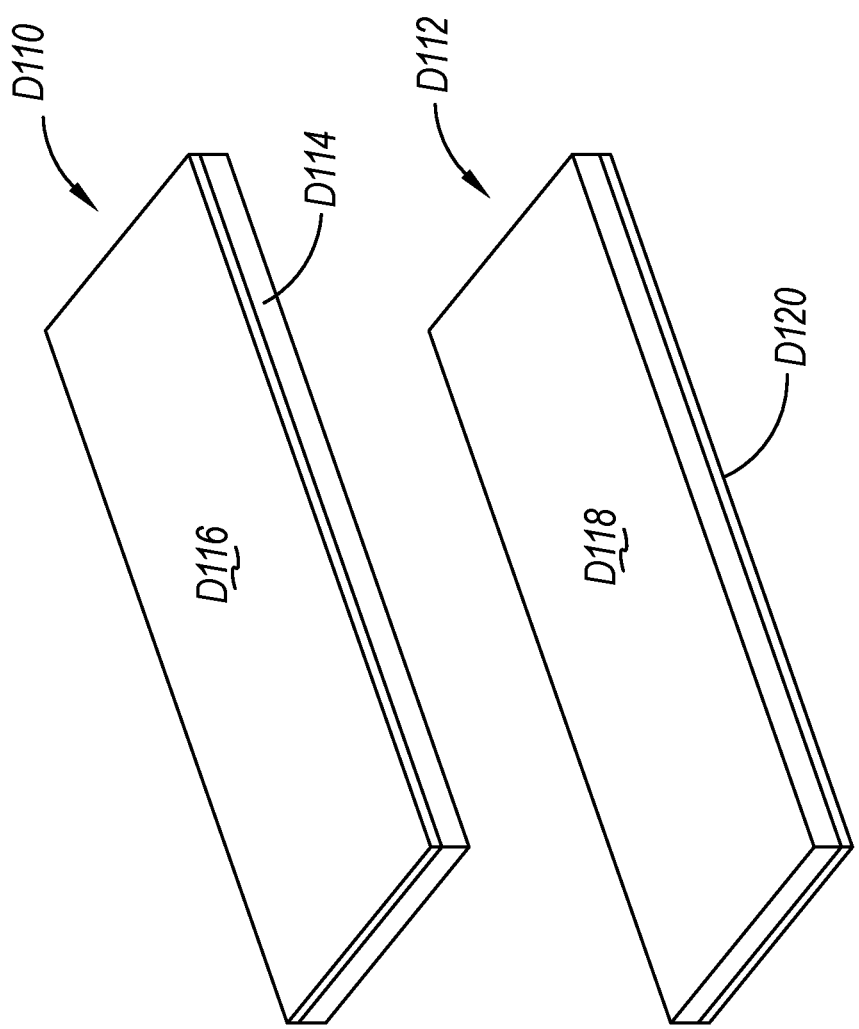
FIG. 7 depicts a perspective view of an exemplary pair of buttress assemblies, each of which may be applied to a jaw of the end effector of FIG. 2.

FIG. 7 shows an exemplary pair of buttress assemblies (D110, D112) (each also referred to individually as a "buttress"). Buttress assembly (D110) of this example comprises a buttress body (D114) and an upper adhesive layer (D116). Similarly, buttress assembly (D112) comprises a buttress body (D118) and a lower adhesive layer (D120). In the present example, each buttress body (D114, D118) comprises a strong yet flexible material configured to structurally support a line of staples (86). By way of example only, each buttress body (D114, D118) may comprise a mesh of polyglactin 910 material by Ethicon, Inc. of Somerville, New Jersey. Alternatively, any other suitable materials or combinations of materials may be used in addition to or as an alternative to polyglactin 910 material to form each buttress body (D114, D118).

Each buttress body (D114, D118) may comprise a material including, for example, a hemostatic agent such as fibrin to assist in coagulating blood and reduce bleeding at the severed and/or stapled surgical site along tissue (T1, T2). As another merely illustrative example, each buttress body (D114, D118) may comprise other adjuncts or hemostatic agents such as thrombin may be used such that each buttress body (D114, D118) may assist to coagulate blood and reduce the amount of bleeding at the surgical site. Other adjuncts or reagents that may be incorporated into each buttress body (D114, D118) may further include but are not limited to medical fluid or matrix components.

In the present example, adhesive layer (D116) is provided on buttress body (D114) to adhere buttress body (D114) to underside (D124) of anvil (44). Similarly, adhesive layer (D120) is provided on buttress body (D118) to adhere buttress body (D118) to upper deck (74) of staple cartridge (70). Such an adhesive material may provide proper positioning of buttress body (D114, D118) before and during actuation of end effector (40); then allow buttress body (D114, D118) to separate from end effector (40) after end effector (40) has been actuated, without causing damage to buttress body (D114, D118) that is substantial enough to compromise the proper subsequent functioning of buttress body (D114, D118).

FIGS. 8A-8C show an exemplary sequence in which surgical stapler end effector (40), which has been loaded with buttress assemblies (D110, D112), is actuated to drive staples (86) through two opposed layers of tissue (T1, T2), with buttress assemblies (D110, D112) being secured to the same layers of tissue (T1, T2) by staples (86). In particular, FIG. 8A shows layers of tissue (T1, T2) positioned between anvil (44) and staple cartridge (70), with anvil (44) in the open position. Buttress assembly (D110) is adhered to an underside of anvil (44) via adhesive layer (D116); while buttress assembly (D112) is adhered to upper deck (74) of staple cartridge (70) via adhesive layer (D120). Layers of tissue (T1, T2) are thus interposed between buttress assemblies (D110, D112). Next, closure trigger (26) is pivoted toward pistol grip (24) to drive closure tube (34) and closure ring (36) distally. This drives anvil (44) to the closed position as shown in FIG. 8B. At this stage, layers of tissue (T1, T2) are compressed between anvil (44) and staple cartridge (70), with buttress assemblies (D110, D112) engaging opposite surfaces of tissue layers (T1, T2). End effector (40) is then actuated as described above, driving staple (86) through buttress assemblies (D110, D112) and tissue (T1, T2). As shown in FIG. 8C, crown (D122) of driven staple (86) captures and retains buttress assembly (D112) against layer of tissue (T2). Deformed legs (D126) of staple (86) capture and retain buttress assembly (D110) against layer of tissue (T1).

Figure 9:
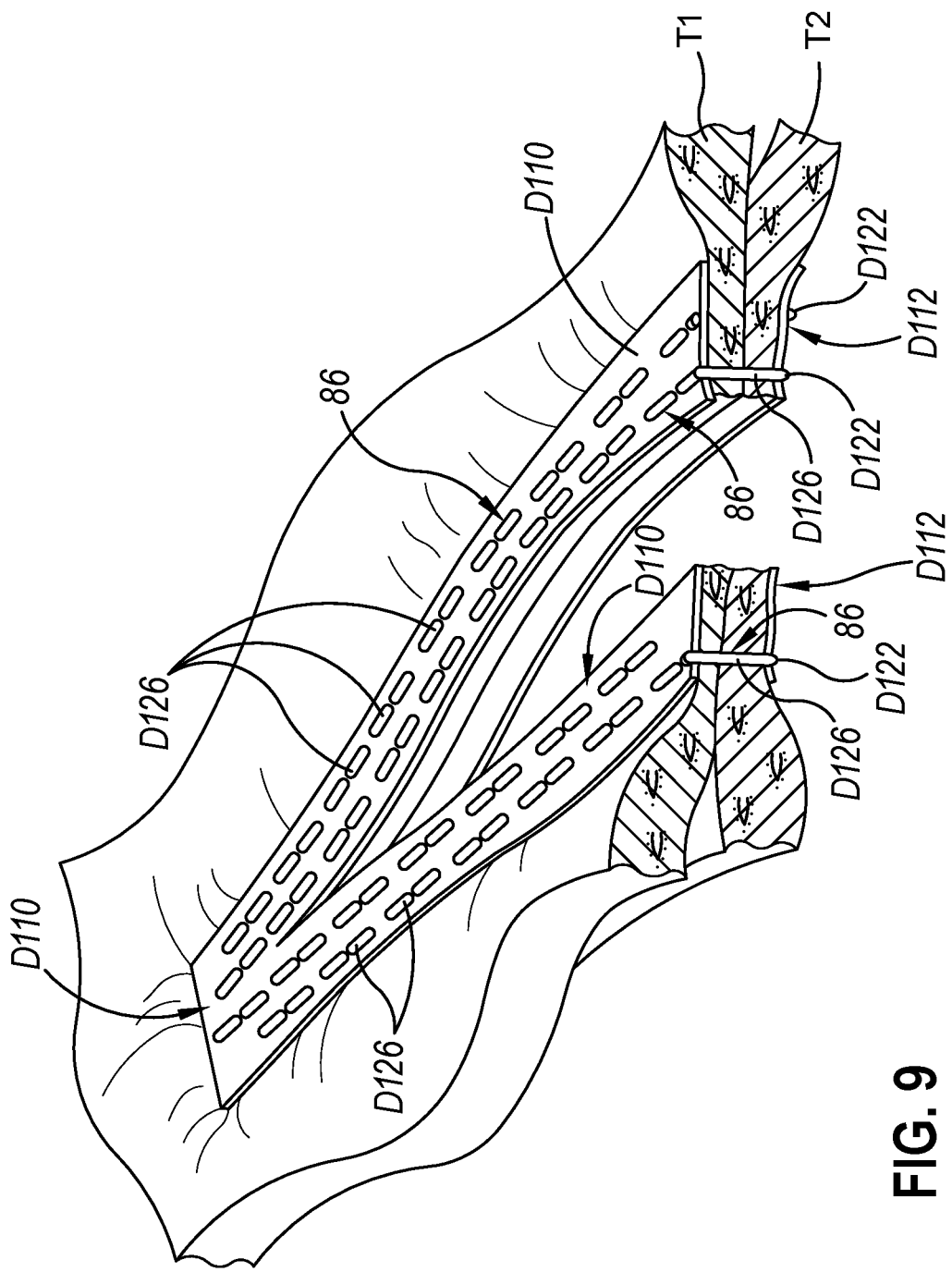
FIG. 9 depicts a perspective view of formed staples and the buttress assemblies of FIG. 8A after having been secured to the tissue by the end effector of FIG. 2.

A series of staples (86) similarly capture and retain buttress assemblies (D110, D112) against layers of tissue (T1, T2), thereby securing buttress assemblies (D110, D112) to tissue (T1, T2) as shown in FIG. 9. As end effector (40) is pulled away from tissue (T1, T2) after deploying staples (86) and buttress assemblies (D110, D112), buttress assemblies (D110, D112) disengage end effector (40) such that buttress assemblies (D110, D112) remain secured to tissue (T1, T2) with staples (86). Buttresses (D110, D112) thus provide structural reinforcement to the lines of staples (86) formed in tissue (T1, T2). As can also be seen in FIG. 9, distally presented cutting edge (58) of firing beam (46) also cuts through a centerline of buttress tissue assemblies (D110, D112), separating each buttress assembly (D110, D112) into a corresponding pair of sections, such that each section remains secured to a respective severed region of tissue (T1, T2).

B. Second Example of a Buttress Assembly

Figure 10:
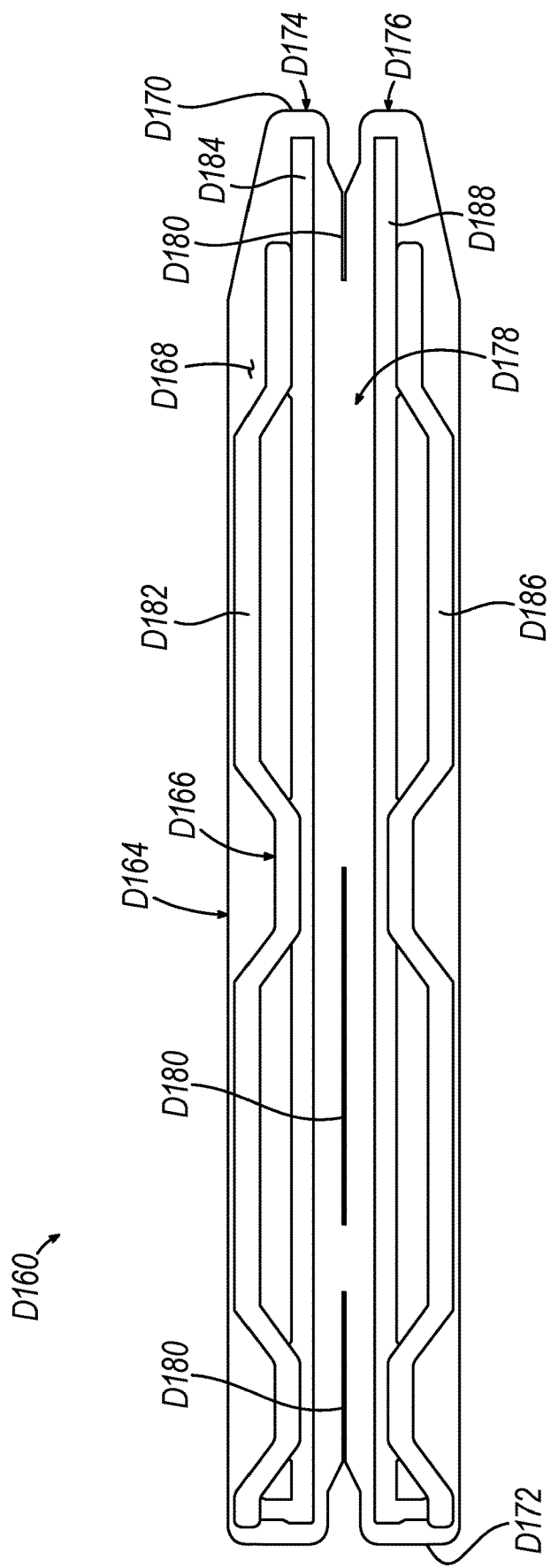
FIG. 10 depicts a top plan view of another example of a buttress assembly which may be applied to a jaw of the end effector of FIG. 2.

FIG. 10 illustrates another example of a buttress assembly (D160), which may be similar to buttress assemblies (D110, D112) described above, except as otherwise described below. In this regard, buttress assembly (D160) comprises a buttress body (D164) and an adhesive (D166) on a surface (D168) of buttress body (D164). Buttress body (D164) may comprise one or more layers of material. Where multiple layers are used the layers can be laminated together. In some examples buttress body (D164) comprises a mesh layer and one or more film layers laminated together. In some other examples buttress body (D164) comprises one or more film layers without a mesh layer. In view of the teachings herein, other various materials for one or more layers of buttress body (D164) will be apparent to those of ordinary skill in the art.

In the present example, buttress body (D164) is comprised of an absorbable material that is configured to be completely absorbed by the patient's body when used to reinforce a cut and staple site. In some examples, buttress body (D164) is comprised of polyglactin 910, which is 90% glycolide and 10% L-lactide. An example of polyglactin 910 is manufactured by Ethicon Inc. under the brand name Vicryl®. In view of the teachings herein, other absorbable synthetic materials for use with buttress body (D164) will be apparent to those of ordinary skill in the art.

Buttress body (D164) extends along a longitudinal axis between a proximal end (D170) and a distal end (D172), and defines a length extending from proximal end (D170) to distal end (D172). Buttress body (D164) includes a first edge region (D174), a second edge region (D176), and a center region (D178) between and separating first edge region (D174) and second edge region (D176). Buttress body (D164) defines a width extending orthogonal to its length as defined above, where its width extends from first edge region (D174) across center region (D178) and through second edge region (D176).

Figure 8:
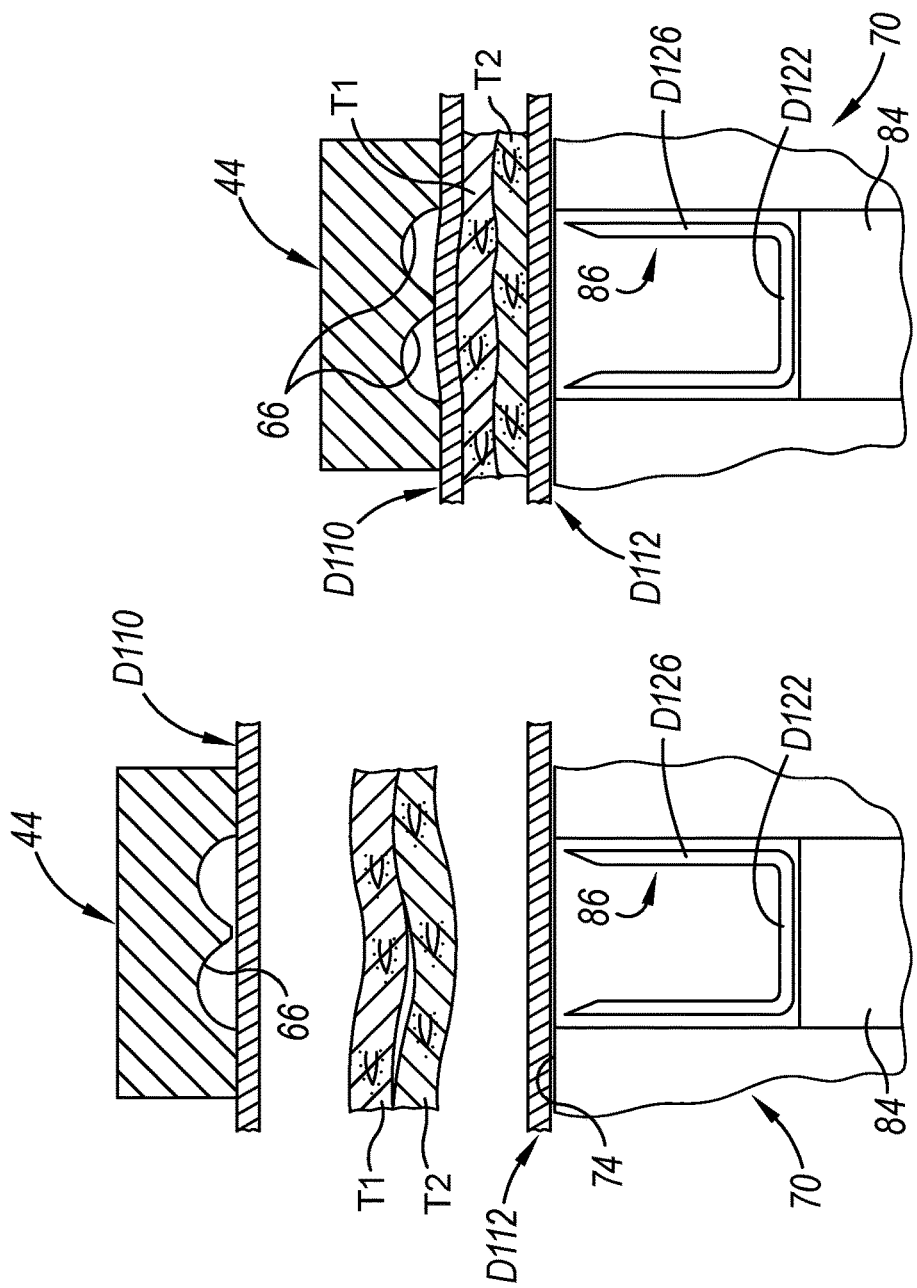
FIG. 8A depicts a cross-sectional end view of a portion of the end effector of FIG. 2 with the buttress assemblies of FIG. 7 applied to the upper and lower jaws of the end effector, showing the end effector jaws in an open state with tissue positioned between the upper and lower jaws.
FIG. 8B depicts a cross-sectional end view of the end effector and buttress assemblies of FIG. 8A, showing the end effector jaws in a closed state on the tissue.
FIG. 8C depicts a cross-sectional view of a formed staple and the buttress assemblies of FIG. 8A after having been secured to the tissue by the end effector of FIG. 2.

Adhesive (D166) extends from proximal end (D170) to distal end (D172) of buttress body (D164). Moreover, in the present example, adhesive (D166) extends continuously or in an uninterrupted manner. As shown in FIG. 8, adhesive (D166) is located along first edge region (D174) and second edge region (D176), with center region (D178) being substantially free of adhesive (D166). As shown in FIG. 8, center region (D178) of buttress body (D164) comprises slits (D180) that are configured to promote or facilitate cutting and separating buttress body (D164) into substantially equal halves during a cutting and stapling operation as discussed above. In the present example, the longitudinal axis of buttress body (D164) passes through slits (D180), and on each side of center region (D178), adhesive (D166) defines a pattern that is substantially symmetrical with the other side about the longitudinal axis.

Adhesive (D166) comprises a first bead (D182) and a second bead (D184) applied to first edge region (D174), and a third bead (D186) and a fourth bead (D188) applied to second edge region (D176). Each bead of adhesive (D182, D184, D186, D188) extends generally from proximal end (D170) of buttress body (D164) to distal end (D172) of buttress body (D164). Second and fourth beads of adhesive (D184, D188) extend further proximally compared to first and third beads of adhesive (D182, D186), while all four beads of adhesive (D182, D184, D186, D188) extend distally to substantially the same extent relative to buttress body (D164). As mentioned above, first and second beads of adhesive (D182, D184) are collectively symmetrical with third and fourth beads of adhesive (D186, D188) about the longitudinal axis defining the centerline of buttress body (D164). This arrangement results in more adhesive (D166) at distal end (D172) compared to proximal end (D170) of buttress body (D164). In examples like the present one where more adhesive (D166) is present at distal end (D172) of buttress body (D164), this helps buttress body (D164) stay attached and aligned to and with the respective parts of end effector (40) when aggressively manipulating end effector (40), i.e., when piercing through ostomies, sliding axially onto tissue, etc.

It will be appreciated that surgical stapler end effector (40) may be loaded with one or more buttress assemblies (D160) and actuated to drive staples (86) through two opposed layers of tissue (T1, T2), with the one or more buttress assemblies (D160) being secured to the same layers of tissue (T1, T2) by staples (86), in a manner similar to that described above in connection with FIGS. 8A-9.

III. EXAMPLES OF CARTRIDGES HAVING RAISED SURFACES FOR BUTTRESS ADHESION

In some instances, it may be desirable to increase the surface area of the regions of staple cartridge (70) that contact the adhesive layers or beads (D116, D120, D182, D184, D186, D188) of a corresponding buttress assembly (D110, D112, D160), such as in cases where staple cartridge (70) includes pocket extenders or other raised features whose height might inhibit the adhesive layers or beads (D116, D120, D182, D184, D186, D188) from reaching deck (74). For example, increasing the surface area of such regions of staple cartridge (70) may improve the adhesion of the corresponding buttress assembly (D110, D112, D160) to staple cartridge (70).

More particularly, it may be desirable to improve the adhesion of a buttress assembly (D110, D112, D160) at a distal end of staple cartridge (70). Because the distal end of staple cartridge (70) is the first part of staple cartridge (70) to contact tissue when positioning end effector (40), the distal end of staple cartridge (70) can be subject to greater forces in use compared to the proximal end of staple cartridge (70). Because of this, having stronger attachment of buttress assemblies (D110, D112, D160) at the distal end of staple cartridge (70) can be beneficial to maintaining attachment and alignment of buttress assemblies (D110, D112, D160) with respective parts of staple cartridge (70) (e.g., by inhibiting prying of the buttress assemblies (D110, D112, D160) away from staple cartridge (70) by anatomical structures encountered by the distal end of staple cartridge (70)). In addition, or alternatively, it may be desirable to improve the adhesion of a buttress assembly (D110, D112, D160) at a proximal end of staple cartridge (70). For example, such improved adhesion at the proximal end of staple cartridge (70) may inhibit movement (e.g., "plowing") of the buttress assembly (D110, D112, D160), such as by impeding the buttress assembly (D110, D112, D160) from moving distally during distal translation of firing beam (46) (e.g., during a firing stroke). In addition, or alternatively, it may be desirable to improve the adhesion of a buttress assembly (D110, D112, D160) at one or more discrete locations along the length of staple cartridge (70) between the proximal and distal ends of staple cartridge (70).

Each of the examples of staple cartridges (D210, D310, D410, D510, D610, D710, D810, D910) described below provides such functionality.

A. First Example of Staple Cartridge with Enlarged Distal Pocket Extenders

Figure 11:
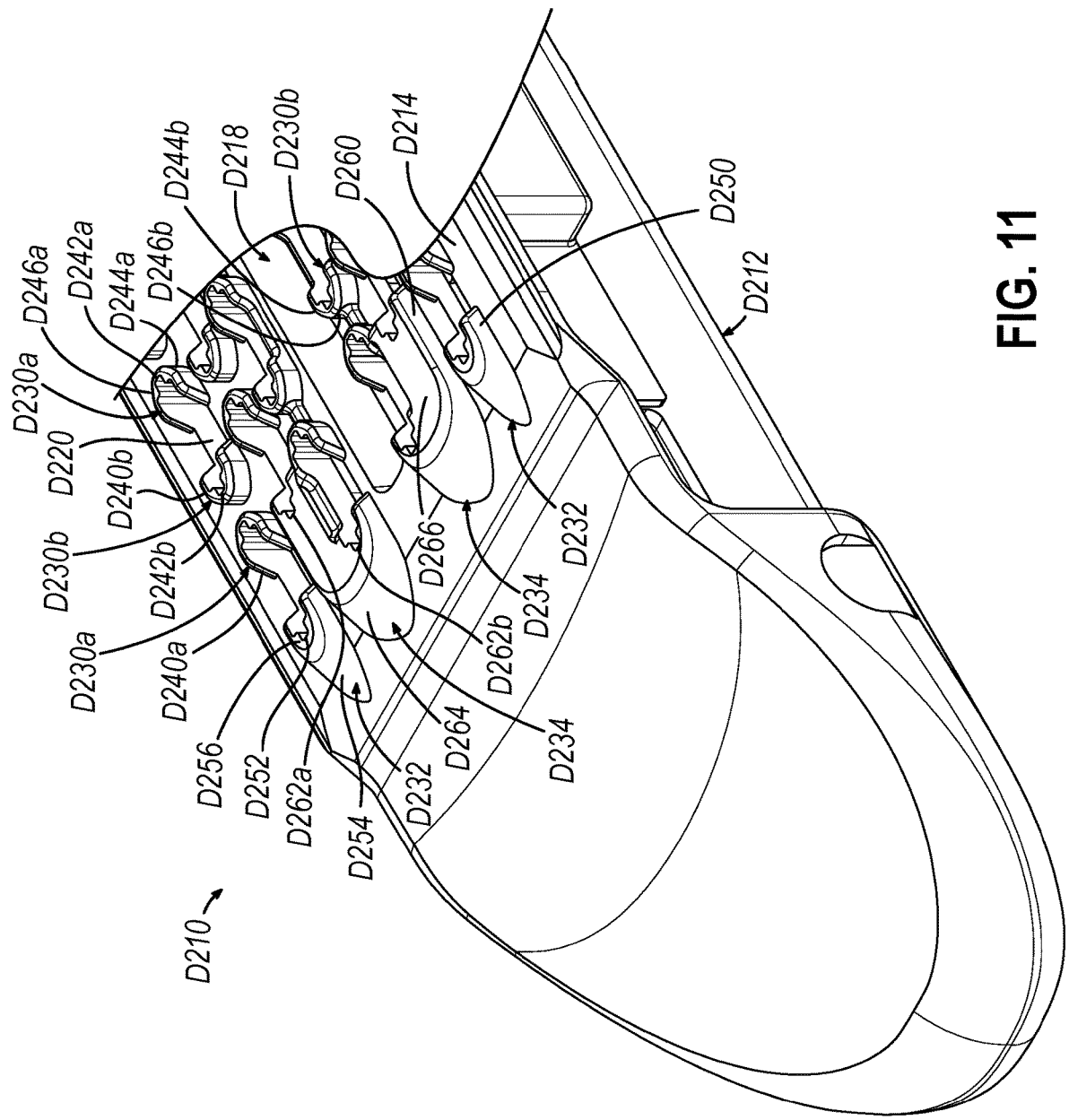
FIG. 11 depicts a partial perspective view of another example of a staple cartridge for use with the end effector of FIG. 2 and having enlarged distal pocket extenders with distal ramp surfaces that are rounded in the lateral direction, the enlarged distal pocket extenders being configured to promote adhesion of any of the buttress assemblies of FIGS. 7-10 to the staple cartridge.

FIG. 11 shows a portion of another example of a staple cartridge (D210) configured to deploy staples (86) toward corresponding staple forming pockets of an anvil (not shown), such as staple forming pockets (66) of anvil (44). Staple cartridge (D210) is configured for use with end effector (40), and is similar to staple cartridge (70) described above except as otherwise described below. In this regard, staple cartridge (D210) of the present example includes a cartridge body (D212) having an upwardly facing deck (D214), an elongate slot (D218) extending along a central axis of cartridge body (D212) and opening upwardly through deck (D214) for slidably receiving a distal knife portion of a firing beam (not shown), such as distal knife portion (50) of firing beam (46), and a plurality of cartridge pockets (D220) extending through deck (D214) on each side of knife slot (D218). In the present version, three longitudinal rows of cartridge pockets (D220) are formed through upper deck (D214) along each lateral side of knife slot (D218), including an inner row, a middle row, and an outer row on each lateral side of knife slot (D218). Each cartridge pocket (D220) slidably houses an unformed staple (86) and a respective staple driver (not shown) similar to staple drivers (84) positioned beneath staple (86). A lower tray (not shown) similar to lower tray (76) encloses an underside of cartridge body (D212) and thereby retains staples (86) and the staple drivers within cartridge body (D212). A wedge sled (not shown) similar to wedge sled (82) is slidably disposed within cartridge body (D212) and includes upwardly presented cam surfaces configured to engage the undersides of the staple drivers.

Staple cartridge (D210) of the present example further includes a plurality of raised features in the form of pocket extenders (D230a, D230b, D232, D234) that extend upwardly from deck (D214) at or near proximal and distal ends of each cartridge pocket (D220), such that each cartridge pocket (D220) is longitudinally flanked by a corresponding pair of proximal and distal pocket extenders (D230a, D230b, D232, D234). Any one or more of pocket extenders (D230a, D230b, D232, D234) may be configured to enhance the gripping of tissue (T1, T2) by staple cartridge (D210) when end effector (40) is closed (e.g., in instances when staple cartridge (D210) is not equipped with a buttress assembly (D110, D112, D160)), and/or to guide the legs (D126) of the staples (86) as the legs (D126) exit the respective cartridge pockets (D220) during deployment of the staples (86). In addition, or alternatively, any one or more of pocket extenders (D230a, D230b, D232, D234) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D210).

In the example shown, the plurality of pocket extenders (D230a, D230b, D232, D234) include a plurality of first pocket extenders (D230a, D230b) having a first configuration, a plurality of second pocket extenders (D232) having a second configuration different from the first configuration, and a plurality of third pocket extenders (D234) having a third configuration different from the first and second configurations. First pocket extenders (D230a, D230b) include proximal first pocket extenders (D230a) that are positioned at or near the proximal ends of each cartridge pocket (D220) of each row, and further include distal first pocket extenders (D230b) that are positioned at or near the distal ends of each cartridge pocket (D220) of each row, except for the distalmost cartridge pocket (D220) of each row. In this regard, second pocket extenders (D232) are positioned at or near the distal ends of the distalmost cartridge pockets (D220) of the outer rows, and third pocket extenders (D234) are positioned at or near the distal ends of the distalmost cartridge pockets (D220) of the inner and middle rows such that each third pocket extender (D234) spans laterally across two rows of cartridge pockets (D220) on the respective lateral side of knife slot (D218) (e.g., the respective inner and middle rows of cartridge pockets (D220)).

As shown, each first pocket extender (D230a, D230b) includes a generally U-shaped body (D240a, D240b) that defines a staple leg receptacle (D242a, D242b) for receiving a corresponding leg (D126) of the staple (86) slidably housed within the respective cartridge pocket (D220). In this regard, each staple leg receptacle (D242a, D242b) may be sized and configured to slidably receive the corresponding leg (D126) for vertically guiding the corresponding leg (D126) out of the respective cartridge pocket (D220) toward the corresponding staple forming pockets (66) as staples (86) are driven outwardly from cartridge pockets (D220) by the staple drivers. The body (D240a) of each proximal first pocket extender (D230a) also defines a proximally-facing outer surface (D244a) that extends substantially orthogonally relative to deck (D214), while the body (D240b) of each distal first pocket extender (D230b) also defines a distally-facing outer surface (D244b) that extends substantially orthogonally relative to deck (D214). The body (D240a, D240b) of each first pocket extender (D230a, D230b) further defines an upwardly-facing top (e.g., uppermost) surface (D246a, D246b) that extends substantially parallel relative to deck (D214). Top surfaces (D246a, D246b) may be positioned at a substantially uniform height above deck (D214).

Each second pocket extender (D232) includes a generally U-shaped body (D250) that defines a staple leg receptacle (D252) for receiving a corresponding leg (D126) of the staple (86) slidably housed within the respective distalmost, outer cartridge pocket (D220). In this regard, each staple leg receptacle (D252) may be sized and configured to slidably receive the corresponding leg (D126) for vertically guiding the corresponding leg (D126) out of the respective cartridge pocket (D220) toward the corresponding staple forming pockets (66) as staples (86) are driven outwardly from cartridge pockets (D220) by the staple drivers. The body (D250) of each second pocket extender (D232) also defines a distally-facing outer surface (D254) that extends substantially obliquely relative to deck (D214). In the example shown, the outer surface (D254) of each second pocket extender (D232) is rounded in the lateral direction. By extending substantially obliquely relative to deck (D214) and/or by being rounded in the lateral direction, the outer surface (D254) of each second pocket extender (D232) may have a substantially atraumatic configuration so that each outer surface (D254) may avoid inflicting trauma to tissue contacted by the outer surface (D254). For example, each outer surface (D254) may define a distal ramp for gently lifting such tissue upwardly relative to deck (D214).

The body (D250) of each second pocket extender (D232) further defines an upwardly-facing top surface (D256) that extends substantially parallel relative to deck (D214). Top surfaces (D256) may be positioned at a substantially same height above deck (D214) as that of top surfaces (D246a, D246b). In some other versions, top surfaces (D256) may be positioned at a lower height above deck (D214) than that of top surfaces (D246a, D246b). In the example shown, the top surface (D256) of each second pocket extender (D232) has a surface area that is greater than that of the top surface (D246a, D246b) of each first pocket extender (D230a, D230b). The top surface (D256) of each second pocket extender (D232) may also extend further distally compared to the top surface (D246b) of a distal first pocket extender (D230b) if such a distal first pocket extender (D230b) were substituted for the respective second pocket extender (D232). By having a greater surface area and/or extending further distally compared to the top surface (D246a, D246b) of each first pocket extender (D230a, D230b), the top surface (D256) of each second pocket extender (D232) may be configured to provide improved contact with the adhesive layers or beads (D116, D120, D182, D184, D186, D188) of a corresponding buttress assembly (D110, D112, D160), at least relative to the top surface (D246a, D246b) of each first pocket extender (D230a, D230b). For example, the further distal extension of the top surface (D256) of each second pocket extender (D232) may allow the top surface (D256) to vertically align with more adhesive (D166) at distal end (D172) of buttress body (D164) compared to the top surface (D246b) of a distal first pocket extender (D230b) if such a distal first pocket extender (D230b) were substituted for the respective second pocket extender (D232), and may thereby provide stronger, localized attachment of buttress assembly (D160) at the distal end of staple cartridge (D210).

As noted above, each third pocket extender (D234) spans laterally across the respective inner and middle rows of cartridge pockets (D220), and is positioned at or near the distal ends of the distalmost cartridge pockets (D220) of the respective inner and middle rows. Each third pocket extender (D234) includes a generally J-shaped body (D260) that defines proximal and distal staple leg receptacles (D262a, D262b) for receiving corresponding legs (D126) of the staples (86) slidably housed within the respective distalmost, inner and middle cartridge pockets (D220). In this regard, each staple leg receptacle (D262a, D262b) may be sized and configured to slidably receive the corresponding leg (D126) for vertically guiding the corresponding leg (D126) out of the respective cartridge pocket (D220) toward the corresponding staple forming pockets (66) as staples (86) are driven outwardly from cartridge pockets (D220) by the staple drivers.

The body (D260) of each third pocket extender (D234) also defines a distally-facing outer surface (D264) that extends substantially obliquely relative to deck (D214). In the example shown, the outer surface (D264) of each third pocket extender (D234) is rounded in the lateral direction. By extending substantially obliquely relative to deck (D214)

and/or by being rounded in the lateral direction, the outer surface (D264) of each third pocket extender (D234) may have a substantially atraumatic configuration so that each outer surface (D264) may avoid inflicting trauma to tissue contacted by the outer surface (D264). For example, each outer surface (D264) may define a distal ramp for gently lifting such tissue upwardly relative to deck (D214). Due to the spanning of each third pocket extender (D234) laterally across the respective inner and middle rows of cartridge pockets (D220), each outer surface (D264) may be configured to lift the portions of such tissue that are aligned with both the respective inner and middle rows of cartridge pockets (D220), and to do so substantially simultaneously with the lifting of the portions of such tissue that are aligned with the respective outer row of cartridge pockets (D220) by the outer surface (D254) of the corresponding second pocket extender (D232).

The body (D260) of each third pocket extender (D234) further defines an upwardly-facing top surface (D266) that extends substantially parallel relative to deck (D214). Top surfaces (D266) may be positioned at a substantially same height above deck (D214) as that of top surfaces (D246a, D246b). In some other versions, top surfaces (D266) may be positioned at a lower height above deck (D214) than that of top surfaces (D246a, D246b). In the example shown, the top surface (D266) of each third pocket extender (D234) has a surface area that is greater than that of the top surface (D246a, D246b) of each first pocket extender (D230a, D230b). The top surface (D266) of each third pocket extender (D234) may also extend further distally compared to the top surfaces (D246b) of a pair of distal first pocket extenders (D230b) if such a pair of distal first pocket extenders (D230b) were substituted for the respective third pocket extender (D234). By having a greater surface area and/or extending further distally compared to the top surface (D246a, D246b) of each first pocket extender (D230a, D230b), the top surface (D266) of each third pocket extender (D234) may be configured to provide improved contact with the adhesive layers or beads (D116, D120, D182, D184, D186, D188) of a corresponding buttress assembly (D110, D112, D160), at least relative to the top surface (D246a, D246b) of each first pocket extender (D230a, D230b). For example, the further distal extension of the top surface (D266) of each third pocket extender (D234) may allow the top surface (D266) to vertically align with more adhesive (D166) at distal end (D172) of buttress body (D164) compared to the top surfaces (D246b) of a pair of distal first pocket extenders (D230b) if such a pair of distal first pocket extenders (D230b) were substituted for the respective third pocket extender (D234), and may thereby provide stronger, localized attachment of buttress assembly (D160) at the distal end of staple cartridge (D210).

Due to the spanning of each third pocket extender (D234) laterally across the respective inner and middle rows of cartridge pockets (D220), the surface area of the top surface (D266) of each third pocket extender (D234) may also be greater than that of the top surface (D256) of each second pocket extender (D232). By having a greater surface area compared to the top surface (D256) of each second pocket extender (D232), the top surface (D256) of each second pocket extender (D232) may be configured to provide improved contact with the adhesive layers or beads (D116, D120, D182, D184, D186, D188) of a corresponding buttress assembly (D110, D112, D160), at least relative to the top surface (D256) of each second pocket extender (D232) as well.

While each third pocket extender (D234) is shown spanning laterally across the respective inner and middle rows of cartridge pockets (D220), each third pocket extender (D234) may alternatively span laterally across the respective middle and outer rows of cartridge pockets (D220), and/or may span laterally across all three respective rows of cartridge pockets (D220).

B. Second Example of Staple Cartridge with Enlarged Distal Pocket Extenders

Figure 12:
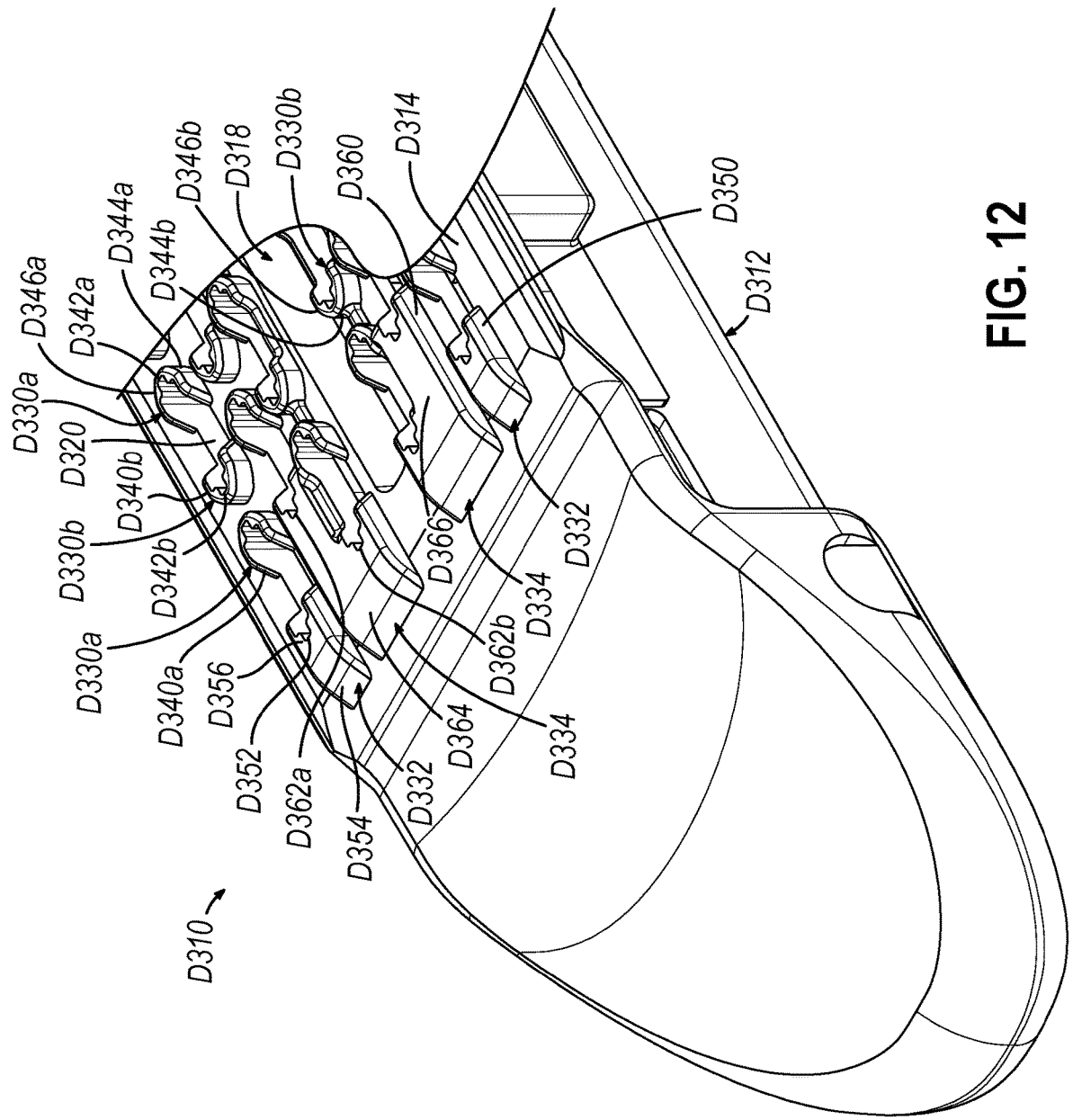
FIG. 12 depicts a partial perspective view of another example of a staple cartridge for use with the end effector of FIG. 2 and having enlarged distal pocket extenders with distal ramp surfaces that are rounded in the longitudinal direction, the enlarged distal pocket extenders being configured to promote adhesion of any of the buttress assemblies of FIGS. 7-10 to the staple cartridge.

FIG. 12 shows a portion of another example of a staple cartridge (D310) configured to deploy staples (86) toward corresponding staple forming pockets of an anvil (not shown), such as staple forming pockets (66) of anvil (44). Staple cartridge (D310) is configured for use with end effector (40), and is similar to staple cartridge (70) described above except as otherwise described below. In this regard, staple cartridge (D310) of the present example includes a cartridge body (D312) having an upwardly facing deck (D314), an elongate slot (D318) extending along a central axis of cartridge body (D312) and opening upwardly through deck (D314) for slidably receiving a distal knife portion of a firing beam (not shown), such as distal knife portion (50) of firing beam (46), and a plurality of cartridge pockets (D320) extending through deck (D314) on each side of knife slot (D318). In the present version, three longitudinal rows of cartridge pockets (D320) are formed through upper deck (D314) along each lateral side of knife slot (D318), including an inner row, a middle row, and an outer row on each lateral side of knife slot (D318). Each cartridge pocket (D320) slidably houses an unformed staple (86) and a respective staple driver (not shown) similar to staple drivers (84) positioned beneath staple (86). A lower tray (not shown) similar to lower tray (76) encloses an underside of cartridge body (D312) and thereby retains staples (86) and the staple drivers within cartridge body (D312). A wedge sled (not shown) similar to wedge sled (82) is slidably disposed within cartridge body (D312) and includes upwardly presented cam surfaces configured to engage the undersides of the staple drivers.

Staple cartridge (D310) of the present example further includes a plurality of raised features in the form of pocket extenders (D330a, D330b, D332, D334) that extend upwardly from deck (D314) at or near proximal and distal ends of each cartridge pocket (D320), such that each cartridge pocket (D320) is longitudinally flanked by a corresponding pair of proximal and distal pocket extenders (D330a, D330b, D332, D334). Any one or more of pocket extenders (D330a, D330b, D332, D334) may be configured to enhance the gripping of tissue (T1, T2) by staple cartridge (D310) when end effector (40) is closed (e.g., in instances when staple cartridge (D310) is not equipped with a buttress assembly (D110, D112, D160)), and/or to guide the legs (D126) of the staples (86) as the legs (D126) exit the respective cartridge pockets (D320) during deployment of the staples (86). In addition, or alternatively, any one or more of pocket extenders (D330a, D330b, D332, D334) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D310).

In the example shown, the plurality of pocket extenders (D330a, D330b, D332, D334) include a plurality of first pocket extenders (D330a, D330b) having a first configuration, a plurality of second pocket extenders (D332) having a second configuration different from the first configuration, and a plurality of third pocket extenders (D334) having a third configuration different from the first and second configurations. First pocket extenders (D330a, D330b) include proximal first pocket extenders (D330a) that are positioned at or near the proximal ends of each cartridge pocket (D320) of each row, and further include distal first pocket extenders (D330b) that are positioned at or near the distal ends of each cartridge pocket (D320) of each row, except for the distalmost cartridge pocket (D320) of each row. In this regard, second pocket extenders (D332) are positioned at or near the distal ends of the distalmost cartridge pockets (D320) of the outer rows, and third pocket extenders (D334) are positioned at or near the distal ends of the distalmost cartridge pockets (D320) of the inner and middle rows such that each third pocket extender (D334) spans laterally across two rows of cartridge pockets (D320) on the respective lateral side of knife slot (D318) (e.g., the respective inner and middle rows of cartridge pockets (D320)).

As shown, each first pocket extender (D330a, D330b) includes a generally U-shaped body (D340a, D340b) that defines a staple leg receptacle (D342a, D342b) for receiving a corresponding leg (D126) of the staple (86) slidably housed within the respective cartridge pocket (D320). In this regard, each staple leg receptacle (D342a, D342b) may be sized and configured to slidably receive the corresponding leg (D126) for vertically guiding the corresponding leg (D126) out of the respective cartridge pocket (D320) toward the corresponding staple forming pockets (66) as staples (86) are driven outwardly from cartridge pockets (D320) by the staple drivers. The body (D340a) of each proximal first pocket extender (D330a) also defines a proximally-facing outer surface (D344a) that extends substantially orthogonally relative to deck (D314), while the body (D340b) of each distal first pocket extender (D330b) also defines a distally-facing outer surface (D344b) that extends substantially orthogonally relative to deck (D314). The body (D340a, D340b) of each first pocket extender (D330a, D330b) further defines an upwardly-facing top surface (D346a, D346b) that extends substantially parallel relative to deck (D314). Top surfaces (D346a, D346b) may be positioned at a substantially uniform height above deck (D314).

Each second pocket extender (D332) includes a generally U-shaped body (D350) that defines a staple leg receptacle (D352) for receiving a corresponding leg (D126) of the staple (86) slidably housed within the respective distalmost, outer cartridge pocket (D320). In this regard, each staple leg receptacle (D352) may be sized and configured to slidably receive the corresponding leg (D126) for vertically guiding the corresponding leg (D126) out of the respective cartridge pocket (D320) toward the corresponding staple forming pockets (66) as staples (86) are driven outwardly from cartridge pockets (D320) by the staple drivers. The body (D350) of each second pocket extender (D332) also defines a distally-facing outer surface (D354) that extends substantially obliquely relative to deck (D314). In the example shown, the outer surface (D354) of each second pocket extender (D332) is rounded in the longitudinal direction. By extending substantially obliquely relative to deck (D314) and/or by being rounded in the longitudinal direction, the outer surface (D354) of each second pocket extender (D332) may have a substantially atraumatic configuration so that each outer surface (D354) may avoid inflicting trauma to tissue contacted by the outer surface (D354). For example, each outer surface (D354) may define a distal ramp for gently lifting such tissue upwardly relative to deck (D314).

The body (D350) of each second pocket extender (D332) further defines an upwardly-facing top surface (D356) that extends substantially parallel relative to deck (D314). Top surfaces (D356) may be positioned at a substantially same height above deck (D314) as that of top surfaces (D346a, D346b). In some other versions, top surfaces (D356) may be positioned at a lower height above deck (D314) than that of top surfaces (D346a, D346b). In the example shown, the top surface (D356) of each second pocket extender (D332) has a surface area that is greater than that of the top surface (D346a, D346b) of each first pocket extender (D330a, D330b). The top surface (D356) of each second pocket extender (D332) may also extend further distally compared to the top surface (D346b) of a distal first pocket extender (D330b) if such a distal first pocket extender (D330b) were substituted for the respective second pocket extender (D332). By having a greater surface area and/or extending further distally compared to the top surface (D346a, D346b) of each first pocket extender (D330a, D330b), the top surface (D356) of each second pocket extender (D332) may be configured to provide improved contact with the adhesive layers or beads (D116, D120, D182, D184, D186, D188) of a corresponding buttress assembly (D110, D112, D160), at least relative to the top surface (D346a, D346b) of each first pocket extender (D330a, D330b). For example, the further distal extension of the top surface (D356) of each second pocket extender (D332) may allow the top surface (D356) to vertically align with more adhesive (D166) at distal end (D172) of buttress body (D164) compared to the top surface (D346b) of a distal first pocket extender (D330b) if such a distal first pocket extender (D330b) were substituted for the respective second pocket extender (D332), and may thereby provide stronger, localized attachment of buttress assembly (D160) at the distal end of staple cartridge (D310).

As noted above, each third pocket extender (D334) spans laterally across the respective inner and middle rows of cartridge pockets (D320), and is positioned at or near the distal ends of the distalmost cartridge pockets (D320) of the respective inner and middle rows. Each third pocket extender (D334) includes a generally L-shaped body (D360) that defines proximal and distal staple leg receptacles (D362a, D362b) for receiving corresponding legs (D126) of the staples (86) slidably housed within the respective distalmost, inner and middle cartridge pockets (D320). In this regard, each staple leg receptacle (D362a, D362b) may be sized and configured to slidably receive the corresponding leg (D126) for vertically guiding the corresponding leg (D126) out of the respective cartridge pocket (D320) toward the corresponding staple forming pockets (66) as staples (86) are driven outwardly from cartridge pockets (D320) by the staple drivers.

The body (D360) of each third pocket extender (D334) also defines a distally-facing outer surface (D364) that extends substantially obliquely relative to deck (D314). In the example shown, the outer surface (D364) of each third pocket extender (D334) is rounded in the longitudinal direction. By extending substantially obliquely relative to deck (D314) and/or by being rounded in the longitudinal direction, the outer surface (D364) of each third pocket extender (D334) may have a substantially atraumatic configuration so that each outer surface (D364) may avoid inflicting trauma to tissue contacted by the outer surface (D364). For example, each outer surface (D364) may define a distal ramp for gently lifting such tissue upwardly relative to deck (D314). Due to the spanning of each third pocket extender (D334) laterally across the respective inner and middle rows of cartridge pockets (D320), each outer surface (D364) may be configured to lift the portions of such tissue that are aligned with both the respective inner and middle rows of cartridge pockets (D320), and to do so substantially simultaneously with the lifting of the portions of such tissue that are aligned with the respective outer row of cartridge pockets (D320) by the outer surface (D354) of the corresponding second pocket extender (D332).

The body (D360) of each third pocket extender (D334) further defines an upwardly-facing top surface (D366) that extends substantially parallel relative to deck (D314). Top surfaces (D366) may be positioned at a substantially same height above deck (D314) as that of top surfaces (D346a, D346b). In some other versions, top surfaces (D366) may be positioned at a lower height above deck (D314) than that of top surfaces (D346a, D346b). In the example shown, the top surface (D366) of each third pocket extender (D334) has a surface area that is greater than that of the top surface (D346a, D346b) of each first pocket extender (D330a, D330b). The top surface (D366) of each third pocket extender (D334) may also extend further distally compared to the top surfaces (D346b) of a pair of distal first pocket extenders (D330b) if such a pair of distal first pocket extenders (D330b) were substituted for the respective third pocket extender (D334). By having a greater surface area and/or extending further distally compared to the top surface (D346a, D346b) of each first pocket extender (D330a, D330b), the top surface (D366) of each third pocket extender (D334) may be configured to provide improved contact with the adhesive layers or beads (D116, D120, D182, D184, D186, D188) of a corresponding buttress assembly (D110, D112, D160), at least relative to the top surface (D346a, D346b) of each first pocket extender (D330a, D330b). For example, the further distal extension of the top surface (D366) of each third pocket extender (D334) may allow the top surface (D366) to vertically align with more adhesive (D166) at distal end (D172) of buttress body (D164) compared to the top surfaces (D346b) of a pair of distal first pocket extenders (D330b) if such a pair of distal first pocket extenders (D330b) were substituted for the respective third pocket extender (D334), and may thereby provide stronger, localized attachment of buttress assembly (D160) at the distal end of staple cartridge (D310).

Due to the spanning of each third pocket extender (D334) laterally across the respective inner and middle rows of cartridge pockets (D320), the surface area of the top surface (D366) of each third pocket extender (D334) may also be greater than that of the top surface (D356) of each second pocket extender (D332). By having a greater surface area compared to the top surface (D356) of each second pocket extender (D332), the top surface (D356) of each second pocket extender (D332) may be configured to provide improved contact with the adhesive layers or beads (D116, D120, D182, D184, D186, D188) of a corresponding buttress assembly (D110, D112, D160), at least relative to the top surface (D356) of each second pocket extender (D332) as well.

While each third pocket extender (D334) is shown spanning laterally across the respective inner and middle rows of cartridge pockets (D320), each third pocket extender (D334) may alternatively span laterally across the respective middle and outer rows of cartridge pockets (D320), and/or may span laterally across all three respective rows of cartridge pockets (D320).

C. Example of Staple Cartridge with Undulating Upper Profile

Figure 13:
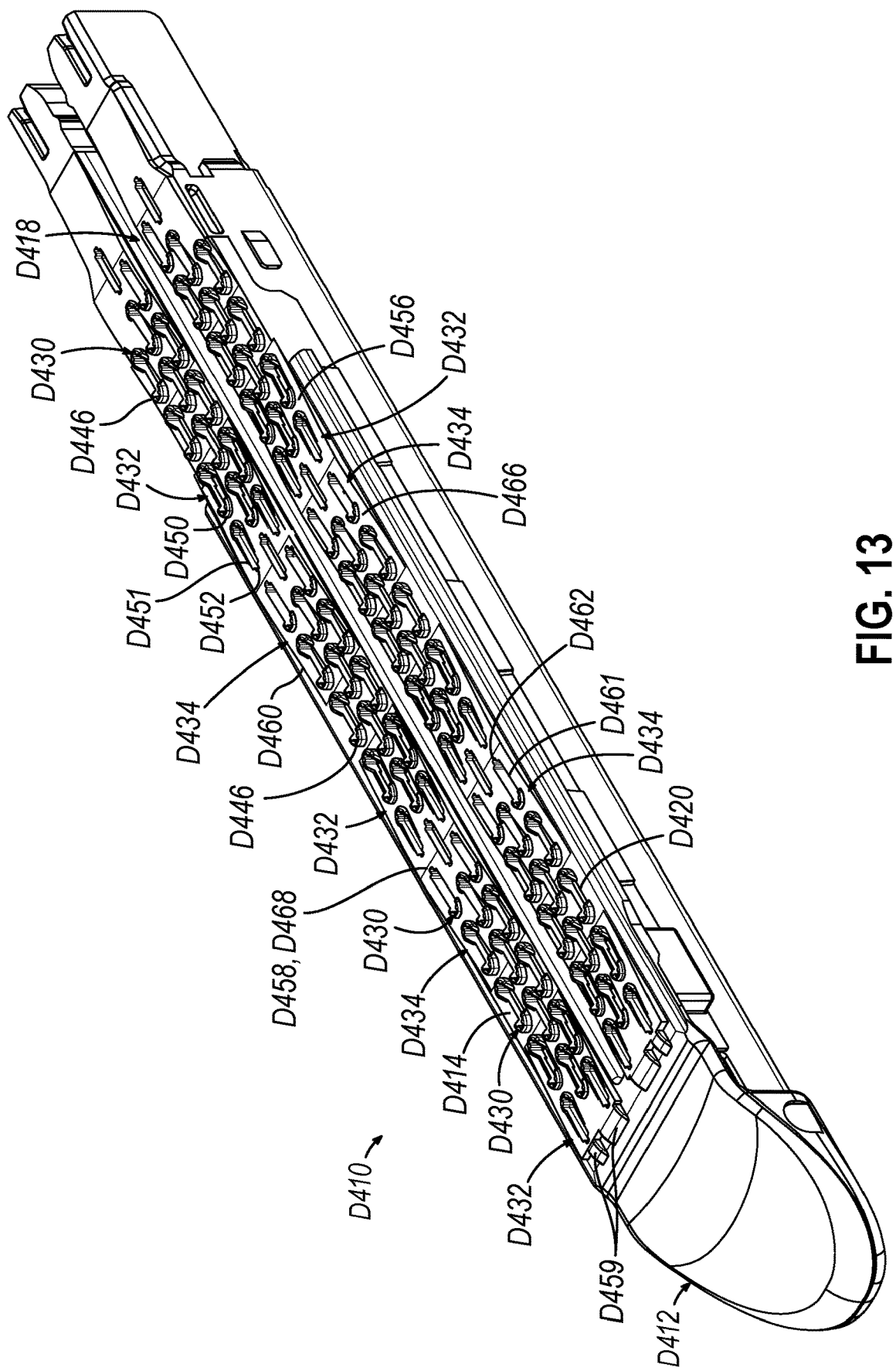
FIG. 13 depicts a perspective view of another example of a staple cartridge for use with the end effector of FIG. 2 and having an undulating upper profile configured to promote adhesion of any of the buttress assemblies of FIGS. 7-10 to the staple cartridge.
Figure 14:
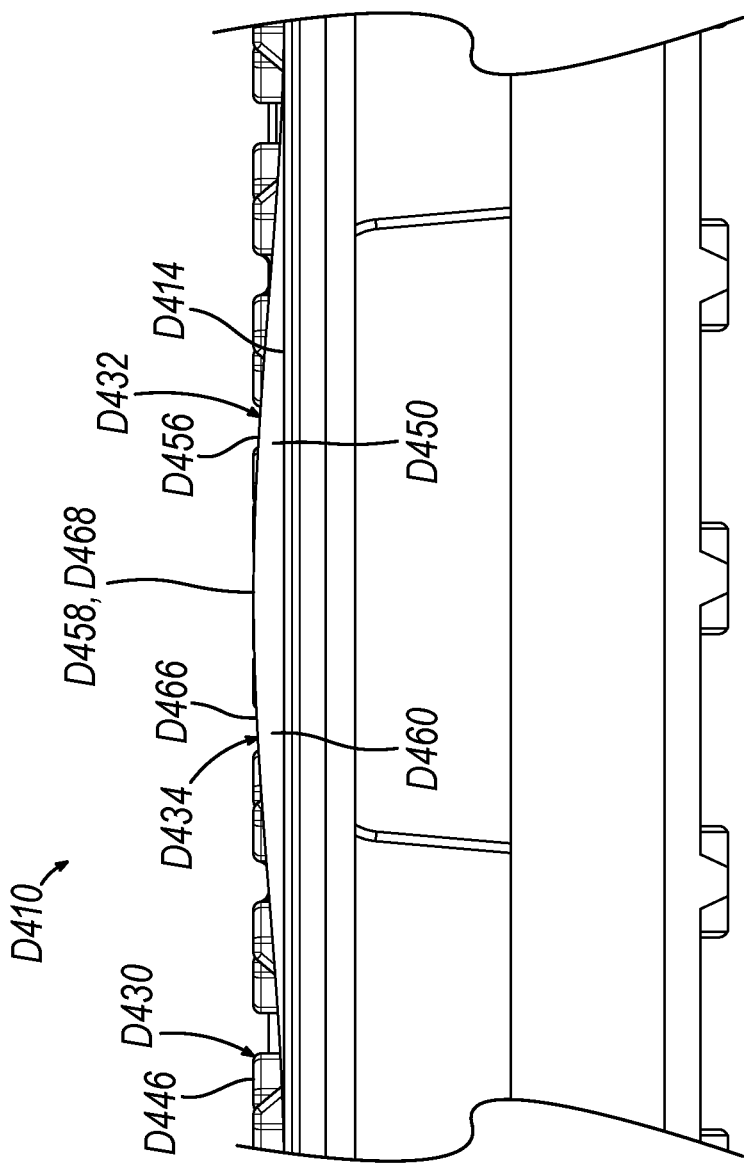
FIG. 14 depicts a partial side elevational view of the staple cartridge of FIG. 13.

FIGS. 13-14 show another example of a staple cartridge (D410) configured to deploy staples (86) toward corresponding staple forming pockets of an anvil (not shown), such as staple forming pockets (66) of anvil (44). Staple cartridge (D410) is configured for use with end effector (40), and is similar to staple cartridge (70) described above except as otherwise described below. In this regard, staple cartridge (D410) of the present example includes a cartridge body (D412) having an upwardly facing deck (D414), an elongate slot (D418) extending along a central axis of cartridge body (D412) and opening upwardly through deck (D414) for slidably receiving a distal knife portion of a firing beam (not shown), such as distal knife portion (50) of firing beam (46), and a plurality of cartridge pockets (D420) extending through deck (D414) on each side of knife slot (D418). In the present version, three longitudinal rows of cartridge pockets (D420) are formed through upper deck (D414) along each lateral side of knife slot (D418), including an inner row, a middle row, and an outer row on each lateral side of knife slot (D418). Each cartridge pocket (D420) slidably houses an unformed staple (86) and a respective staple driver (not shown) similar to staple drivers (84) positioned beneath staple (86). A lower tray (not shown) similar to lower tray (76) encloses an underside of cartridge body (D412) and thereby retains staples (86) and the staple drivers within cartridge body (D412). A wedge sled (not shown) similar to wedge sled (82) is slidably disposed within cartridge body (D412) and includes upwardly presented cam surfaces configured to engage the undersides of the staple drivers.

Staple cartridge (D410) of the present example further includes a plurality of raised features in the form of pocket extenders (D430) that extend upwardly from deck (D414) at or near proximal and distal ends of at least some cartridge pockets (D420), such that at least some cartridge pockets (D420) are each longitudinally flanked by a corresponding pair of proximal and distal pocket extenders (D430) while some other cartridge pockets (D420) are only equipped with either a corresponding proximal or distal pocket extender (D430) and while still other cartridge pockets (D420) may be equipped with neither a corresponding proximal nor distal pocket extender (D430). Any one or more of pocket extenders (D430) may be configured to enhance the gripping of tissue (T1, T2) by staple cartridge (D410) when end effector (40) is closed (e.g., in instances when staple cartridge (D410) is not equipped with a buttress assembly (D110, D112, D160)), and/or to guide the legs (D126) of the staples (86) as the legs (D126) exit the respective cartridge pockets (D420) during deployment of the staples (86). In addition, or alternatively, any one or more of pocket extenders (D430) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D410). As shown, each pocket extender (D430) includes an upwardly-facing top surface (D446) that extends substantially parallel relative to deck (D414). Top surfaces (D446) may be positioned at a substantially uniform height above deck (D414).

Staple cartridge (D410) of the present example also includes a plurality of raised features in the form of first and second wedges (D432, D434) that extend upwardly from deck (D414) on each lateral side of knife slot (D418) such that each wedge (D432, D434) spans laterally across three rows of cartridge pockets (D420) on the respective lateral side of knife slot (D418) (e.g., the respective inner, middle, and outer rows of cartridge pockets (D420)). In the example shown, first and second wedges (D432, D434) are arranged in a longitudinally-alternating manner, such that wedges (D432, D434) cooperate with each other and with deck (D414) to provide staple cartridge (D410) with a generally undulating (e.g., wavy) upper profile when viewed from the side.

Each first wedge (D432) includes a generally triangular body (D450) that defines one or more openings (D451) overlying corresponding cartridge pockets (D420) for accommodating passage of respective staples (86) therethrough. The body (D450) of each first wedge (D432) further defines one or more staple leg receptacles (D452) at or near proximal and distal ends of cartridge pockets (D420) that lack a pocket extender (D430) for receiving a corresponding leg (D126) of the staple (86) slidably housed within the respective cartridge pocket (D420). In this regard, each staple leg receptacle (D452) may be sized and configured to slidably receive the corresponding leg (D126) for vertically guiding the corresponding leg (D126) out of the respective cartridge pocket (D420) toward the corresponding staple forming pockets (66) as staples (86) are driven outwardly from cartridge pockets (D420) by the staple drivers. The body (D450) of each first wedge (D432) also defines an upwardly and/or proximally-facing top surface (D456) that tapers and/or curves upwardly and distally from deck (D414) to a peak (D458). Peaks (D458) may be positioned at a substantially same height above deck (D414) as that of top surfaces (D446). In some other versions, peaks (D458) may be positioned at a lower height above deck (D414) than that of top surfaces (D446).

In the example shown, a pair of atraumatic distal ramps (D459) taper and/or curve upwardly and proximally from deck (D414) to the peak (D458) of each distalmost first wedge (D432) for gently lifting tissue upwardly relative to deck (D414). As shown, at least one such distal ramp (D459) may span laterally at least partially across the respective inner and middle rows of cartridge pockets (D420) for lifting the portions of such tissue that are aligned with both the respective inner and middle rows of cartridge pockets (D420) substantially simultaneously with the lifting of the portions of such tissue that are aligned with the respective outer row of cartridge pockets (D420) via the other distal ramp (D459) on the same lateral side of knife slot (D418).

Each second wedge (D434) includes a generally triangular body (D460) that defines one or more openings (D461) overlying corresponding cartridge pockets (D420) for accommodating passage of respective staples (86) therethrough. The body (D460) of each second wedge (D434) further defines one or more staple leg receptacles (D462) at or near proximal and distal ends of cartridge pockets (D420) that lack a pocket extender (D430) for receiving a corresponding leg (D126) of the staple (86) slidably housed within the respective cartridge pocket (D420). In this regard, each staple leg receptacle (D462) may be sized and configured to slidably receive the corresponding leg (D126) for vertically guiding the corresponding leg (D126) out of the respective cartridge pocket (D420) toward the corresponding staple forming pockets (66) as staples (86) are driven outwardly from cartridge pockets (D420) by the staple drivers. The body (D460) of each second wedge (D434) also defines an upwardly and/or distally-facing top surface (D466) that tapers and/or curves upwardly and proximally from deck (D414) to a peak (D468). In some versions, top surfaces (D466) may be oriented obliquely relative to deck (D414) at a same angle as that at which top surfaces (D456) are oriented obliquely relative to deck (D414). In addition, or alternatively, peaks (D468) may be positioned at a substantially same height above deck (D414) as that of top surfaces (D446). In some other versions, peaks (D468) may be positioned at a lower height above deck (D414) than that of top surfaces (D446).

In the example shown, the peak (D468) of each second wedge (D434) coincides with the peak (D458) of a relatively proximal, longitudinally-adjacent first wedge (D432), while each second wedge (D434) is longitudinally spaced apart from a relatively distal, longitudinally-adjacent first wedge (D432) by a portion of deck (D414) that includes a pair of inner and outer cartridge pockets (D420). In some other versions, the peak (D468) of each second wedge (D434) may be longitudinally spaced apart from the peak (D458) of the relatively proximal, longitudinally-adjacent first wedge (D432) (e.g., by a raised platform extending between the two peaks (D458, D468) and having the same height as both peaks (D458, D468)), and/or each second wedge (D434) may not be longitudinally spaced apart from the relatively distal, longitudinally-adjacent first wedge (D432) (e.g., by directly interfacing with the relatively distal, longitudinally-adjacent first wedge (D432)).

By extending upwardly to peaks (D458, D468) and spanning laterally across the respective three rows of cartridge pockets (D420), the top surfaces (D456, D466) of each wedge (D432, D434) may be configured to provide improved contact with the adhesive layers or beads (D116, D120, D182, D184, D186, D188) of a corresponding buttress assembly (D110, D112, D160), at least relative to the top surface (D446) of each pocket extender (D430). For example, the lateral spanning of each wedge (D432, D434) across the respective three rows of cartridge pockets (D420) may allow each peak (D458, D468) and/or the longitudinally adjacent region(s) of the respective wedge(s) (D432, D434) to contact substantially all of the adhesive (D166) spanning laterally across buttress body (D164) at the corresponding longitudinal position along buttress body (D164), and may thereby provide stronger, localized attachment of buttress assembly (D160) at such longitudinal positions. As a more particular example, the lateral spanning of each distalmost first wedge (D432) across the respective three rows of cartridge pockets (D420) may allow the peak (D458) of each distalmost first wedge (D432) to contact substantially all of the adhesive (D166) spanning laterally across distal end (D172) of buttress body (D164), and may thereby provide stronger, localized attachment of buttress assembly (D160) at the distal end of staple cartridge (D410).

While each wedge (D432, D434) is shown spanning laterally across all three respective rows of cartridge pockets (D420), each wedge (D432, D434) may alternatively span laterally across only the respective inner and middle rows of cartridge pockets (D420), or only the respective middle and outer rows of cartridge pockets (D420).

It will be appreciated that the particular positions of wedges (D432, D434), including the particular positions of peaks (D458, D468), may be selected to achieve both a desired amount of tissue compression and a desired adhesion of a corresponding buttress assembly (D110, D112, D160) to staple cartridge (D410). For example, the particular positions of wedges (D432, D434), including the particular positions of peaks (D458, D468), may be selected to correspond to the position(s) of adhesive (D166) on buttress body (D164) so that wedges (D434, D434) may achieve the desired adhesion of buttress assembly (D160) to staple cartridge (D410) while limiting any increases in tissue compression that might be caused by wedges (D432, D434) to the regions in which wedges (D434, D434) are present.

D. Example of Staple Cartridge with Dome-Shaped Contact Pads

Figure 15:
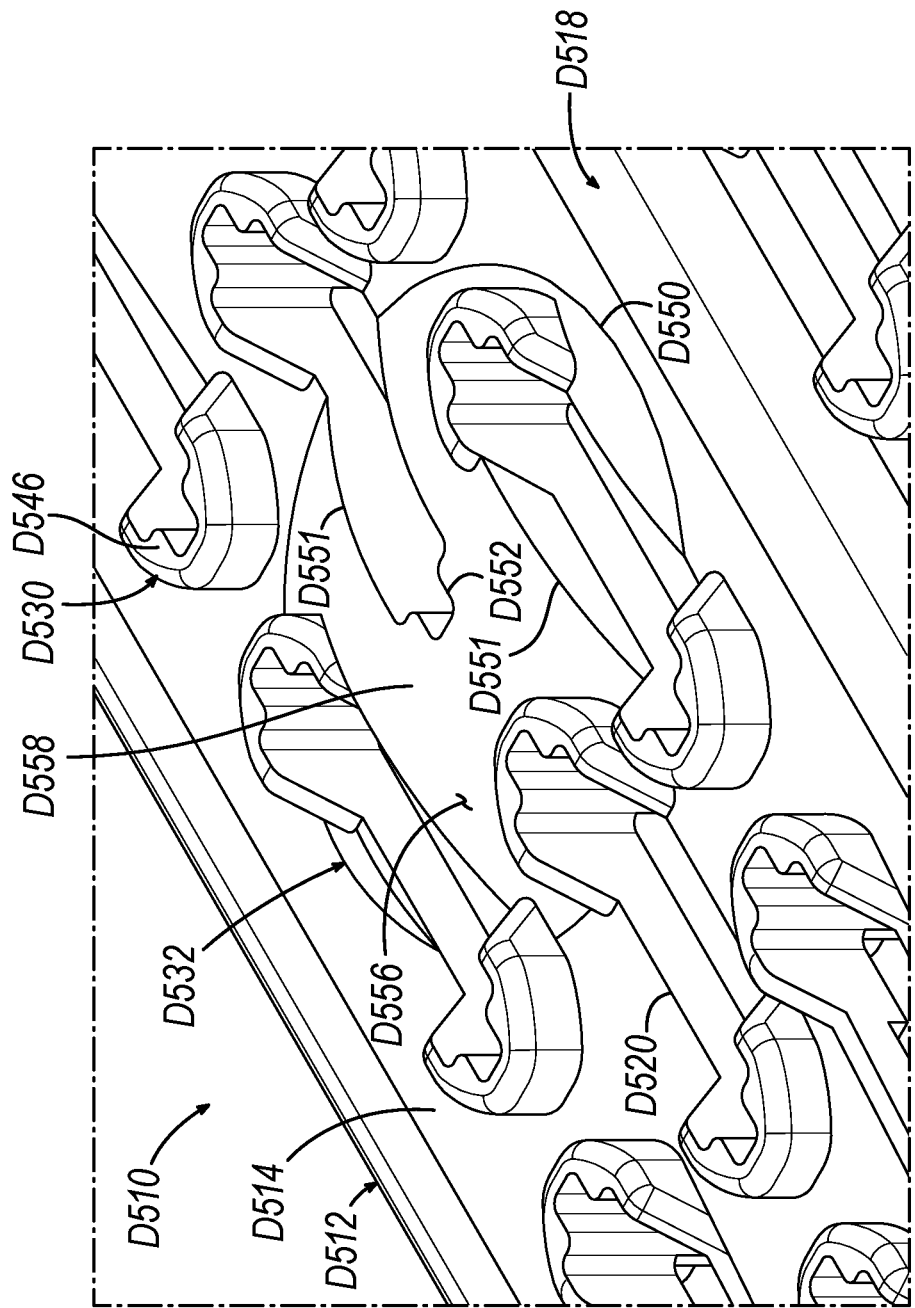
FIG. 15 depicts a partial perspective view of another example of a staple cartridge for use with the end effector of FIG. 2 and having dome-shaped contact pads configured to promote adhesion of any of the buttress assemblies of FIGS. 7-10 to the staple cartridge.

FIG. 15 shows a portion of another example of a staple cartridge (D510) configured to deploy staples (86) toward corresponding staple forming pockets of an anvil (not shown), such as staple forming pockets (66) of anvil (44). Staple cartridge (D510) is configured for use with end effector (40), and is similar to staple cartridge (70) described above except as otherwise described below. In this regard, staple cartridge (D510) of the present example includes a cartridge body (D512) having an upwardly facing deck (D514), an elongate slot (D518) extending along a central axis of cartridge body (D512) and opening upwardly through deck (D514) for slidably receiving a distal knife portion of a firing beam (not shown), such as distal knife portion (50) of firing beam (46), and a plurality of cartridge pockets (D520) extending through deck (D514) on each side of knife slot (D518). In the present version, three longitudinal rows of cartridge pockets (D520) are formed through upper deck (D514) along each lateral side of knife slot (D518), including an inner row, a middle row, and an outer row on each lateral side of knife slot (D518). Each cartridge pocket (D520) slidably houses an unformed staple (86) and a respective staple driver (not shown) similar to staple drivers (84) positioned beneath staple (86). A lower tray (not shown) similar to lower tray (76) encloses an underside of cartridge body (D512) and thereby retains staples (86) and the staple drivers within cartridge body (D512). A wedge sled (not shown) similar to wedge sled (82) is slidably disposed within cartridge body (D512) and includes upwardly presented cam surfaces configured to engage the undersides of the staple drivers.

Staple cartridge (D510) of the present example further includes a plurality of raised features in the form of pocket extenders (D530) that extend upwardly from deck (D514) at or near proximal and distal ends of at least some cartridge pockets (D520), such that at least some cartridge pockets (D520) are each longitudinally flanked by a corresponding pair of proximal and distal pocket extenders (D530) while some other cartridge pockets (D520) are only equipped with either a corresponding proximal or distal pocket extender (D530). Any one or more of pocket extenders (D530) may be configured to enhance the gripping of tissue (T1, T2) by staple cartridge (D510) when end effector (40) is closed (e.g., in instances when staple cartridge (D510) is not equipped with a buttress assembly (D110, D112, D160)), and/or to guide the legs (D126) of the staples (86) as the legs (D126) exit the respective cartridge pockets (D520) during deployment of the staples (86). In addition, or alternatively, any one or more of pocket extenders (D530) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D510). As shown, each pocket extender (D530) includes an upwardly-facing top surface (D546) that extends substantially parallel relative to deck (D514). Top surfaces (D546) may be positioned at a substantially uniform height above deck (D514).

Staple cartridge (D510) of the present example also includes a plurality of raised features in the form of contact pads (D532) that extend upwardly from deck (D514) on each lateral side of knife slot (D518) such that each contact pad (D532) spans laterally across three rows of cartridge pockets (D520) on the respective lateral side of knife slot (D518) (e.g., the respective inner, middle, and outer rows of cartridge pockets (D520)). While only one contact pad (D532) is shown, it will be appreciated that a plurality of contact pads (D532) may be spaced apart from each other along the length of staple cartridge (D510) on each lateral side of knife slot (D518).

Each contact pad (D532) includes a generally dome-shaped body (D550) that defines one or more openings (D551) overlying corresponding cartridge pockets (D520) for accommodating passage of respective staples (86) therethrough. The body (D550) of each contact pad (D532) further defines one or more staple leg receptacles (D552) at or near proximal and distal ends of cartridge pockets (D520) that lack a pocket extender (D530) for receiving a corresponding leg (D126) of the staple (86) slidably housed within the respective cartridge pocket (D520). In this regard, each staple leg receptacle (D552) may be sized and configured to slidably receive the corresponding leg (D126) for vertically guiding the corresponding leg (D126) out of the respective cartridge pocket (D520) toward the corresponding staple forming pockets (66) as staples (86) are driven outwardly from cartridge pockets (D520) by the staple drivers. The body (D550) of each contact pad (D532) also defines an upwardly-facing, hemispherical top surface (D556) that curves upwardly and radially inwardly in a convex manner from deck (D514) to a peak (D558). Peaks (D558) may be positioned at a substantially same height above deck (D514) as that of top surfaces (D546). In some other versions, peaks (D558) may be positioned at a lower height above deck (D514) than that of top surfaces (D546).

By extending upwardly to peaks (D558) and spanning laterally across the respective three rows of cartridge pockets (D520), the top surfaces (D556) of each contact pad (D532) may be configured to provide improved contact with the adhesive layers or beads (D116, D120, D182, D184, D186, D188) of a corresponding buttress assembly (D110, D112, D160), at least relative to the top surface (D546) of each pocket extender (D530). For example, the lateral spanning of each contact pad (D532) across the respective three rows of cartridge pockets (D520) may allow each peak (D558) and/or the longitudinally adjacent region(s) and/or the laterally adjacent region(s) of the respective contact pad(s) (D532) to contact at least a laterally middle region of the adhesive (D166) spanning laterally across buttress body (D164) at the corresponding longitudinal position along buttress body (D164), and may thereby provide stronger, localized attachment of buttress assembly (D160) at such longitudinal positions.

While each contact pad (D532) is shown spanning laterally across all three respective rows of cartridge pockets (D520), each contact pad (D532) may alternatively span laterally across only the respective inner and middle rows of cartridge pockets (D520), or only the respective middle and outer rows of cartridge pockets (D520).

It will be appreciated that the particular positions of contact pads (D532), including the particular positions of peaks (D558), may be selected to achieve both a desired amount of tissue compression and a desired adhesion of a corresponding buttress assembly (D110, D112, D160) to staple cartridge (D510). For example, the particular positions of contact pads (D532), including the particular positions of peaks (D558), may be selected to correspond to the position(s) of adhesive (D166) on buttress body (D164) so that contact pads (D532) may achieve the desired adhesion of buttress assembly (D160) to staple cartridge (D510) while limiting any increases in tissue compression that might be caused by contact pads (D532) to the regions in which contact pads (D532) are present.

E. Example of Staple Cartridge with Tissue-Stabilizing Wedges

Figure 16:
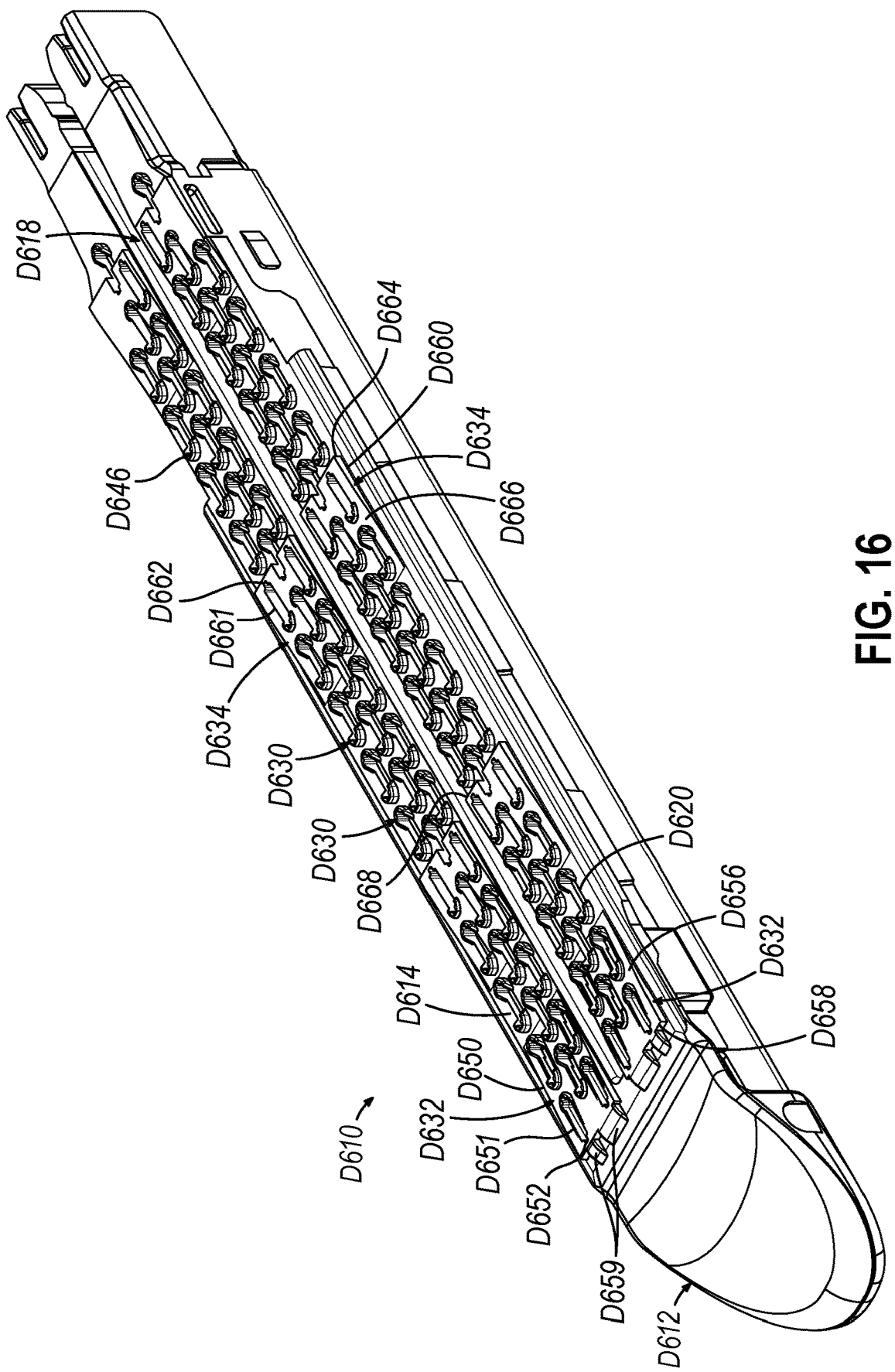
FIG. 16 depicts a perspective view of another example of a staple cartridge for use with the end effector of FIG. 2 and having tissue-stabilizing wedges configured to promote adhesion of any of the buttress assemblies of FIGS. 7-10 to the staple cartridge.
Figure 17:
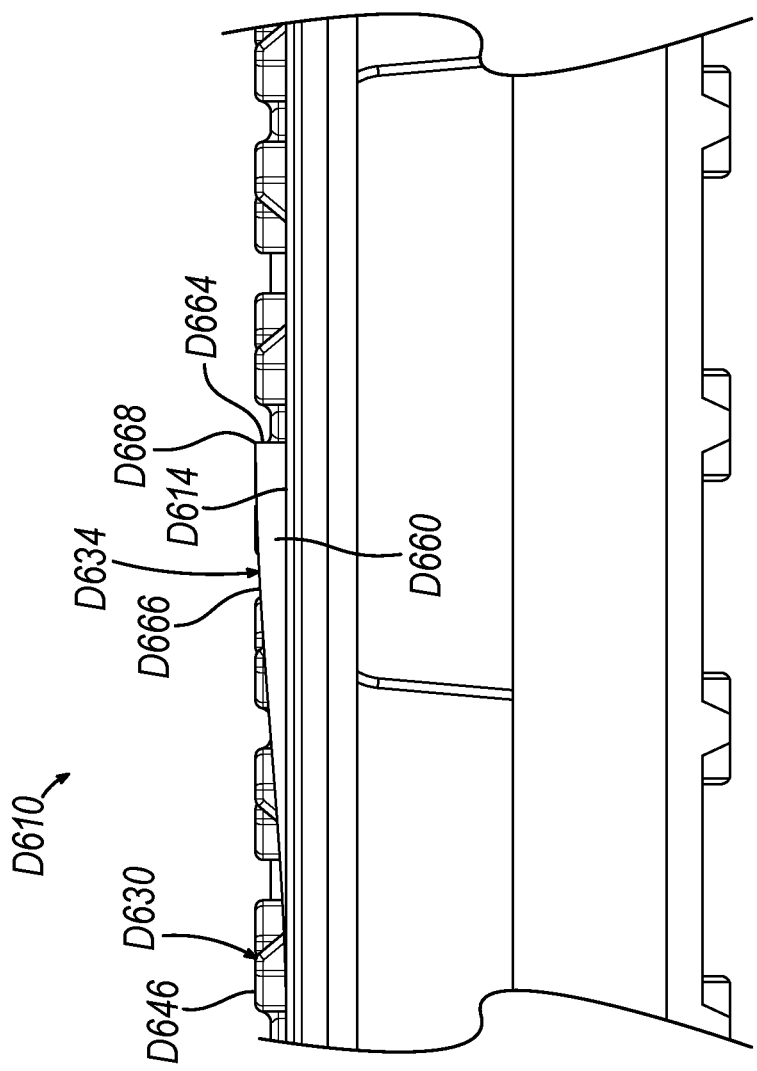
FIG. 17 depicts a partial side elevational view of the staple cartridge of FIG. 16.

FIGS. 16-17 show another example of a staple cartridge (D610) configured to deploy staples (86) toward corresponding staple forming pockets of an anvil (not shown), such as staple forming pockets (66) of anvil (44). Staple cartridge (D610) is configured for use with end effector (40), and is similar to staple cartridge (70) described above except as otherwise described below. In this regard, staple cartridge (D610) of the present example includes a cartridge body (D612) having an upwardly facing deck (D614), an elongate slot (D618) extending along a central axis of cartridge body (D612) and opening upwardly through deck (D614) for slidably receiving a distal knife portion of a firing beam (not shown), such as distal knife portion (50) of firing beam (46), and a plurality of cartridge pockets (D620) extending through deck (D614) on each side of knife slot (D618). In the present version, three longitudinal rows of cartridge pockets (D620) are formed through upper deck (D614) along each lateral side of knife slot (D618), including an inner row, a middle row, and an outer row on each lateral side of knife slot (D618). Each cartridge pocket (D620) slidably houses an unformed staple (86) and a respective staple driver (not shown) similar to staple drivers (84) positioned beneath staple (86). A lower tray (not shown) similar to lower tray (76) encloses an underside of cartridge body (D612) and thereby retains staples (86) and the staple drivers within cartridge body (D612). A wedge sled (not shown) similar to wedge sled (82) is slidably disposed within cartridge body (D612) and includes upwardly presented cam surfaces configured to engage the undersides of the staple drivers.

Staple cartridge (D610) of the present example further includes a plurality of raised features in the form of pocket extenders (D630) that extend upwardly from deck (D614) at or near proximal and distal ends of at least some cartridge pockets (D620), such that at least some cartridge pockets (D620) are each longitudinally flanked by a corresponding pair of proximal and distal pocket extenders (D630) while some other cartridge pockets (D620) are only equipped with either a corresponding proximal or distal pocket extender (D630). Any one or more of pocket extenders (D630) may be configured to enhance the gripping of tissue (T1, T2) by staple cartridge (D610) when end effector (40) is closed (e.g., in instances when staple cartridge (D610) is not equipped with a buttress assembly (D110, D112, D160)), and/or to guide the legs (D126) of the staples (86) as the legs (D126) exit the respective cartridge pockets (D620) during deployment of the staples (86). In addition, or alternatively, any one or more of pocket extenders (D630) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D610). As shown, each pocket extender (D630) includes an upwardly-facing top surface (D646) that extends substantially parallel relative to deck (D614). Top surfaces (D646) may be positioned at a substantially uniform height above deck (D614).

Staple cartridge (D610) of the present example also includes a plurality of raised features in the form of first and second wedges (D632, D634) that extend upwardly from deck (D614) on each lateral side of knife slot (D618) such that each wedge (D632, D634) spans laterally across three rows of cartridge pockets (D620) on the respective lateral side of knife slot (D618) (e.g., the respective inner, middle, and outer rows of cartridge pockets (D620)). In the example shown, first wedges (D632) are arranged at or near the distal end of deck (D614), while second wedges (D634) are each arranged proximally of first wedges (D632).

Each first wedge (D632) includes a generally triangular body (D650) that defines one or more openings (D651) overlying corresponding cartridge pockets (D620) for accommodating passage of respective staples (86) therethrough. The body (D650) of each first wedge (D632) further defines one or more staple leg receptacles (D652) at or near proximal and distal ends of cartridge pockets (D620) that lack a pocket extender (D630) for receiving a corresponding leg (D126) of the staple (86) slidably housed within the respective cartridge pocket (D620). In this regard, each staple leg receptacle (D652) may be sized and configured to slidably receive the corresponding leg (D126) for vertically guiding the corresponding leg (D126) out of the respective cartridge pocket (D620) toward the corresponding staple forming pockets (66) as staples (86) are driven outwardly from cartridge pockets (D620) by the staple drivers. The body (D650) of each first wedge (D632) also defines an upwardly and/or proximally-facing top surface (D656) that tapers and/or curves upwardly and distally from deck (D614) to a peak (D658). Peaks (D658) may be positioned at a substantially same height above deck (D614) as that of top surfaces (D646). In some other versions, peaks (D658) may be positioned at a lower height above deck (D614) than that of top surfaces (D646).

In the example shown, a pair of atraumatic distal ramps (D659) taper and/or curve upwardly and proximally from deck (D614) to the peak (D658) of each first wedge (D632) for gently lifting tissue upwardly relative to deck (D614). As shown, at least one such distal ramp (D659) may span laterally at least partially across the respective inner and middle rows of cartridge pockets (D620) for lifting the portions of such tissue that are aligned with both the respective inner and middle rows of cartridge pockets (D620) substantially simultaneously with the lifting of the portions of such tissue that are aligned with the respective outer row of cartridge pockets (D620) via the other distal ramp (D659) on the same lateral side of knife slot (D618).

Each second wedge (D634) includes a generally triangular body (D660) that defines one or more openings (D661) overlying corresponding cartridge pockets (D620) for accommodating passage of respective staples (86) therethrough. The body (D660) of each second wedge (D634) further defines one or more staple leg receptacles (D662) at or near proximal and distal ends of cartridge pockets (D620) that lack a pocket extender (D630) for receiving a corresponding leg (D126) of the staple (86) slidably housed within the respective cartridge pocket (D620). In this regard, each staple leg receptacle (D662) may be sized and configured to slidably receive the corresponding leg (D126) for vertically guiding the corresponding leg (D126) out of the respective cartridge pocket (D620) toward the corresponding staple forming pockets (66) as staples (86) are driven outwardly from cartridge pockets (D620) by the staple drivers.

The body (D660) of each second wedge (D634) also defines a proximally-facing end surface (D664) that extends substantially orthogonally relative to deck (D614) from deck (D614) to a peak (D668). By extending substantially orthogonally relative to deck (D614), the end surface (D664) of each second wedge (D634) may be configured to stabilize the tissue being severed and stapled, such as by inhibiting movement (e.g., "flow") of the tissue being severed and stapled. For example, the end surface (D664) of each second wedge (D634) may impede such tissue from moving distally during distal translation of firing beam (46) (e.g., during a firing stroke).

The body (D660) of each second wedge (D634) further defines an upwardly and/or distally-facing top surface (D666) that tapers and/or curves upwardly and proximally from deck (D614) to a respective peak (D668). In some versions, top surfaces (D666) may be oriented obliquely relative to deck (D614) at a same angle as that at which top surfaces (D656) are oriented obliquely relative to deck (D614). In addition, or alternatively, peaks (D668) may be positioned at a substantially same height above deck (D614) as that of top surfaces (D646). In some other versions, peaks (D668) may be positioned at a lower height above deck (D614) than that of top surfaces (D646).

In the example shown, each second wedge (D634) is longitudinally spaced apart from the longitudinally-adjacent second wedge(s) (D634) by a portion of deck (D614) that includes three pairs of inner and outer cartridge pockets (D620), while the distalmost second wedges (D634) are longitudinally spaced apart from the respective first wedges (D632) by a portion of deck (D614) that includes one pair of inner and outer cartridge pockets (D620). In some other versions, each second wedge (D634) may not be longitudinally spaced apart from the longitudinally-adjacent second wedge(s) (D634) (e.g., by directly interfacing with the longitudinally-adjacent second wedge(s) (D634)), and/or the distalmost second wedges (D634) may not be longitudinally spaced apart from the respective first wedges (D632) (e.g., by directly interfacing with the respective first wedges (D632)).

By extending upwardly to peaks (D658, D668) and spanning laterally across the respective three rows of cartridge pockets (D620), the top surfaces (D656, D666) of each wedge (D632, D634) may be configured to provide improved contact with the adhesive layers or beads (D116, D120, D182, D184, D186, D188) of a corresponding buttress assembly (D110, D112, D160), at least relative to the top surface (D646) of each pocket extender (D630). For example, the lateral spanning of each wedge (D632, D634) across the respective three rows of cartridge pockets (D620) may allow each peak (D658, D668) and/or the longitudinally adjacent region(s) of the respective wedge(s) (D632, D634) to contact substantially all of the adhesive (D166) spanning laterally across buttress body (D164) at the corresponding longitudinal position along buttress body (D164), and may thereby provide stronger, localized attachment of buttress assembly (D160) at such longitudinal positions. As a more particular example, the lateral spanning of each first wedge (D632) across the respective three rows of cartridge pockets (D620) may allow the peak (D658) of each first wedge (D632) to contact substantially all of the adhesive (D166) spanning laterally across distal end (D172) of buttress body (D164), and may thereby provide stronger, localized attachment of buttress assembly (D160) at the distal end of staple cartridge (D610).

While each wedge (D632, D634) is shown spanning laterally across all three respective rows of cartridge pockets (D620), each wedge (D632, D634) may alternatively span laterally across only the respective inner and middle rows of cartridge pockets (D620), or only the respective middle and outer rows of cartridge pockets (D620).

It will be appreciated that the particular positions of wedges (D632, D634), including the particular positions of peaks (D658, D668), may be selected to achieve both a desired amount of tissue compression and a desired adhesion of a corresponding buttress assembly (D110, D112, D160) to staple cartridge (D610). For example, the particular positions of wedges (D632, D634), including the particular positions of peaks (D658, D668), may be selected to correspond to the position(s) of adhesive (D166) on buttress body (D164) so that wedges (D634, D634) may achieve the desired adhesion of buttress assembly (D160) to staple cartridge (D610) while limiting any increases in tissue compression that might be caused by wedges (D632, D634) to the regions in which wedges (D634, 634) are present.

F. Example of Staple Cartridge with Distal Contact Pads

Figure 18:
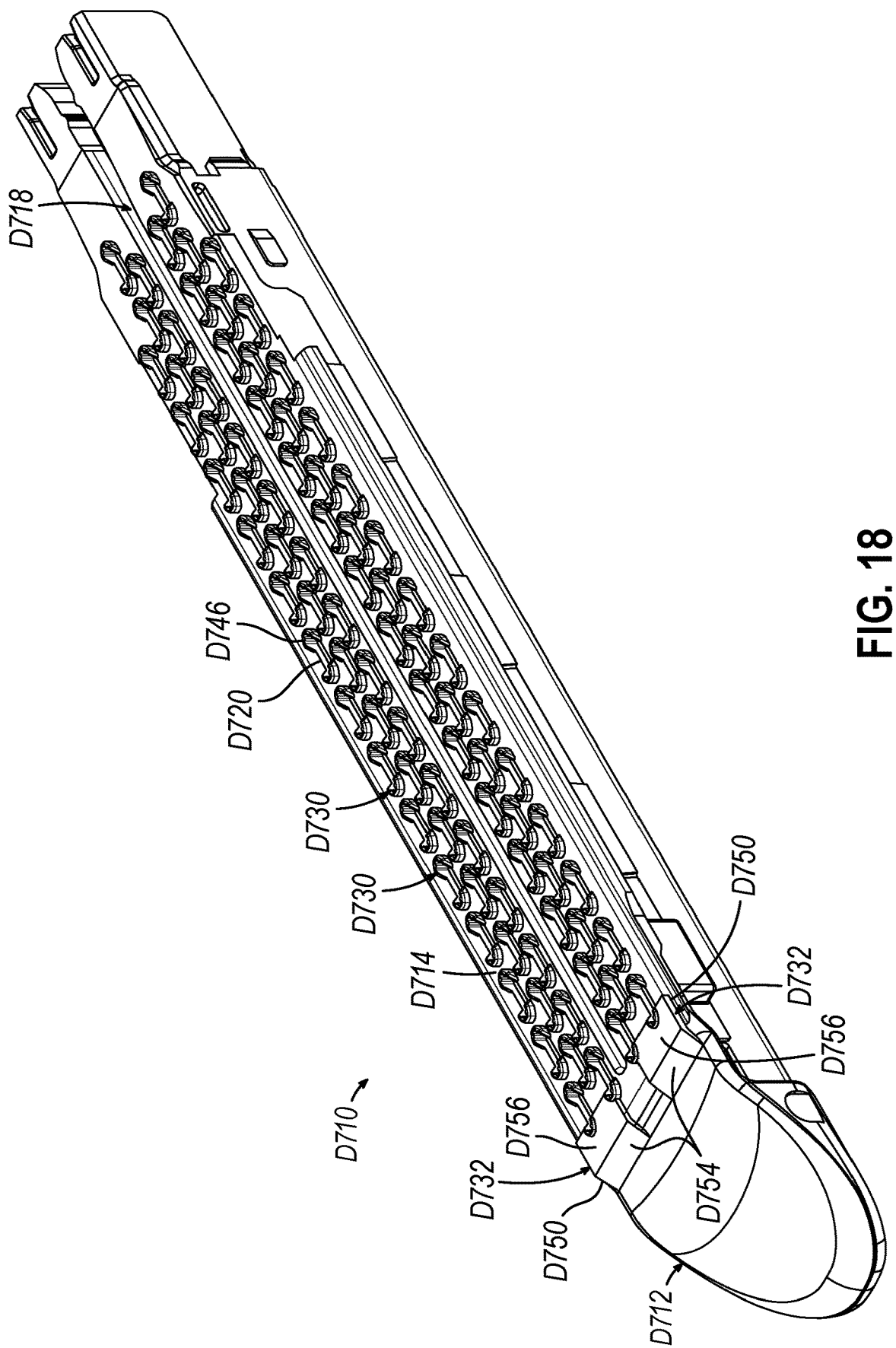
FIG. 18 depicts a perspective view of another example of a staple cartridge for use with the end effector of FIG. 2 and having distal contact pads configured to promote adhesion of any of the buttress assemblies of FIGS. 7-10 to the staple cartridge.

FIGS. 18-20 show another example of a staple cartridge (D710) configured to deploy staples (86) toward corresponding staple forming pockets of an anvil (not shown), such as staple forming pockets (66) of anvil (44). Staple cartridge (D710) is configured for use with end effector (40), and is similar to staple cartridge (70) described above except as otherwise described below. In this regard, staple cartridge (D710) of the present example includes a cartridge body (D712) having an upwardly facing deck (D714), an elongate slot (D718) extending along a central axis of cartridge body (D712) and opening upwardly through deck (D714) for slidably receiving a distal knife portion of a firing beam (not shown), such as distal knife portion (50) of firing beam (46), and a plurality of cartridge pockets (D720) extending through deck (D714) on each side of knife slot (D718). In the present version, three longitudinal rows of cartridge pockets (D720) are formed through upper deck (D714) along each lateral side of knife slot (D718), including an inner row, a middle row, and an outer row on each lateral side of knife slot (D718). Each cartridge pocket (D720) slidably houses an unformed staple (86) and a respective staple driver (not shown) similar to staple drivers (84) positioned beneath staple (86). A lower tray (not shown) similar to lower tray (76) encloses an underside of cartridge body (D712) and thereby retains staples (86) and the staple drivers within cartridge body (D712). A wedge sled (not shown) similar to wedge sled (82) is slidably disposed within cartridge body (D712) and includes upwardly presented cam surfaces configured to engage the undersides of the staple drivers.

Staple cartridge (D710) of the present example further includes a plurality of raised features in the form of pocket extenders (D730) that extend upwardly from deck (D714) at or near proximal and distal ends of each cartridge pocket (D720), such that each cartridge pocket (D720) is longitudinally flanked by a corresponding pair of proximal and distal pocket extenders (D730). Any one or more of pocket extenders (D730) may be configured to enhance the gripping of tissue (T1, T2) by staple cartridge (D710) when end effector (40) is closed (e.g., in instances when staple cartridge (D710) is not equipped with a buttress assembly (D110, D112, D160)), and/or to guide the legs (D126) of the staples (86) as the legs (D126) exit the respective cartridge pockets (D720) during deployment of the staples (86). In addition, or alternatively, any one or more of pocket extenders (D730) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D710). As shown, each pocket extender (D730) includes an upwardly-facing top surface (D746) that extends substantially parallel relative to deck (D714). Top surfaces (D746) may be positioned at a substantially uniform height above deck (D714).

Staple cartridge (D710) of the present example also includes a plurality of raised features in the form of a pair of distal contact pads (D732) that extend upwardly from deck (D714) on each lateral side of knife slot (D718) such that each distal contact pad (D732) spans laterally at least partially across three rows of cartridge pockets (D720) on the respective lateral side of knife slot (D718) (e.g., the respective inner, middle, and outer rows of cartridge pockets (D720)). As shown, distal contact pads (D732) are each positioned at or near the distal end of deck (D714).

Each distal contact pad (D732) includes a generally angled body (D750) that defines a distally-facing end surface (D754) that extends substantially obliquely relative to deck (D714). In the example shown, the end surface (D754) of each distal contact pad (D732) tapers and/or curves downwardly and distally from the distal end of deck (D714). By extending substantially obliquely relative to deck (D714), the end surface (D754) of each distal contact pad (D732) may have a substantially atraumatic configuration so that each end surface (D754) may avoid inflicting trauma to tissue contacted by the end surface (D754). For example, each end surface (D754) may define a distal ramp for gently lifting such tissue upwardly relative to deck (D714). Due to the spanning of each distal contact pad (D732) laterally across the respective inner, middle, and outer rows of cartridge pockets (D720), each end surface (D754) may be configured to lift the portions of such tissue that are aligned with all three respective rows of cartridge pockets (D720).

The body (D750) of each distal contact pad (D732) further defines an upwardly-facing top surface (D756) that extends substantially parallel relative to deck (D714). Top surfaces (D756) may be positioned at a lower height above deck (D714) than that of top surfaces (D746). In some other versions, top surfaces (D756) may be positioned at a substantially same height above deck (D714) as that of top surfaces (D746). In the example shown, the top surface (D756) of each distal contact pad (D732) has a surface area that is greater than that of the top surface (D746) of each pocket extender (D730). The top surface (D756) of each distal contact pad (D732) may also extend further distally compared to the top surface (D746) of the distalmost pocket extenders (D730). By having a greater surface area and/or extending further distally compared to the top surface (D746) of the distalmost pocket extenders (D730), the top surface (D756) of each distal contact pad (D732) may be configured to provide improved contact with the adhesive layers or beads (D116, D120, D182, D184, D186, D188) of a corresponding buttress assembly (D110, D112, D160), at least relative to the top surface (D746) of each pocket extender (D730). For example, the further distal extension of the top surface (D756) of each distal contact pad (D732) may allow the top surface (D756) to vertically align with more adhesive (D166) at distal end (D172) of buttress body (D164) compared to the top surface (D746) of each distalmost pocket extender (D730), and may thereby provide stronger, localized attachment of buttress assembly (D160) at the distal end of staple cartridge (D710).

While each distal contact pad (D732) is shown spanning laterally at least partially across all three respective rows of cartridge pockets (D720), each distal contact pad (D732) may alternatively span laterally at least partially across only the respective inner and middle rows of cartridge pockets (D720), or only the respective middle and outer rows of cartridge pockets (D720).

G. Example of Staple Cartridge with Distal and Proximal Contact Pads

Figure 21:
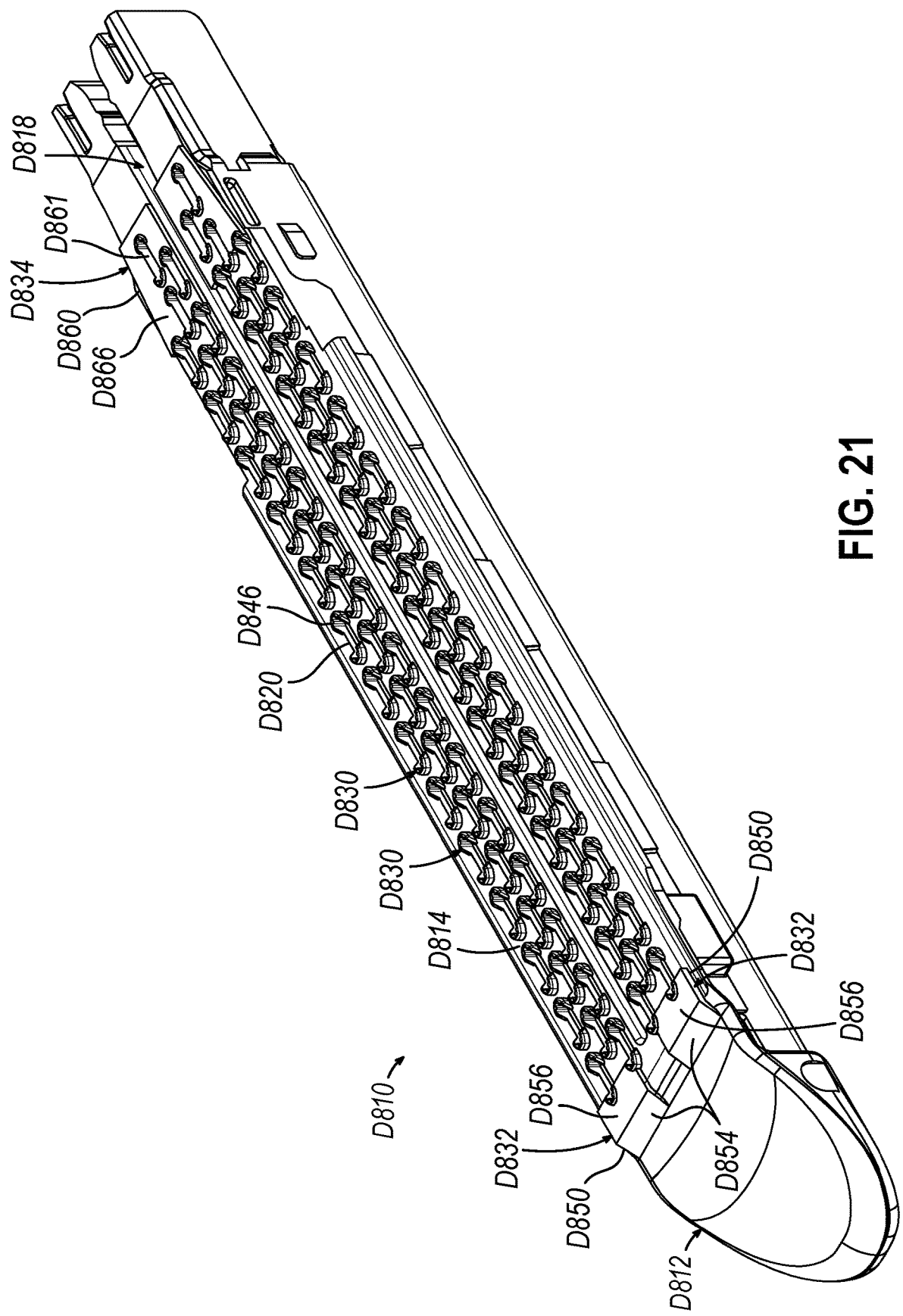
FIG. 21 depicts a perspective view of another example of a staple cartridge for use with the end effector of FIG. 2 and having distal and proximal contact pads configured to promote adhesion of any of the buttress assemblies of FIGS. 7-10 to the staple cartridge.

FIGS. 21-23 show another example of a staple cartridge (D810) configured to deploy staples (86) toward corresponding staple forming pockets of an anvil (not shown), such as staple forming pockets (66) of anvil (44). Staple cartridge (D810) is configured for use with end effector (40), and is similar to staple cartridge (70) described above except as otherwise described below. In this regard, staple cartridge (D810) of the present example includes a cartridge body (D812) having an upwardly facing deck (D814), an elongate slot (D818) extending along a central axis of cartridge body (D812) and opening upwardly through deck (D814) for slidably receiving a distal knife portion of a firing beam (not shown), such as distal knife portion (50) of firing beam (46), and a plurality of cartridge pockets (D820) extending through deck (D814) on each side of knife slot (D818). In the present version, three longitudinal rows of cartridge pockets (D820) are formed through upper deck (D814) along each lateral side of knife slot (D818), including an inner row, a middle row, and an outer row on each lateral side of knife slot (D818). Each cartridge pocket (D820) slidably houses an unformed staple (86) and a respective staple driver (not shown) similar to staple drivers (84) positioned beneath staple (86). A lower tray (not shown) similar to lower tray (76) encloses an underside of cartridge body (D812) and thereby retains staples (86) and the staple drivers within cartridge body (D812). A wedge sled (not shown) similar to wedge sled (82) is slidably disposed within cartridge body (D812) and includes upwardly presented cam surfaces configured to engage the undersides of the staple drivers.

Staple cartridge (D810) of the present example further includes a plurality of raised features in the form of pocket extenders (D830) that extend upwardly from deck (D814) at or near proximal and distal ends of each cartridge pocket (D820), such that each cartridge pocket (D820) is longitudinally flanked by a corresponding pair of proximal and distal pocket extenders (D830). Any one or more of pocket extenders (D830) may be configured to enhance the gripping of tissue (T1, T2) by staple cartridge (D810) when end effector (40) is closed (e.g., in instances when staple cartridge (D810) is not equipped with a buttress assembly (D110, D112, D160)), and/or to guide the legs (D126) of the staples (86) as the legs (D126) exit the respective cartridge pockets (D820) during deployment of the staples (86). In addition, or alternatively, any one or more of pocket extenders (D830) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D810).

As shown, each pocket extender (D830) includes a generally U-shaped body (D840) that defines a staple leg receptacle (D842) for receiving a corresponding leg (D126) of the staple (86) slidably housed within the respective cartridge pocket (D820). In this regard, each staple leg receptacle (D842) may be sized and configured to slidably receive the corresponding leg (D126) for vertically guiding the corresponding leg (D126) out of the respective cartridge pocket (D820) toward the corresponding staple forming pockets (66) as staples (86) are driven outwardly from cartridge pockets (D820) by the staple drivers. The body (D840) of each pocket extender (D830) also defines a proximally-facing or distally-facing outer surface (D844) that extends substantially orthogonally relative to deck (D814). The body (D840) of each first pocket extender (D830) further defines an upwardly-facing top surface (D846) that extends substantially parallel relative to deck (D814). Top surfaces (D846) may be positioned at a substantially uniform height above deck (D814).

Staple cartridge (D810) of the present example also includes a plurality of raised features in the form of pair of distal contact pads (D832) that extend upwardly from deck (D814) on each lateral side of knife slot (D818) such that each distal contact pad (D832) spans laterally at least partially across three rows of cartridge pockets (D820) on the respective lateral side of knife slot (D818) (e.g., the respective inner, middle, and outer rows of cartridge pockets (D820)). As shown, distal contact pads (D832) are each positioned at or near the distal end of deck (D814). Staple cartridge (D810) of the present example also includes another plurality of raised features in the form of a pair of proximal contact pads (D834) that extend upwardly from deck (D814) on each lateral side of knife slot (D818) such that each proximal contact pad (D834) spans laterally at least partially across three rows of cartridge pockets (D820) on the respective lateral side of knife slot (D818) (e.g., the respective inner, middle, and outer rows of cartridge pockets (D820)). As shown, proximal contact pads (D834) are each positioned at or near the proximal end of deck (D814).

Each distal contact pad (D832) includes a generally angled body (D850) that defines a distally-facing end surface (D854) that extends substantially obliquely relative to deck (D814). In the example shown, the end surface (D854) of each distal contact pad (D832) tapers and/or curves downwardly and distally from the distal end of deck (D814). By extending substantially obliquely relative to deck (D814), the end surface (D854) of each distal contact pad (D832) may have a substantially atraumatic configuration so that each end surface (D854) may avoid inflicting trauma to tissue contacted by the end surface (D854). For example, each end surface (D854) may define a distal ramp for gently lifting such tissue upwardly relative to deck (D814). Due to the spanning of each distal contact pad (D832) laterally across the respective inner, middle, and outer rows of cartridge pockets (D820), each end surface (D854) may be configured to lift the portions of such tissue that are aligned with all three respective rows of cartridge pockets (D820).

The body (D850) of each distal contact pad (D832) further defines an upwardly-facing top surface (D856) that extends substantially parallel relative to deck (D814). Top surfaces (D856) may be positioned at a lower height above deck (D814) than that of top surfaces (D846). In some other versions, top surfaces (D856) may be positioned at a substantially same height above deck (D814) as that of top surfaces (D846). In the example shown, the top surface (D856) of each distal contact pad (D832) has a surface area that is greater than that of the top surface (D846) of each pocket extender (D830). The top surface (D856) of each distal contact pad (D832) may also extend further distally compared to the top surface (D846) of the distalmost pocket extenders (D830). By having a greater surface area and/or extending further distally compared to the top surface (D846) of the distalmost pocket extenders (D830), the top surface (D856) of each distal contact pad (D832) may be configured to provide improved contact with the adhesive layers or beads (D116, D120, D182, D184, D186, D188) of a corresponding buttress assembly (D110, D112, D160), at least relative to the top surface (D846) of each pocket extender (D830). For example, the further distal extension of the top surface (D856) of each distal contact pad (D832) may allow the top surface (D856) to vertically align with more adhesive (D166) at distal end (D172) of buttress body (D164) compared to the top surface (D846) of each distalmost pocket extender (D830), and may thereby provide stronger, localized attachment of buttress assembly (D160) at the distal end of staple cartridge (D810).

Each proximal contact pad (D834) includes a generally planar body (D860) that defines one or more openings (D861) overlying corresponding cartridge pockets (D820) for accommodating passage of respective staples (86) therethrough. The body (D860) of each proximal contact pad (D834) also defines an upwardly-facing top surface (D866) that extends substantially parallel relative to deck (D814). Top surfaces (D866) may be positioned at a lower height above deck (D814) than that of top surfaces (D846). In some other versions, top surfaces (D866) may be positioned at a substantially same height above deck (D814) as that of top surfaces (D846). In addition, or alternatively, top surfaces (D866) may be positioned at a substantially same height above deck (D814) as that of top surfaces (D856). In the example shown, the top surface (D866) of each proximal contact pad (D834) has a surface area that is greater than that of the top surface (D846) of each pocket extender (D830). The top surface (D866) of each proximal contact pad (D834) may also extend further proximally compared to the top surface (D846) of the proximal-most pocket extenders (D830). By having a greater surface area and/or extending further proximally compared to the top surface (D846) of the proximal-most pocket extenders (D830), the top surface (D866) of each proximal contact pad (D834) may be configured to provide improved contact with the adhesive layers or beads (D116, D120, D182, D184, D186, D188) of a corresponding buttress assembly (D110, D112, D160), at least relative to the top surface (D846) of each pocket extender (D830). For example, the further proximal extension of the top surface (D866) of each proximal contact pad (D834) may allow the top surface (D866) to vertically align with more adhesive (D166) at proximal end (D170) of buttress body (D164) compared to the top surface (D846) of each proximal-most pocket extender (D830), and may thereby provide stronger, localized attachment of buttress assembly (D160) at the proximal end of staple cartridge (D810).

While each contact pad (D832, D834) is shown spanning laterally at least partially across all three respective rows of cartridge pockets (D820), each contact pad (D832, D834) may alternatively span laterally at least partially across only the respective inner and middle rows of cartridge pockets (D820), or only the respective middle and outer rows of cartridge pockets (D820).

H. Example of Staple Cartridge with Adhesive Pattern-Shaped Contact Pads

FIGS. 24-27 show another example of a staple cartridge (D910) configured to deploy staples (86) toward corresponding staple forming pockets of an anvil (not shown), such as staple forming pockets (66) of anvil (44). Staple cartridge (D910) is configured for use with end effector (40), and is similar to staple cartridge (70) described above except as otherwise described below. In this regard, staple cartridge (D910) of the present example includes a cartridge body (D912) having an upwardly facing deck (D914), an elongate slot (D918) extending along a central axis of cartridge body (D912) and opening upwardly through deck (D914) for slidably receiving a distal knife portion of a firing beam (not shown), such as distal knife portion (50) of firing beam (46), and a plurality of cartridge pockets (D920) extending through deck (D914) on each side of knife slot (D918). In the present version, three longitudinal rows of cartridge pockets (D920) are formed through upper deck (D914) along each lateral side of knife slot (D918), including an inner row, a middle row, and an outer row on each lateral side of knife slot (D918). Each cartridge pocket (D920) slidably houses an unformed staple (86) and a respective staple driver (not shown) similar to staple drivers (84) positioned beneath staple (86). A lower tray (not shown)

similar to lower tray (76) encloses an underside of cartridge body (D912) and thereby retains staples (86) and the staple drivers within cartridge body (D912). A wedge sled (not shown) similar to wedge sled (82) is slidably disposed within cartridge body (D912) and includes upwardly presented cam surfaces configured to engage the undersides of the staple drivers.

Figure 27:
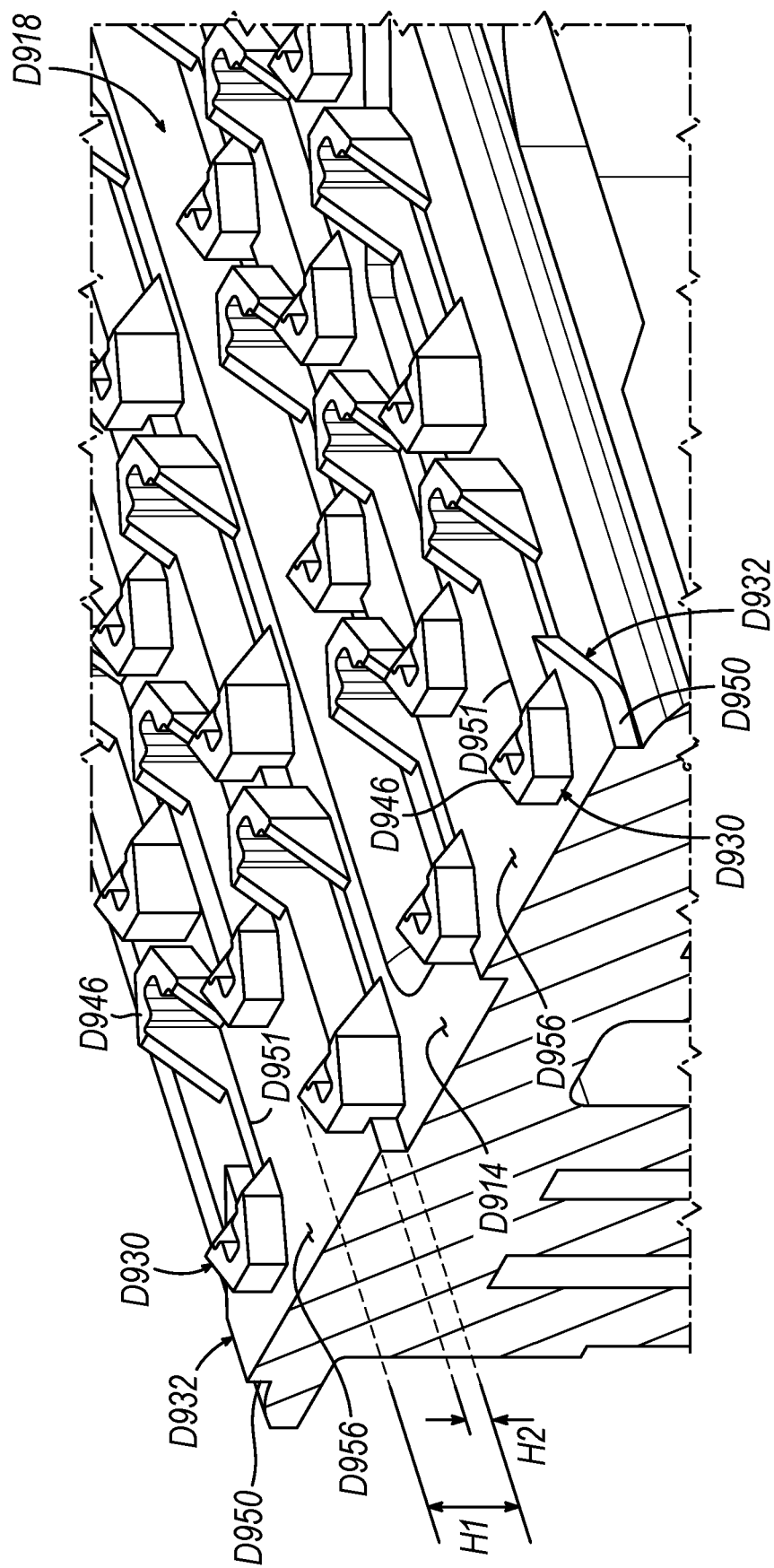
FIG. 27 depicts a partial perspective view of the staple cartridge of FIG. 24.

Staple cartridge (D910) of the present example further includes a plurality of raised features in the form of pocket extenders (D930) that extend upwardly from deck (D914) at or near proximal and distal ends of each cartridge pocket (D920), such that each cartridge pocket (D920) is longitudinally flanked by a corresponding pair of proximal and distal pocket extenders (D930). Any one or more of pocket extenders (D930) may be configured to enhance the gripping of tissue (T1, T2) by staple cartridge (D910) when end effector (40) is closed (e.g., in instances when staple cartridge (D910) is not equipped with a buttress assembly (D110, D112, D160)), and/or to guide the legs (D126) of the staples (86) as the legs (D126) exit the respective cartridge pockets (D920) during deployment of the staples (86). In addition, or alternatively, any one or more of pocket extenders (D930) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D910). As shown, each pocket extender (D930) includes an upwardly-facing top surface (D946) that extends substantially parallel relative to deck (D914). Top surfaces (D946) may be positioned at a substantially uniform first height (H1) above deck (D914), as shown in FIG. 27.

Staple cartridge (D910) of the present example also includes a plurality of raised features in the form of a pair of elongate contact pads (D932) that extend upwardly from deck (D914) on each lateral side of knife slot (D918) such that each contact pad (D932) spans laterally at least partially across three rows of cartridge pockets (D920) on the respective lateral side of knife slot (D918) (e.g., the respective inner, middle, and outer rows of cartridge pockets (D920)).

Figure 24:
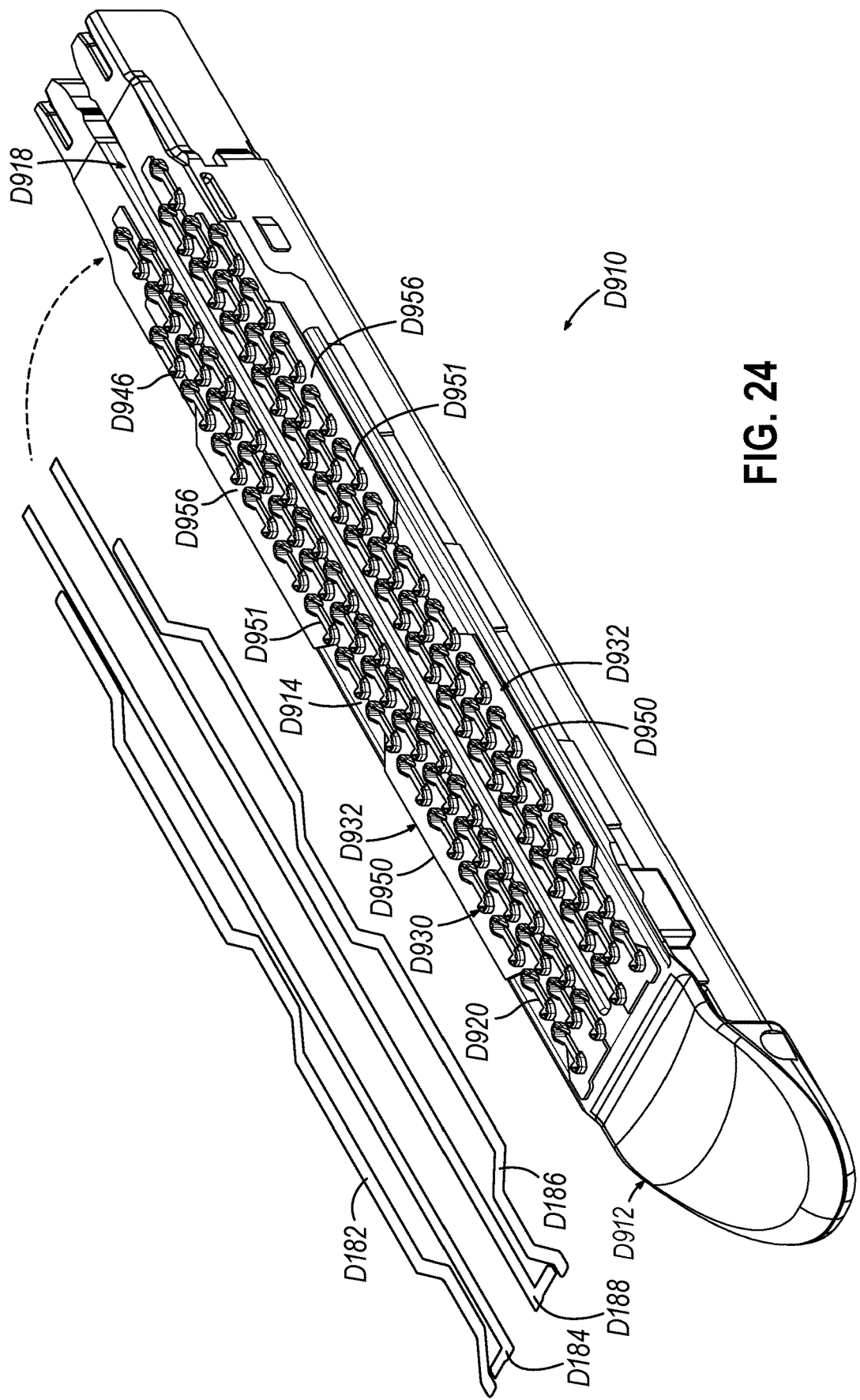
FIG. 24 depicts a perspective view of another example of a staple cartridge for use with the end effector of FIG. 2 and having adhesive pattern-shaped contact pads configured to promote adhesion of any of the buttress assemblies of FIGS. 7-10 to the staple cartridge.
Figure 25:
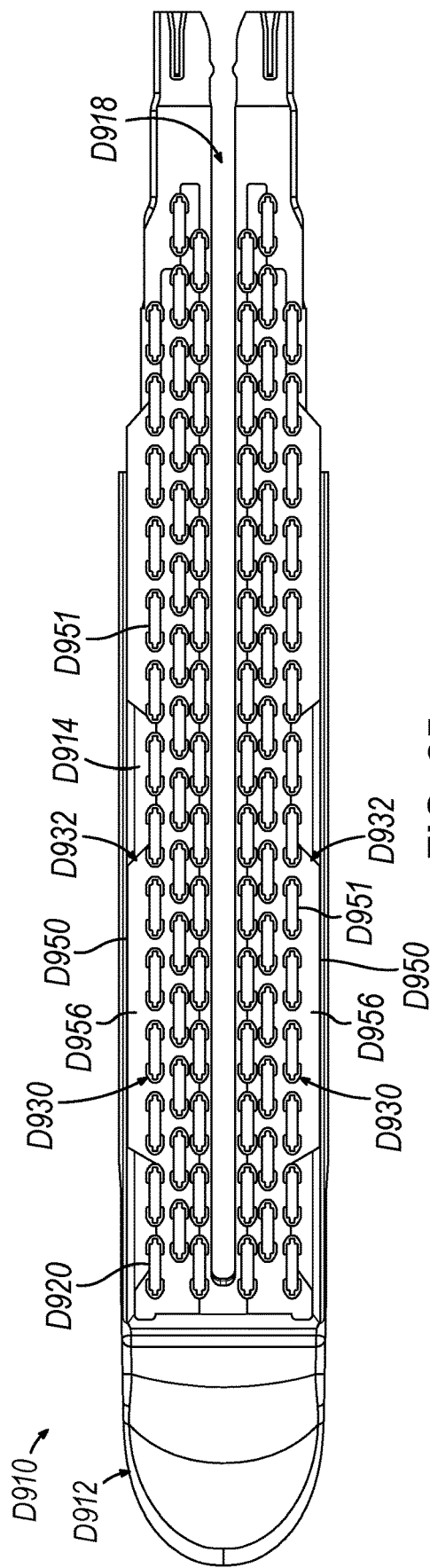
FIG. 25 depicts a top plan view of the staple cartridge of FIG. 24.
Figure 26:
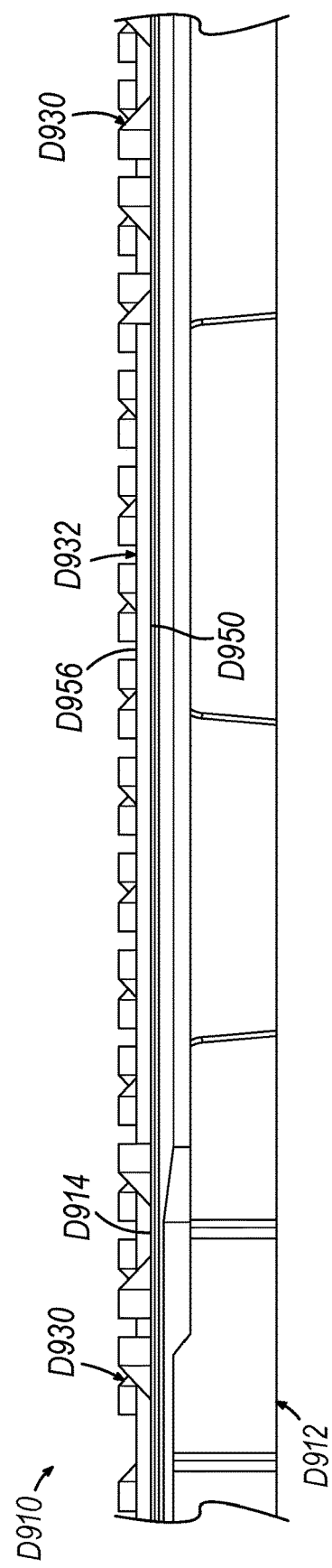
FIG. 26 depicts a side elevational view of the staple cartridge of FIG. 24.

Each contact pad (D932) includes a generally adhesive pattern-shaped body (D950). More particularly, the body (D950) of each contact pad (D932) is shaped to substantially match the pattern of adhesive (D166) of buttress assembly (D160). For example, the outer periphery of each body (D950) may substantially track the outer periphery of the corresponding adhesive beads (D182, D184, D186, D188), such that substantially all of adhesive (D166) may fit within a horizontal envelope defined by the outer periphery of the respective body (D950), as shown in FIG. 24. The body (D950) of each contact pad (D932) defines a plurality of openings (D951) overlying corresponding cartridge pockets (D920) for accommodating passage of respective staples (86) therethrough.

The body (D950) of each contact pad (D932) also defines an upwardly-facing top surface (D956) that extends substantially parallel relative to deck (D914). As shown in FIG. 27, top surfaces (D956) may be positioned at a second height (H2) above deck (D914) that is lower than the first height (H1) of top surfaces (D946). In some other versions, top surfaces (D956) may be positioned at a substantially same height above deck (D914) as that of top surfaces (D946). In the example shown, the top surface (D956) of each contact pad (D932) has a surface area that is greater than that of the top surface (D946) of each pocket extender (D930). The top surface (D956) of each contact pad (D932) may also extend further distally compared to the top surface (D946) of the distalmost pocket extenders (D930), further proximally compared to the top surface (D946) of the proximal-most pocket extenders (D930), and/or further laterally outwardly relative to the central axis of cartridge body (D912) compared to the top surface (D946) of the outer pocket extenders (D930). By having a greater surface area, extending further distally compared to the top surface (D946) of the distalmost pocket extenders (D930), extending further proximally compared to the top surface (D946) of the proximal-most pocket extenders (D930), and/or extending further laterally outwardly compared to the top surface (D946) of the outer pocket extenders (D930), the top surface (D956) of each contact pad (D932) may be configured to provide improved contact with the adhesive layers or beads (D116, D120, D182, D184, D186, D188) of a corresponding buttress assembly (D110, D112, D160), at least relative to the top surface (D946) of each pocket extender (D930). For example, the further distal extension of the top surface (D956) of each contact pad (D932) may allow the top surface (D956) to vertically align with more adhesive (D166) at distal end (D172) of buttress body (D164) compared to the top surface (D946) of each distalmost pocket extender (D930), and may thereby provide stronger, localized attachment of buttress assembly (D160) at the distal end of staple cartridge (D910).

It will also be appreciated that the adhesive-pattern shape of the body (D950) of each contact pad (D932) may allow the top surface (D956) of each contact pad (D932) to vertically align with substantially all of the adhesive (D166) along the entire length of buttress assembly (D160), and may thereby provide stronger attachment of buttress assembly (D160) along the entire length of staple cartridge (D910).

While the shape of the body (D950) of each contact pad (D932) is based on the pattern of adhesive (D166) of buttress assembly (D160), it will be appreciated that contact pads (D932) may also provide improved attachment of other types of buttress assemblies, such as buttress assemblies (D110, D112), to staple cartridge (D910). It will also be appreciated that the shape of the body (D950) of each contact pad (D932) may be based on the pattern of adhesive of any other buttress assembly desired to be attached to staple cartridge (D910).

IV. EXAMPLES OF CARTRIDGES HAVING DISTAL RAISED GRIPPING FEATURES

Figure 28:
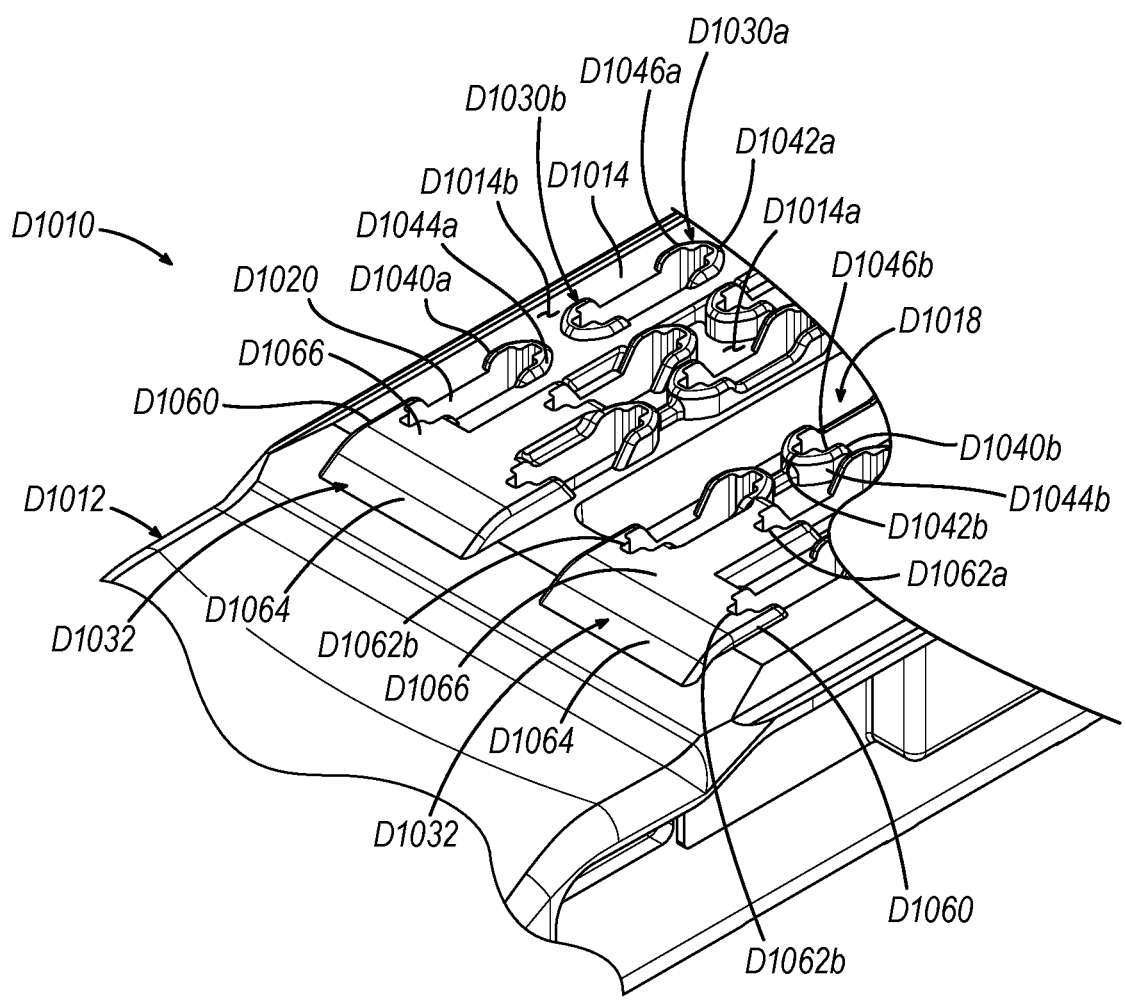
FIG. 28 depicts a partial perspective view of another example of a staple cartridge for use with the end effector of FIG. 2 and having distal raised gripping features that each span across three rows of pockets.

A. Example of Staple Cartridge with Distal Raised Gripping Feature Spanning Across Three Rows of Pockets FIG. 28 shows another example of a staple cartridge (D1010) configured to deploy staples (86) toward corresponding staple forming pockets of an anvil (not shown), such as staple forming pockets (66) of anvil (44). Staple cartridge (D1010) is configured for use with end effector (40), and is similar to staple cartridge (70) described above except as otherwise described below. In this regard, staple cartridge (D1010) of the present example includes a cartridge body (D1012) having an upwardly facing, multi-level deck (D1014), an elongate slot (D1018) extending along a central axis of cartridge body (D1012) and opening upwardly through deck (D1014) for slidably receiving a distal knife portion of a firing beam (not shown), such as distal knife portion (50) of firing beam (46), and a plurality of cartridge pockets (D1020) extending through deck (D1014) on each side of knife slot (D1018). In the present version, three longitudinal rows of cartridge pockets (D1020) are formed through upper deck (D1014) along each lateral side of knife slot (D1018), including an inner row, a middle row, and an outer row on each lateral side of knife slot (D1018). Each cartridge pocket (D1020) slidably houses an unformed staple (86) and a respective staple driver (not shown) similar to staple drivers (84) positioned beneath staple (86). A lower tray (not shown) similar to lower tray (76) encloses an underside of cartridge body (D1012) and thereby retains staples (86) and the staple drivers within cartridge body (D1012). A wedge sled (not shown) similar to wedge sled (82) is slidably disposed within cartridge body (D1012) and includes upwardly presented cam surfaces configured to engage the undersides of the staple drivers.

Multi-level deck (D1014) of the present example includes a lower deck surface (D1014a) spanning across at least the inner and middle rows of cartridge pockets (D1020) on each lateral side of knife slot (D1018), and an upper deck surface (D1014b) provided along at least a distal region of the outer row of cartridge pockets (D1020) on each lateral side of knife slot (D1018).

Staple cartridge (D1010) of the present example further includes a plurality of raised features in the form of pocket extenders (D1030a, D1030b, D1032) that extend upwardly from deck (D1014) at or near proximal and distal ends of each cartridge pocket (D1020), such that each cartridge pocket (D1020) is longitudinally flanked by a corresponding pair of proximal and distal pocket extenders (D1030a, D1030b, D1032). Any one or more of pocket extenders (D1030a, D1030b, D1032) may be configured to enhance the gripping of tissue (T1, T2) by staple cartridge (D1010) when end effector (40) is closed (e.g., in instances when staple cartridge (D1010) is not equipped with a buttress assembly (D110, D112, D160)), and/or to guide the legs (D126) of the staples (86) as the legs (D126) exit the respective cartridge pockets (D1020) during deployment of the staples (86). In addition, or alternatively, any one or more of pocket extenders (D1030a, D1030b, D1032) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1010).

In the example shown, the plurality of pocket extenders (D1030a, D1030b, D1032) include a plurality of first pocket extenders (D1030a, D1030b) having a first configuration, and a plurality of second pocket extenders (D1032) having a second configuration different from the first configuration. First pocket extenders (D1030a, D1030b) include proximal first pocket extenders (D1030a) that are positioned at or near the proximal ends of each cartridge pocket (D1020) of each row, and further include distal first pocket extenders (D1030b) that are positioned at or near the distal ends of each cartridge pocket (D1020) of each row, except for the distalmost cartridge pocket (D1020) of each row. In this regard, second pocket extenders (D1032) are positioned at or near the distal ends of the distalmost cartridge pockets (D1020) of the inner, middle, and outer rows such that each second pocket extender (D1032) spans laterally across three rows of cartridge pockets (D1020) on the respective lateral side of knife slot (D1018) (e.g., the respective inner, middle, and outer rows of cartridge pockets (D1020)).

As shown, each first pocket extender (D1030a, D1030b) includes a generally U-shaped body (D1040a, D1040b) that defines a staple leg receptacle (D1042a, D1042b) for receiving a corresponding leg (D126) of the staple (86) slidably housed within the respective cartridge pocket (D1020). In this regard, each staple leg receptacle (D1042a, D1042b) may be sized and configured to slidably receive the corresponding leg (D126) for vertically guiding the corresponding leg (D126) out of the respective cartridge pocket (D1020) toward the corresponding staple forming pockets (66) as staples (86) are driven outwardly from cartridge pockets (D1020) by the staple drivers. The body (D1040a) of each proximal first pocket extender (D1030a) also defines a proximally-facing outer surface (D1044a) that extends substantially orthogonally relative to deck (D1014), while the body (D1040b) of each distal first pocket extender (D1030b) also defines a distally-facing outer surface (D1044b) that extends substantially orthogonally relative to deck (D1014). The body (D1040a, D1040b) of each first pocket extender (D1030a, D1030b) further defines an upwardly-facing top surface (D1046a, D1046b) that extends substantially parallel relative to deck (D1014). Top surfaces (D1046a, D1046b) may be positioned at a substantially uniform height above a reference surface of deck (D1014) (e.g., either deck surface (D1014a, D1014b)).

As noted above, each second pocket extender (D1032) spans laterally across the respective inner, middle, and outer rows of cartridge pockets (D1020), and is positioned at or near the distal ends of the distalmost cartridge pockets (D1020) of the respective inner, middle, and outer rows. Each second pocket extender (D1032) includes a generally T-shaped body (D1060) that defines one proximal and a pair of distal staple leg receptacles (D1062a, D1062b) for receiving corresponding legs (D126) of the staples (86) slidably housed within the respective distalmost inner, middle, and outer cartridge pockets (D1020). In this regard, each staple leg receptacle (D1062a, D1062b) may be sized and configured to slidably receive the corresponding leg (D126) for vertically guiding the corresponding leg (D126) out of the respective cartridge pocket (D1020) toward the corresponding staple forming pockets (66) as staples (86) are driven outwardly from cartridge pockets (D1020) by the staple drivers.

The body (D1060) of each second pocket extender (D1032) also defines a distally-facing outer surface (D1064) that extends substantially obliquely relative to deck (D1014). In the example shown, the outer surface (D1064) of each second pocket extender (D1032) is rounded in the longitudinal direction. In addition, or alternatively, the outer surface (D1064) of each second pocket extender (D1032) may be rounded in the lateral direction, such as in a manner similar to that shown and described above in connection with FIG. 11. By extending substantially obliquely relative to deck (D1014) and/or by being rounded in the longitudinal and/or lateral direction, the outer surface (D1064) of each second pocket extender (D1032) may have a substantially atraumatic configuration so that each outer surface (D1064) may avoid inflicting trauma to tissue contacted by the outer surface (D1064). For example, each outer surface (D1064) may define a distal ramp for gently lifting such tissue upwardly relative to deck (D1014). Due to the spanning of each second pocket extender (D1032) laterally across the respective inner, middle, and outer rows of cartridge pockets (D1020), each outer surface (D1064) may be configured to lift the portions of such tissue that are aligned with the respective inner, middle, and outer rows of cartridge pockets (D1020).

The body (D1060) of each second pocket extender (D1032) further defines an upwardly-facing top surface (D1066) that extends substantially parallel relative to a reference surface of deck (D1014) (e.g., either deck surface (D1014a, D1014b)). Top surfaces (D1066) may be positioned above upper deck surface (D1014b), and/or at a substantially same height above lower deck surface (D1014a) as that of top surfaces (D1046a, D1046b). In some other versions, top surfaces (D1066) may be positioned at a different height above lower deck surface (D1014a) from that of top surfaces (D1046a, D1046b).

Due to the spanning of each second pocket extender (D1032) laterally across the respective inner, middle, and outer rows of cartridge pockets (D1020), the outer surface (1064) and top surface (D1066) of each second pocket extender (D1032) may provide a continuous interaction anti-snag surface to provide improved lifting of tissue without snagging such tissue. By having a different profile from that of first pocket extenders (D1030a, 1030b), second pocket extenders (D1032) may prevent inadvertent excessive tissue holding while still maintaining a desired degree of tissue gripping.

Figure 29:
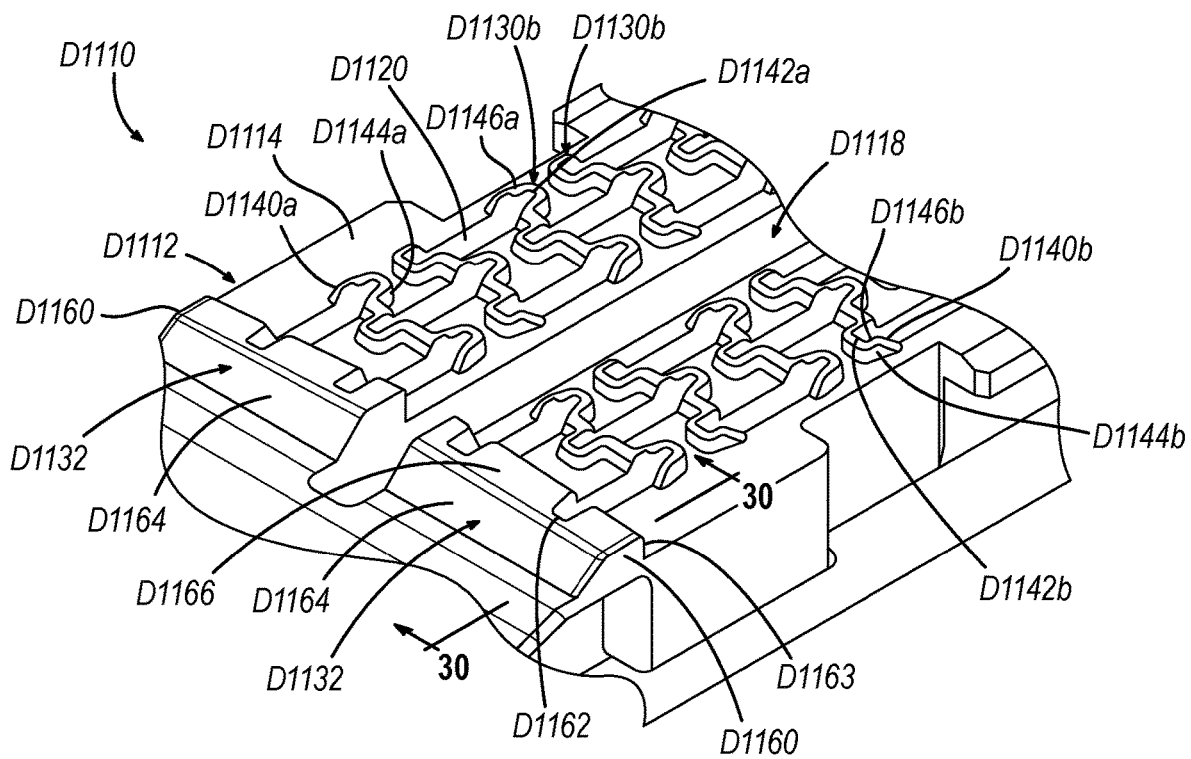
FIG. 29 depicts a partial perspective view of another example of a staple cartridge for use with the end effector of FIG. 2 and having distal raised gripping features that are ramped in multiple directions.
Figure 30:
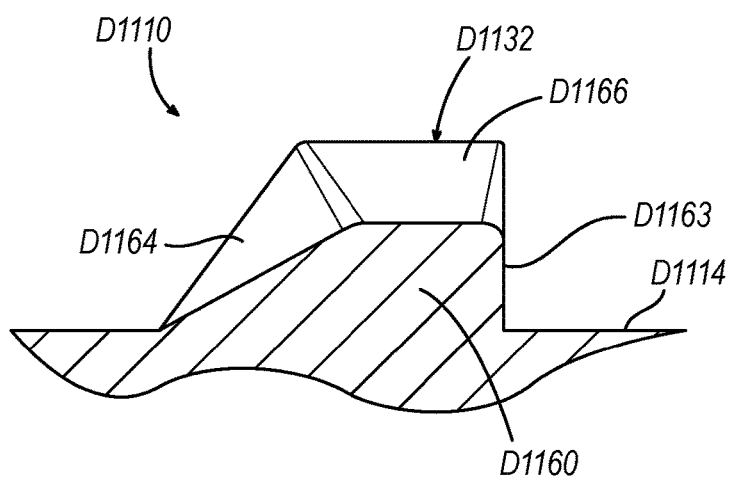
FIG. 30 depicts a cross-sectional view of the staple cartridge of FIG. 29, taken along line 30-30 in FIG. 29.

B. Example of Staple Cartridge with Distal Raised Gripping Feature Ramped in Multiple Directions FIGS. 29-30 show another example of a staple cartridge (D1110) configured to deploy staples (86) toward corresponding staple forming pockets of an anvil (not shown), such as staple forming pockets (66) of anvil (44). Staple cartridge (D1110) is configured for use with end effector (40), and is similar to staple cartridge (70) described above except as otherwise described below. In this regard, staple cartridge (D1110) of the present example includes a cartridge body (D1112) having an upwardly facing deck (D1114), an elongate slot (D1118) extending along a central axis of cartridge body (D1112) and opening upwardly through deck (D1114) for slidably receiving a distal knife portion of a firing beam (not shown), such as distal knife portion (50) of firing beam (46), and a plurality of cartridge pockets (D1120) extending through deck (D1114) on each side of knife slot (D1118). In the present version, three longitudinal rows of cartridge pockets (D1120) are formed through upper deck (D1114) along each lateral side of knife slot (D1118), including an inner row, a middle row, and an outer row on each lateral side of knife slot (D1118). Each cartridge pocket (D1120) slidably houses an unformed staple (86) and a respective staple driver (not shown) similar to staple drivers (84) positioned beneath staple (86). A lower tray (not shown) similar to lower tray (76) encloses an underside of cartridge body (D1112) and thereby retains staples (86) and the staple drivers within cartridge body (D1112). A wedge sled (not shown) similar to wedge sled (82) is slidably disposed within cartridge body (D1112) and includes upwardly presented cam surfaces configured to engage the undersides of the staple drivers.

Staple cartridge (D1110) of the present example further includes a plurality of raised features in the form of pocket extenders (D1130a, D1130b, D1132) that extend upwardly from deck (D1114) at or near proximal and distal ends of each cartridge pocket (D1120), such that each cartridge pocket (D1120) is longitudinally flanked by a corresponding pair of proximal and distal pocket extenders (D1130a, D1130b, D1132). Any one or more of pocket extenders (D1130a, D1130b, D1132) may be configured to enhance the gripping of tissue (T1, T2) by staple cartridge (D1110) when end effector (40) is closed (e.g., in instances when staple cartridge (D1110) is not equipped with a buttress assembly (D110, D112, D160)), and/or to guide the legs (D126) of the staples (86) as the legs (D126) exit the respective cartridge pockets (D1120) during deployment of the staples (86). In addition, or alternatively, any one or more of pocket extenders (D1130a, D1130b, D1132) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1110).

In the example shown, the plurality of pocket extenders (D1130a, D1130b, D1132) include a plurality of first pocket extenders (D1130a, D1130b) having a first configuration, and a plurality of second pocket extenders (D1132) having a second configuration different from the first configuration. First pocket extenders (D1130a, D1130b) include proximal first pocket extenders (D1130a) that are positioned at or near the proximal ends of each cartridge pocket (D1120) of each row, and further include distal first pocket extenders (D1130b) that are positioned at or near the distal ends of each cartridge pocket (D1120) of each row, except for the distalmost cartridge pocket (D1120) of the inner and outer rows. In this regard, second pocket extenders (D1132) are positioned at or near the distal ends of the distalmost cartridge pockets (D1120) of the inner and outer rows such that each second pocket extender (D1132) spans laterally across three rows of cartridge pockets (D1120) on the respective lateral side of knife slot (D1118) (e.g., the respective inner, middle, and outer rows of cartridge pockets (D1120)).

As shown, each first pocket extender (D1130a, D1130b) includes a generally U-shaped body (D1140a, D1140b) that defines a staple leg receptacle (D1142a, D1142b) for receiving a corresponding leg (D126) of the staple (86) slidably housed within the respective cartridge pocket (D1120). In this regard, each staple leg receptacle (D1142a, D1142b) may be sized and configured to slidably receive the corresponding leg (D126) for vertically guiding the corresponding leg (D126) out of the respective cartridge pocket (D1120) toward the corresponding staple forming pockets (66) as staples (86) are driven outwardly from cartridge pockets (D1120) by the staple drivers. The body (D1140a) of each proximal first pocket extender (D1130a) also defines a proximally-facing outer surface (D1144a) that extends substantially orthogonally relative to deck (D1114), while the body (D1140b) of each distal first pocket extender (D1130b) also defines a distally-facing outer surface (D1144b) that extends substantially orthogonally relative to deck (D1114). The body (D1140a, D1140b) of each first pocket extender (D1130a, D1130b) further defines an upwardly-facing top surface (D1146a, D1146b) that extends substantially parallel relative to deck (D1114). Top surfaces (D1146a, D1146b) may be positioned at a substantially uniform height above deck (D1114).

As noted above, each second pocket extender (D1132) spans laterally across the respective inner, middle, and outer rows of cartridge pockets (D1120), and is positioned at or near the distal ends of the distalmost cartridge pockets (D1120) of the respective inner and outer rows. Each second pocket extender (D1132) includes a body (D1160) that defines a pair of staple leg receptacles (D1162) for receiving corresponding legs (D126) of the staples (86) slidably housed within the respective distalmost inner and outer cartridge pockets (D1120). In this regard, each staple leg receptacle (D1162) may be sized and configured to slidably receive the corresponding leg (D126) for vertically guiding the corresponding leg (D126) out of the respective cartridge pocket (D1120) toward the corresponding staple forming pockets (66) as staples (86) are driven outwardly from cartridge pockets (D1120) by the staple drivers.

The body (D1160) of each second pocket extender (D1132) also defines a proximally-facing outer surface (D1163) that extends substantially orthogonally relative to deck (D1114), and a distally-facing outer surface (D1164)

that extends substantially obliquely relative to deck (D1114). In the example shown, the outer surface (D1164) of each second pocket extender (D1132) is tapered proximally in a laterally-outward direction, such that the laterally-inner ends of outer surfaces (D1164) are distal of the laterally-outer ends of outer surfaces (D1164). By extending substantially obliquely relative to deck (D1114) and/or by being tapered proximally in the laterally-outward direction, the distally-facing outer surface (D1164) of each second pocket extender (D1132) may have a substantially atraumatic configuration so that each outer surface (D1164) may avoid inflicting trauma to tissue contacted by the outer surface (D1164). For example, each outer surface (D1164) may define a distal ramp for gently lifting such tissue upwardly relative to deck (D1114). Due to the spanning of each second pocket extender (D1132) laterally across the respective inner, middle, and outer rows of cartridge pockets (D1120), each outer surface (D1164) may be configured to lift the portions of such tissue that are aligned with the respective inner, middle, and outer rows of cartridge pockets (D1120). By extending substantially orthogonally relative to deck (D1114), the proximally-facing outer surface (D1163) of each second pocket extender (D1132) may be configured to apply a higher drag force and/or frictional force to tissue (T1, T2) than that applied to tissue (T1, T2) by the respective distally-facing outer surface (D1164), to thereby provide a higher pull-off load than insertion load.

The body (D1160) of each second pocket extender (D1132) further defines an upwardly-facing top surface (D1166) that extends substantially obliquely relative to deck (D1114). In the example shown, the top surface (D1166) of each second pocket extender (D1132) is tapered downwardly in the laterally-outward direction, such that the laterally-inner ends of top surfaces (D1166) are above the laterally-outer ends of top surfaces (D1166). The laterally-inner ends of top surfaces (D1166) may be positioned at a substantially same height above deck (D1114) as that of top surfaces (D1146a, D1146b). In some other versions, the laterally-inner ends of top surfaces (D1166) may be positioned at a different height above deck (D1114) from that of top surfaces (D1146a, D1146b). For example, the laterally-inner ends of top surfaces (D1166) may be positioned at a higher height above deck (D1114) than that of top surfaces (D1146a, D1146b), such that a distal tip of anvil (44) may contact the laterally-inner ends of top surfaces (D1166) before contacting top surfaces (D1146a, D1146b) during closure of end effector (40) to thereby produce an increased loading on the distal end than proximal to that location in at least a partially clamped approximation state. While the laterally-outer ends of top surfaces (D1166) are shown positioned above deck (D1114), the laterally-outer ends of top surfaces (D1166) may alternatively be positioned at a same height as deck (D1114).

In some versions, the proximally-facing outer surface (D1163) of each second pocket extender (D1132) and/or the top surface (D1166) of each second pocket extender (D1132) may be textured and/or include isolated raised features to improve frictional hold of tissue (T1, T2). For example, the proximally-facing outer surface (D1163) of each second pocket extender (D1132) may have a first surface finish (e.g., textured) that is different from a second surface finish (e.g., smooth) of the top surface (D1166) and/or distally-facing outer surface (D1164) of each second pocket extender (D1132). In addition, or alternatively, the top surface (D1166) of each second pocket extender (D1132) may have the first surface finish (e.g., textured) that is different from the second surface finish (e.g., smooth) of the distally-facing outer surface (D1164) of each second pocket extender (D1132).

V. EXAMPLES OF CARTRIDGES HAVING RAILS FOR BUTTRESS ADHESION

A. Example of Staple Cartridge with Outer Rails

Figure 31:
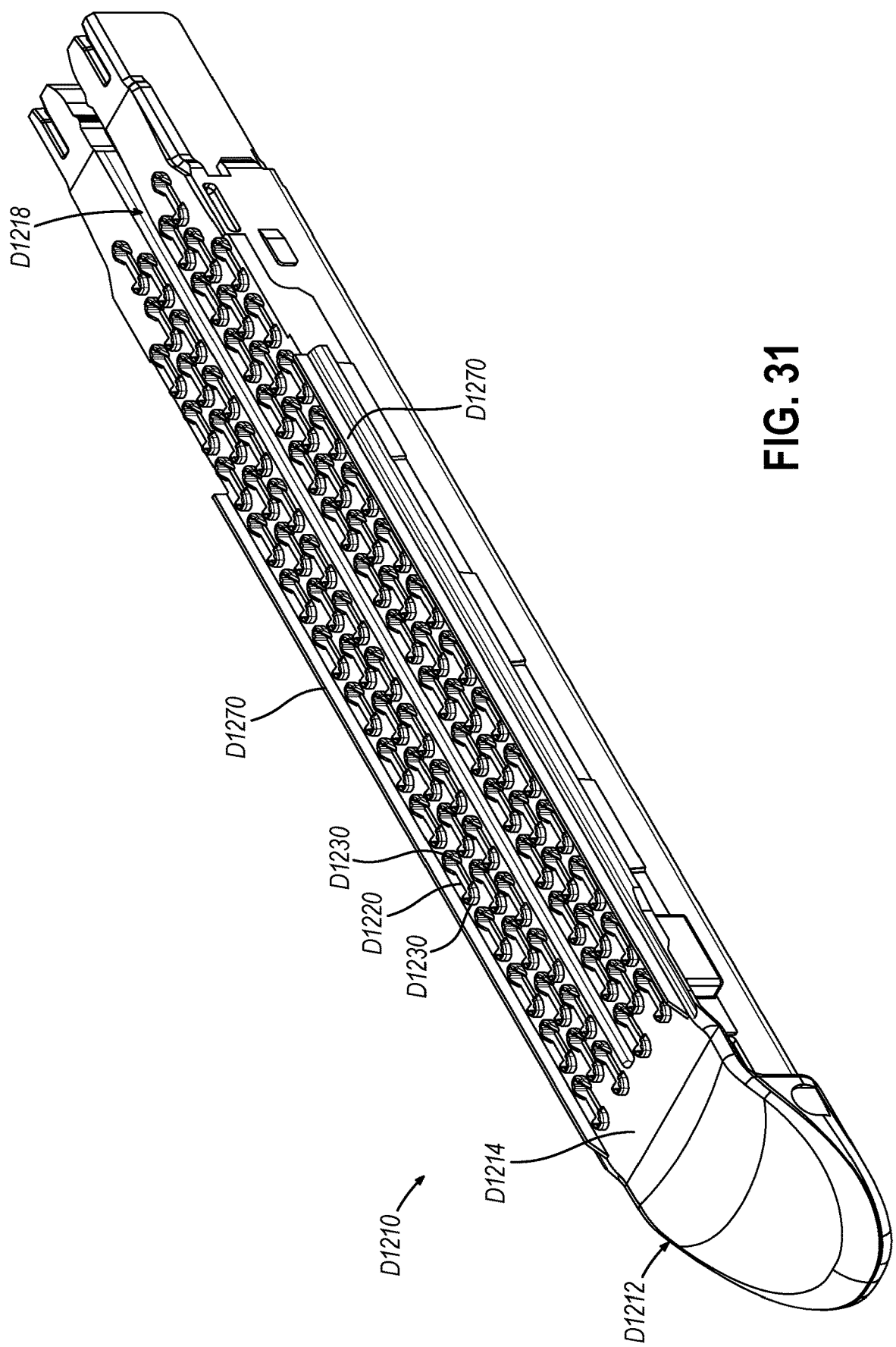
FIG. 31 depicts a perspective view of another example of a staple cartridge for use with the end effector of FIG. 2 and having laterally outer rails for buttress adhesion.

FIG. 31 shows another example of a staple cartridge (D1210) configured to deploy staples (86) toward corresponding staple forming pockets of an anvil (not shown), such as staple forming pockets (66) of anvil (44). Staple cartridge (D1210) is configured for use with end effector (40), and is similar to staple cartridge (70) described above except as otherwise described below. In this regard, staple cartridge (D1210) of the present example includes a cartridge body (D1212) having an upwardly facing deck (D1214), an elongate slot (D1218) extending along a central axis of cartridge body (D1212) and opening upwardly through deck (D1214) for slidably receiving a distal knife portion of a firing beam (not shown), such as distal knife portion (50) of firing beam (46), and a plurality of cartridge pockets (D1220) extending through deck (D1214) on each side of knife slot (D1218). In the present version, three longitudinal rows of cartridge pockets (D1220) are formed through upper deck (D1214) along each lateral side of knife slot (D1218), including an inner row, a middle row, and an outer row on each lateral side of knife slot (D1218). Each cartridge pocket (D1220) slidably houses an unformed staple (86) and a respective staple driver (not shown) similar to staple drivers (84) positioned beneath staple (86). A lower tray (not shown) similar to lower tray (76) encloses an underside of cartridge body (D1212) and thereby retains staples (86) and the staple drivers within cartridge body (D1212). A wedge sled (not shown) similar to wedge sled (82) is slidably disposed within cartridge body (D1212) and includes upwardly presented cam surfaces configured to engage the undersides of the staple drivers.

Staple cartridge (D1210) of the present example further includes a plurality of raised features in the form of pocket extenders (D1230) that extend upwardly from deck (D1214) at or near proximal and distal ends of each cartridge pocket (D1220), such that each cartridge pocket (D1220) is longitudinally flanked by a corresponding pair of proximal and distal pocket extenders (D1230). Any one or more of pocket extenders (D1230) may be configured to enhance the gripping of tissue (T1, T2) by staple cartridge (D1210) when end effector (40) is closed (e.g., in instances when staple cartridge (D1210) is not equipped with a buttress assembly (D110, D112, D160)), and/or to guide the legs (D126) of the staples (86) as the legs (D126) exit the respective cartridge pockets (D1220) during deployment of the staples (86). In addition, or alternatively, any one or more of pocket extenders (D1230) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1210).

Staple cartridge (D1210) of the present example further includes another plurality of raised features in the form of a pair of longitudinal rails (D1270) that extend upwardly from deck (D1214) along a respective lateral side of knife slot (D1218) and that are disposed laterally outwardly of the corresponding outer row of cartridge pockets (D1220). The top surfaces of rails (D1270) may be positioned at a substantially same height above deck (D1214) as that of the top surfaces of pocket extenders (D1230) such as, for example, about 0.51 mm. Any one or more of rails (D1270) may be configured to enhance the gripping of tissue (T1, T2) by staple cartridge (D1210) when end effector (40) is closed (e.g., in instances when staple cartridge (D1210) is not equipped with a buttress assembly (D110, D112, D160)). In addition, or alternatively, any one or more of rails (D1270) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1210). In some versions, any one or more of rails (D1270) may be configured to prevent the adhesive layers or beads (D116, D120, D182, D184, D186, D188) of a corresponding buttress assembly (D110, D112, D160) from spreading laterally outwardly beyond the respective rail (D1270).

Figure 32:
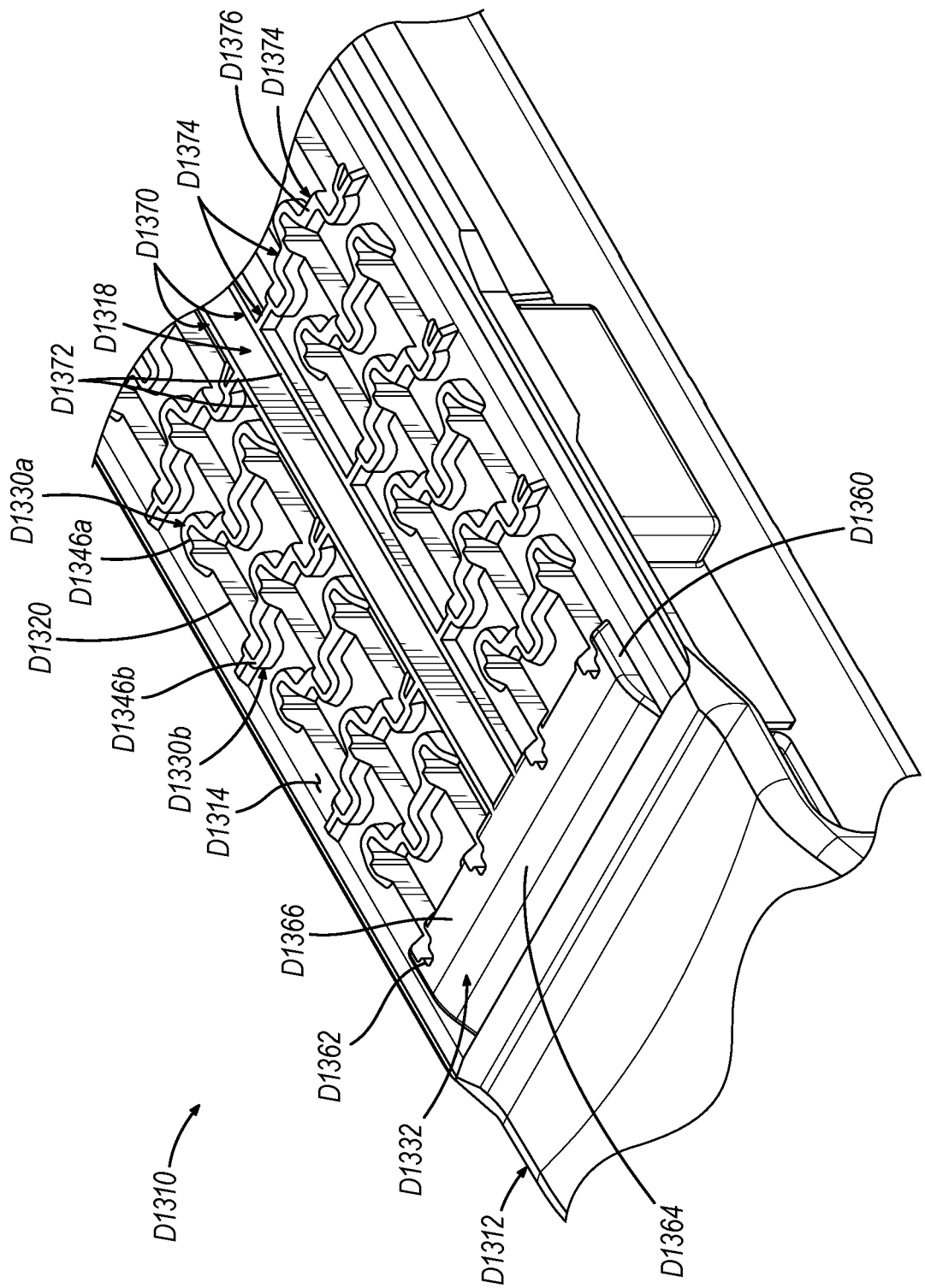
FIG. 32 depicts a partial perspective view of another example of a staple cartridge for use with the end effector of FIG. 2 and having interconnected pocket extenders and laterally inner rails for buttress adhesion.

B. Example of Staple Cartridge with Inner Rails and Interconnected Pocket Extenders FIG. 32 shows another example of a staple cartridge (D1310) configured to deploy staples (86) toward corresponding staple forming pockets of an anvil (not shown), such as staple forming pockets (66) of anvil (44). Staple cartridge (D1310) is configured for use with end effector (40), and is similar to staple cartridge (70) described above except as otherwise described below. In this regard, staple cartridge (D1310) of the present example includes a cartridge body (D1312) having an upwardly facing deck (D1314), an elongate slot (D1318) extending along a central axis of cartridge body (D1312) and opening upwardly through deck (D1314) for slidably receiving a distal knife portion of a firing beam (not shown), such as distal knife portion (50) of firing beam (46), and a plurality of cartridge pockets (D1320) extending through deck (D1314) on each side of knife slot (D1318). In the present version, three longitudinal rows of cartridge pockets (D1320) are formed through upper deck (D1314) along each lateral side of knife slot (D1318), including an inner row, a middle row, and an outer row on each lateral side of knife slot (D1318). Each cartridge pocket (D1320) slidably houses an unformed staple (86) and a respective staple driver (not shown) similar to staple drivers (84) positioned beneath staple (86). A lower tray (not shown) similar to lower tray (76) encloses an underside of cartridge body (D1312) and thereby retains staples (86) and the staple drivers within cartridge body (D1312). A wedge sled (not shown) similar to wedge sled (82) is slidably disposed within cartridge body (D1312) and includes upwardly presented cam surfaces configured to engage the undersides of the staple drivers.

Staple cartridge (D1310) of the present example further includes a plurality of raised features in the form of pocket extenders (D1330a, D1330b, D1332) that extend upwardly from deck (D1314) at or near proximal and distal ends of each cartridge pocket (D1320), such that each cartridge pocket (D1320) is longitudinally flanked by a corresponding pair of proximal and distal pocket extenders (D1330a, D1330b, D1332). Any one or more of pocket extenders (D1330a, D1330b, D1332) may be configured to enhance the gripping of tissue (T1, T2) by staple cartridge (D1310) when end effector (40) is closed (e.g., in instances when staple cartridge (D1310) is not equipped with a buttress assembly (D110, D112, D160)), and/or to guide the legs (D126) of the staples (86) as the legs (D126) exit the respective cartridge pockets (D1320) during deployment of the staples (86). In addition, or alternatively, any one or more of pocket extenders (D1330a, D1330b, D1332) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1310).

In the example shown, the plurality of pocket extenders (D1330a, D1330b, D1332) include a plurality of first pocket extenders (D1330a, D1330b) having a first configuration, and a second pocket extender (D1332) having a second configuration different from the first configuration. First pocket extenders (D1330a, D1330b) include proximal first pocket extenders (D1330a) that are positioned at or near the proximal ends of each cartridge pocket (D1320) of each row, and further include distal first pocket extenders (D1330b) that are positioned at or near the distal ends of each cartridge pocket (D1320) of each row, except for the distalmost cartridge pocket (D1320) of the inner and outer rows. In this regard, second pocket extender (D1332) is positioned at or near the distal ends of the distalmost cartridge pockets (D1320) of the inner and outer rows such that second pocket extender (D1332) spans laterally across all rows of cartridge pockets (D1320) on both lateral sides of knife slot (D1318) (e.g., the respective inner, middle, and outer rows of cartridge pockets (D1320)).

As shown, each first pocket extender (D1330a, D1330b) includes an upwardly-facing top surface (D1346a, D1346b) that extends substantially parallel relative to deck (D1314). Top surfaces (D1346a, D1346b) may be positioned at a substantially uniform height above deck (D1314).

As noted above, second pocket extender (D1332) spans laterally across all of the inner, middle, and outer rows of cartridge pockets (D1320), and is positioned at or near the distal ends of the distalmost cartridge pockets (D1320) of the inner and outer rows. Second pocket extender (D1332) includes a body (D1360) that defines four staple leg receptacles (D1362) for receiving corresponding legs (D126) of the staples (86) slidably housed within the distalmost inner and outer cartridge pockets (D1320). In this regard, each staple leg receptacle (D1362) may be sized and configured to slidably receive the corresponding leg (D126) for vertically guiding the corresponding leg (D126) out of the respective cartridge pocket (D1320) toward the corresponding staple forming pockets (66) as staples (86) are driven outwardly from cartridge pockets (D1320) by the staple drivers.

The body (D1360) of second pocket extender (D1332) also defines a distally-facing outer surface (D1364) that extends substantially obliquely relative to deck (D1314). In the example shown, the outer surface (D1364) of second pocket extender (D1332) is rounded in the longitudinal direction. In addition, or alternatively, the outer surface (D1364) of second pocket extender (D1332) may be rounded in the lateral direction, such as in a manner similar to that shown and described above in connection with FIG. 11. By extending substantially obliquely relative to deck (D1314) and/or by being rounded in the longitudinal and/or lateral direction, the outer surface (D1364) of second pocket extender (D1332) may have a substantially atraumatic configuration so that each outer surface (D1364) may avoid inflicting trauma to tissue contacted by the outer surface (D1364). For example, outer surface (D1364) may define a distal ramp for gently lifting such tissue upwardly relative to deck (D1314). Due to the spanning of each second pocket extender (D1332) laterally across all of the inner, middle, and outer rows of cartridge pockets (D1320), outer surface (D1364) may be configured to lift the portions of such tissue that are aligned with any one or more of the inner, middle, and outer rows of cartridge pockets (D1320).

The body (D1360) of second pocket extender (D1332) further defines an upwardly-facing top surface (D1366) that extends substantially parallel relative to deck (D1314). Top surface (D1366) may be positioned above deck (D1314) as that of top surfaces (D1346a, D1346b).

Due to the spanning of second pocket extender (D1332) laterally across all of the inner, middle, and outer rows of cartridge pockets (D1320), the outer surface (1064) and top surface (D1366) of second pocket extender (D1332) may provide a continuous interaction anti-snag surface to provide improved lifting of tissue without snagging such tissue.

Staple cartridge (D1310) of the present example further includes another plurality of raised features in the form of a pair of longitudinal rails (D1370) that extend upwardly from deck (D1314) and proximally from second pocket extender (D1332) along a respective lateral side of knife slot (D1318), and that are disposed laterally inwardly of the corresponding inner row of cartridge pockets (D1320). Top surfaces (D1372) of rails (D1370) may be positioned at a substantially same height above deck (D1314) as that of top surfaces (D1346a, D1346b, D1366) of pocket extenders (D1330a, D1330b, D1332) such as, for example, about 0.51 mm. Any one or more of rails (D1370) may be configured to enhance the gripping of tissue (T1, T2) by staple cartridge (D1310) when end effector (40) is closed (e.g., in instances when staple cartridge (D1310) is not equipped with a buttress assembly (D110, D112, D160)). In addition, or alternatively, any one or more of rails (D1370) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1310).

Staple cartridge (D1310) of the present example also includes another plurality of raised features in the form of bridges (D1374) that extend upwardly from deck (D1314) and laterally inwardly and/or outwardly from respective first pocket extenders (D1330a, D1330b). Top surfaces (D1376) of bridges (D1374) may be positioned at a substantially same height above deck (D1314) as that of top surfaces (D1346a, D1346b, D1366) of pocket extenders (D1330a, D1330b, D1332) and/or as that of top surfaces (D1372) of rails (D1370) such as, for example, about 0.51 mm. Any one or more of bridges (D1374) may be configured to enhance the gripping of tissue (T1, T2) by staple cartridge (D1310) when end effector (40) is closed (e.g., in instances when staple cartridge (D1310) is not equipped with a buttress assembly (D110, D112, D160)). In addition, or alternatively, any one or more of bridges (D1374) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1310).

In the example shown, bridges (D1374) interconnect various first pocket extenders (D1330a, D1330b) with each other and/or with rails (D1370), such that various top surfaces (D1346a, D1346b, D1366, D1372, D1376) are continuous with each other. As shown, the top surfaces (D1346a, D1346b) of at least some first pocket extenders (D1330a, D1330b) cooperate with the top surfaces (1376) of the corresponding bridges (D1374) to define a continuous, generally serpentine surface extending from the top surface (D1372) of the respective rail (D1370) to the respective laterally outer edge of deck (D1314).

In the example shown, pocket extenders (D1330a, D1330b, D1332), rails (D1370), and/or bridges (D1374) also collectively define a continuous lattice structure to provide staple cartridge (D1310) with improved lateral stability (e.g., during squeezing of tissue (T1, T2)).

VI. EXAMPLE OF CARTRIDGE HAVING RECEPTACLES FOR BUTTRESS ADHESION

Figure 33:
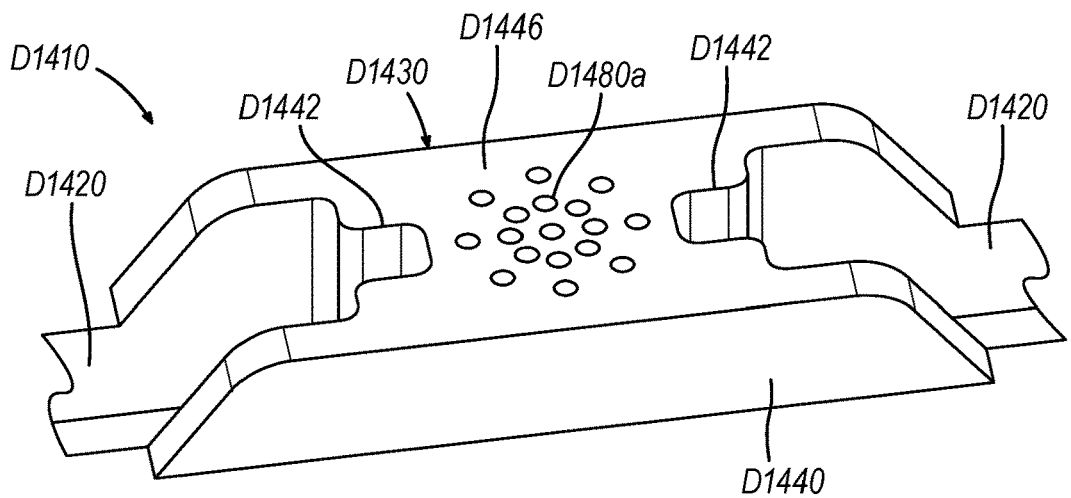
FIG. 33 depicts a partial perspective view of another example of a staple cartridge for use with the end effector of FIG. 2 and having circular receptacles for buttress adhesion.
Figure 34:
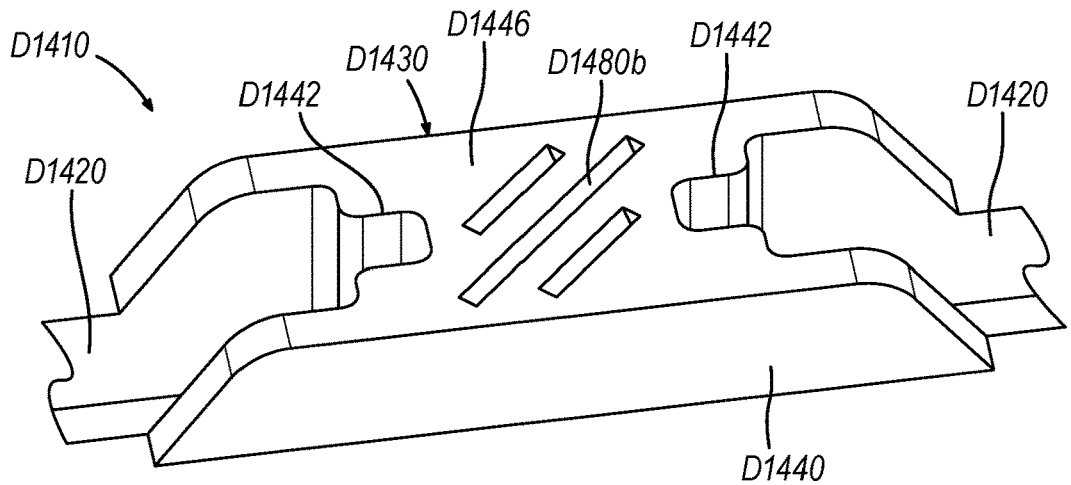
FIG. 34 depicts another partial perspective view of the staple cartridge of FIG. 33, showing linear receptacles for buttress adhesion.
Figure 35:
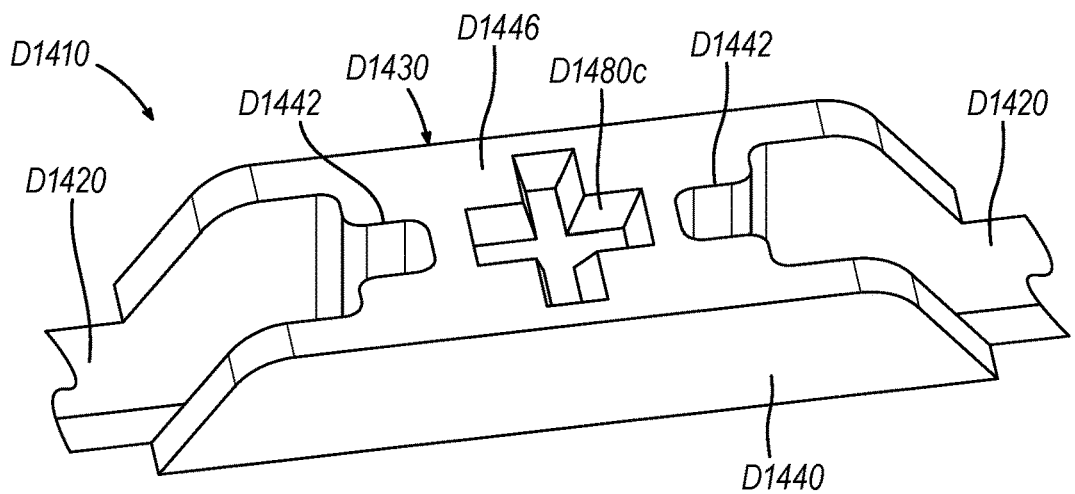
FIG. 35 depicts another partial perspective view of the staple cartridge of FIG. 33, showing a "+" shaped receptacle for buttress adhesion.

FIGS. 33-35 show portions of another example of a staple cartridge (D1410) configured to deploy staples (86) toward corresponding staple forming pockets of an anvil (not shown), such as staple forming pockets (66) of anvil (44). Staple cartridge (D1410) is configured for use with end effector (40), and is similar to staple cartridge (70) described above except as otherwise described below. In this regard, staple cartridge (D1410) of the present example includes a plurality of cartridge pockets (D1420) formed through an upper deck (not shown) on each lateral side of a knife slot (not shown). Each cartridge pocket (D1420) slidably houses an unformed staple (86) and a respective staple driver (not shown) similar to staple drivers (84) positioned beneath staple (86).

Staple cartridge (D1410) of the present example further includes a plurality of raised features in the form of pocket extenders (D1430) that extend upwardly from the deck at or near proximal and distal ends of each cartridge pocket (D1420), such that each cartridge pocket (D1420) is longitudinally flanked by a corresponding pair of pocket extenders (D1430). Any one or more of pocket extenders (D1430) may be configured to enhance the gripping of tissue (T1, T2) by staple cartridge (D1410) when end effector (40) is closed (e.g., in instances when staple cartridge (D1410) is not equipped with a buttress assembly (D110, D112, D160)), and/or to guide the legs (D126) of the staples (86) as the legs (D126) exit the respective cartridge pockets (D1420) during deployment of the staples (86). In addition, or alternatively, any one or more of pocket extenders (D1430) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1410).

As shown, each pocket extender (D1430) includes a body (D1440) that defines proximal and distal staple leg receptacles (D1442) for receiving corresponding legs (D126) of the staples (86) slidably housed within the respective cartridge pockets (D1420). The body (D1440) of each pocket extender (D1430) further defines an upwardly-facing top surface (D1446) that extends substantially parallel relative to the deck.

Staple cartridge (D1410) of the present example further includes a plurality of recesses (D1480a, D1480b, D1480c) that extend downwardly from the top surfaces (D1446) of respective pocket extenders (D1430). More particularly, a generally circular array of generally circular recesses (D1480a) extend downwardly from the top surface (D1446) of at least one respective pocket extender (D1430) as shown in FIG. 33; a plurality of generally linear recesses (D1480b) oriented obliquely relative to the knife slot extend downwardly from the top surface (D1446) of at least one respective pocket extender (D1430) as shown in FIG. 34; and a single generally "+" shaped recess (D1480c) extends downwardly from the top surface (D1446) of at least one respective pocket extender (D1430) as shown in FIG. 35. Any one or more of recesses (D1480a, D1480b, D1480c) may be configured to receive respective portions of the adhesive layers or beads (D116, D120, D182, D184, D186, D188) of a corresponding buttress assembly (D110, D112, D160) to promote attachment of the corresponding buttress assembly (D110, D112, D160) to staple cartridge (D1410).

While recesses (D1480a, D1480b, D1480c) have been described as being incorporated together into a single staple cartridge (D1410), it will be appreciated that any suitable type(s) of recess(es) (D1480a, D1480b, D1480c) may be incorporated into a particular staple cartridge. For example, only a single type of recess (D1480a, D1480b, D1480c) may be incorporated into a given staple cartridge. It will also be appreciated that recesses (D1480a, D1480b, D1480c) may be configured in any other suitable manners beyond those shown in FIGS. 33-35.

VII. EXAMPLES OF CARTRIDGES HAVING RAISED SURFACES FOR TISSUE FLOW CONTROL

A. Example of Staple Cartridge with Bi-Directionally Tapered Deck Surface

Figure 36:
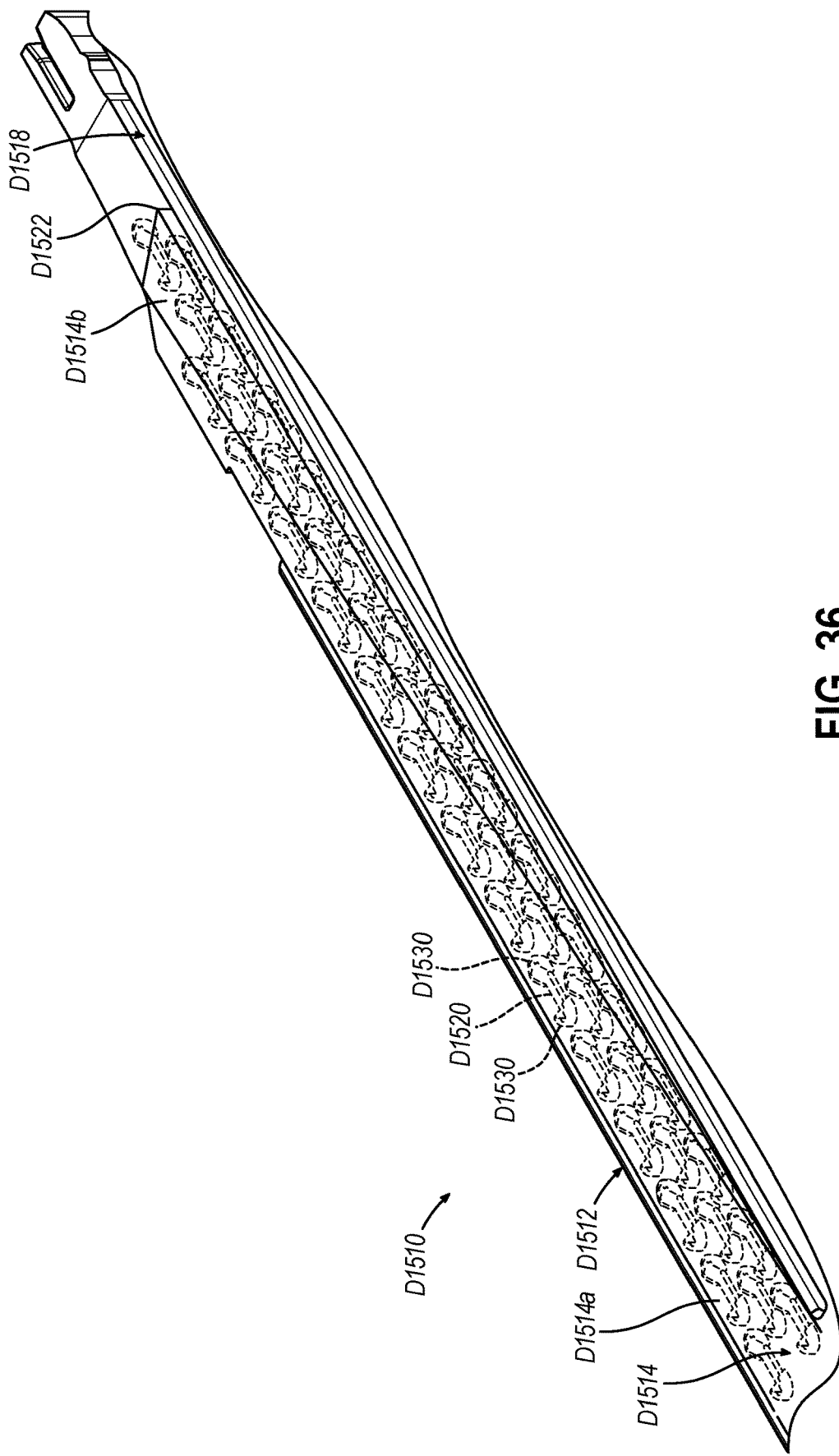
FIG. 36 depicts a partial perspective view of another example of a staple cartridge for use with the end effector of FIG. 2 and having a bi-directionally tapered deck surface for tissue flow control.
Figure 37:
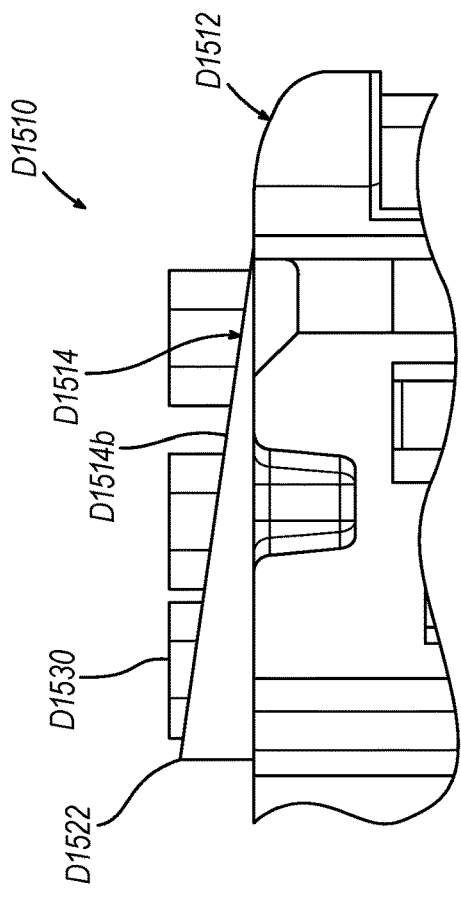
FIG. 37 depicts a rear elevational view of the staple cartridge of FIG. 36.
Figure 38:
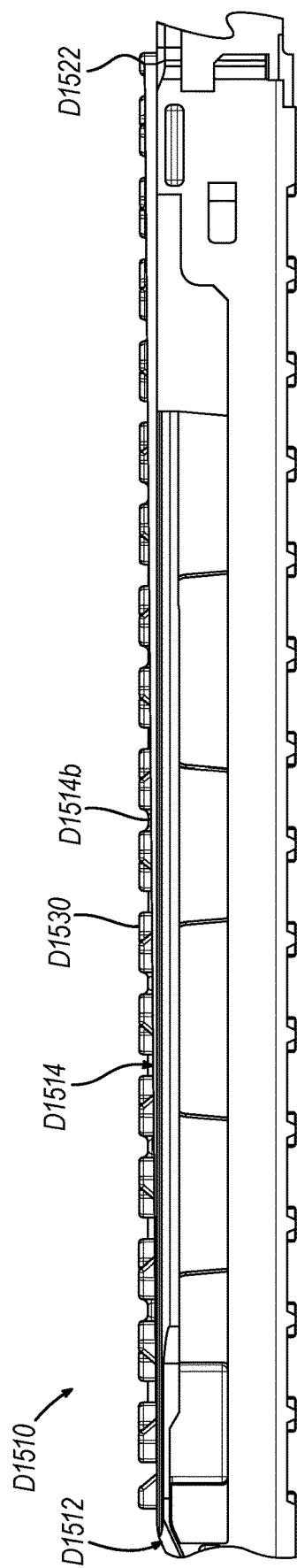
FIG. 38 depicts a side elevational view of the staple cartridge of FIG. 36.

FIGS. 36-38 show another example of a staple cartridge (D1510) configured to deploy staples (86) toward corresponding staple forming pockets of an anvil (not shown), such as staple forming pockets (66) of anvil (44). Staple cartridge (D1510) is configured for use with end effector (40), and is similar to staple cartridge (70) described above except as otherwise described below. In this regard, staple cartridge (D1510) of the present example includes a cartridge body (D1512) having an upwardly facing, multi-surface deck (D1514), an elongate slot (D1518) extending along a central axis of cartridge body (D1512) and opening upwardly through deck (D1514) for slidably receiving a distal knife portion of a firing beam (not shown), such as distal knife portion (50) of firing beam (46), and a plurality of cartridge pockets (D1520) extending through deck (D1514) on each side of knife slot (D1518). In the present version, three longitudinal rows of cartridge pockets (D1520) are formed through upper deck (D1514) along each lateral side of knife slot (D1518), including an inner row, a middle row, and an outer row on each lateral side of knife slot (D1518). Each cartridge pocket (D1520) slidably houses an unformed staple (86) and a respective staple driver (not shown) similar to staple drivers (84) positioned beneath staple (86). A lower tray (not shown) similar to lower tray (76) encloses an underside of cartridge body (D1512) and thereby retains staples (86) and the staple drivers within cartridge body (D1512). A wedge sled (not shown) similar to wedge sled (82) is slidably disposed within cartridge body (D1512) and includes upwardly presented cam surfaces configured to engage the undersides of the staple drivers.

Multi-surface deck (D1514) of the present example includes a flat (e.g., horizontal) base surface (D1514a) and a bi-directionally tapered raised surface (D1514b). In the example shown, raised surface (D1514b) tapers downwardly in both the distal and laterally outward directions. More particularly, raised surface (D1514b) tapers downwardly in both such directions from peaks (D1522) on each lateral side of knife slot (D1518) that define both a proximal-most and laterally-innermost portion of raised surface (D1514b), to base surface (D1514a). Peaks (D1522) of the present example are each positioned adjacent to a proximal region of knife slot (D1518). For example, peaks (D1522) may be positioned adjacent to or slightly distal of the proximal position of the wedge sled disposed within cartridge body (D1512).

Staple cartridge (D1510) of the present example further includes a plurality of raised features in the form of pocket extenders (D1530) that extend upwardly from deck (D1514) at or near proximal and distal ends of each cartridge pocket (D1520), such that each cartridge pocket (D1520) is longitudinally flanked by a corresponding pair of proximal and distal pocket extenders (D1530). Any one or more of pocket extenders (D1530) may be configured to enhance the gripping of tissue (T1, T2) by staple cartridge (D1510) when end effector (40) is closed (e.g., in instances when staple cartridge (D1510) is not equipped with a buttress assembly (D110, D112, D160)), and/or to guide the legs (D126) of the staples (86) as the legs (D126) exit the respective cartridge pockets (D1520) during deployment of the staples (86). In addition, or alternatively, any one or more of pocket extenders (D1530) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1510).

Due to the downward tapering of raised surface (D1514b) in both the distal and laterally outward directions, raised surface (D1514b) may provide tighter compression of tissue (T1, T2) adjacent to a proximal region of knife slot (D1518), thereby inhibiting dragging of tissue (T1, T2) by distal knife portion (50) upon initial contact between distal knife portion (50) and tissue (T1, T2) during distal translation of firing beam (46) (e.g., during a firing stroke), and instead promoting piercing of tissue (T1, T2) by distal knife portion (50) to provide a clean cut. In addition, or alternatively, raised surface (D1514b) may similarly inhibit movement (e.g., "plowing") of the buttress assembly (D110, D112, D160) and instead promote piercing of the buttress assembly (D110, D112, D160) by distal knife portion (50) to provide a clean cut. In some instances, the downward tapering of raised surface (D1514b) in both the distal and laterally outward directions may assist with guiding the fluid phase of clamped tissue (T1, T2) outwardly both laterally and longitudinally due to the tendency of fluid to flow in the path of least resistance, which may result in an increase in the amount of fluid evacuated from clamped tissue (T1, T2) prior to distal translation of firing beam (46) (e.g., prior to a firing stroke). This may lead to a decrease in fluid flow during distal translation of firing beam (46), thereby reducing any risk of the legs (D126) of staples (86) drifting and thus reducing any risk of staples (86) being malformed. In addition, or alternatively, the downward tapering of raised surface (D1514b) in both the distal and laterally outward directions may have a minimal impact on the overall compression forces applied to tissue (T1, T2), thereby reducing any risk of excessive force-to-close and/or any risk of de-cambering.

B. Example of Staple Cartridge with Convex Deck Surface

Figure 39:
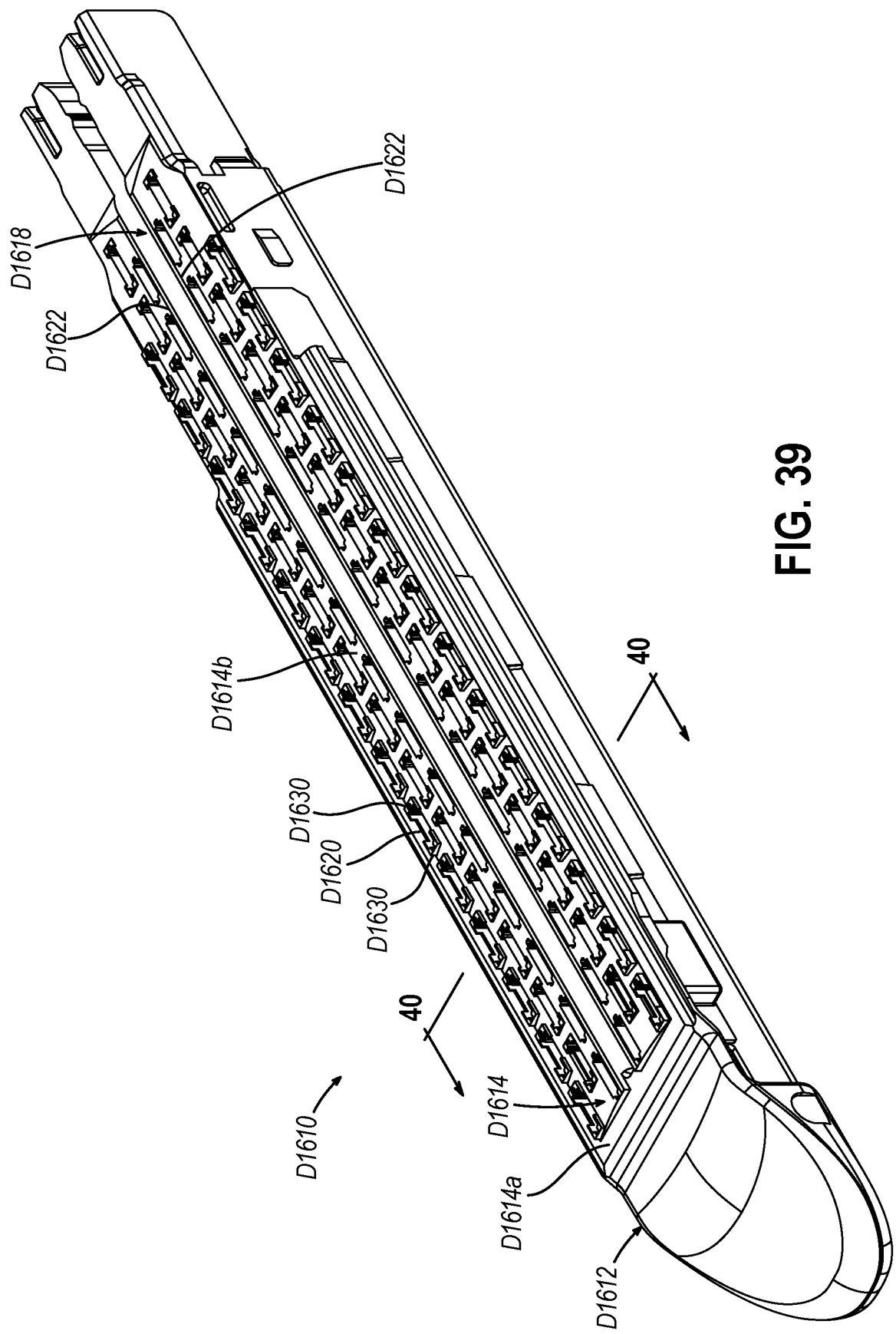
FIG. 39 depicts a perspective view of another example of a staple cartridge for use with the end effector of FIG. 2 and having a convex deck surface for tissue flow control.
Figure 40:
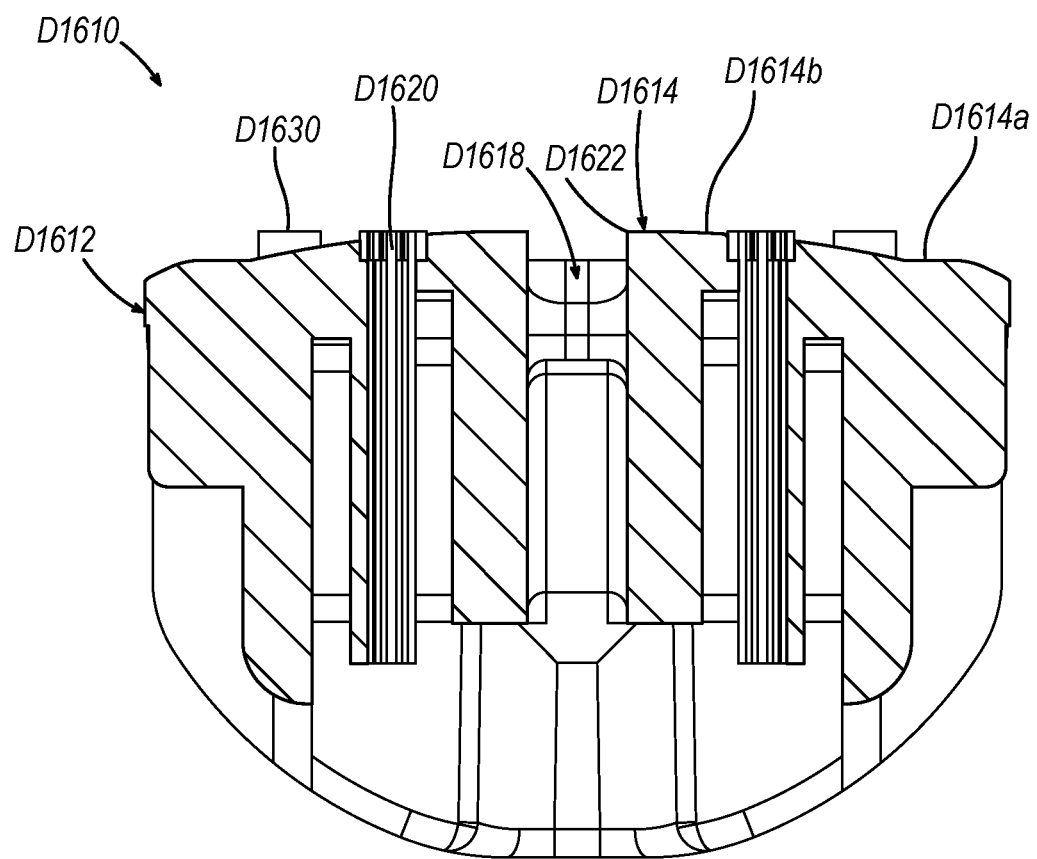
FIG. 40 depicts a cross sectional view of the staple cartridge of FIG. 39, taken along line 40-40 of FIG. 39.

FIGS. 39-40 show another example of a staple cartridge (D1610) configured to deploy staples (86) toward corresponding staple forming pockets of an anvil (not shown), such as staple forming pockets (66) of anvil (44). Staple cartridge (D1610) is configured for use with end effector (40), and is similar to staple cartridge (70) described above except as otherwise described below. In this regard, staple cartridge (D1610) of the present example includes a cartridge body (D1612) having an upwardly facing, multi-surface deck (D1614), an elongate slot (D1618) extending along a central axis of cartridge body (D1612) and opening upwardly through deck (D1614) for slidably receiving a distal knife portion of a firing beam (not shown), such as distal knife portion (50) of firing beam (46), and a plurality of cartridge pockets (D1620) extending through deck (D1614) on each side of knife slot (D1618). In the present version, three longitudinal rows of cartridge pockets (D1620) are formed through upper deck (D1614) along each lateral side of knife slot (D1618), including an inner row, a middle row, and an outer row on each lateral side of knife slot (D1618). Each cartridge pocket (D1620) slidably houses an unformed staple (86) and a respective staple driver (not shown) similar to staple drivers (84) positioned beneath staple (86). A lower tray (not shown) similar to lower tray (76) encloses an underside of cartridge body (D1612) and thereby retains staples (86) and the staple drivers within cartridge body (D1612). A wedge sled (not shown) similar to wedge sled (82) is slidably disposed within cartridge body (D1612) and includes upwardly presented cam surfaces configured to engage the undersides of the staple drivers.

Multi-surface deck (D1614) of the present example includes a flat (e.g., horizontal) base surface (D1614a) and a convex raised surface (D1614b). In the example shown, raised surface (D1614b) curves downwardly in the laterally outward direction. More particularly, raised surface (D1614b) curves downwardly in such direction from peaks (D1622) on each lateral side of knife slot (D1618) that define a laterally-innermost portion of raised surface (D1614b), to base surface (D1614a). Due to the downward curving of raised surface (D1614b) in the laterally outward directions, raised surface (D1614b) may promote flow of tissue (T1, T2) away from the cutline.

Staple cartridge (D1610) of the present example further includes a plurality of raised features in the form of pocket extenders (D1630) that extend upwardly from deck (D1614) at or near proximal and distal ends of each cartridge pocket (D1620) in the middle and outer rows, such that cartridge pockets (D1620) in the middle and outer rows are each longitudinally flanked by a corresponding pair of proximal and distal pocket extenders (D1630) while cartridge pockets (D1620) in the inner rows are equipped with neither a corresponding proximal nor distal pocket extender (D1630). Any one or more of pocket extenders (D1630) may be configured to enhance the gripping of tissue (T1, T2) by staple cartridge (D1610) when end effector (40) is closed (e.g., in instances when staple cartridge (D1610) is not equipped with a buttress assembly (D110, D112, D160)), and/or to guide the legs (D126) of the staples (86) as the legs (D126) exit the respective cartridge pockets (D1620) during deployment of the staples (86). In addition, or alternatively, any one or more of pocket extenders (D1630) may be configured to contact the adhesive layers or beads (D116, D120, D182, D184, D186, D188) of a corresponding buttress assembly (D110, D112, D160) to promote attachment of the corresponding buttress assembly (D110, D112, D160) to staple cartridge (D1610).

Figure 41:
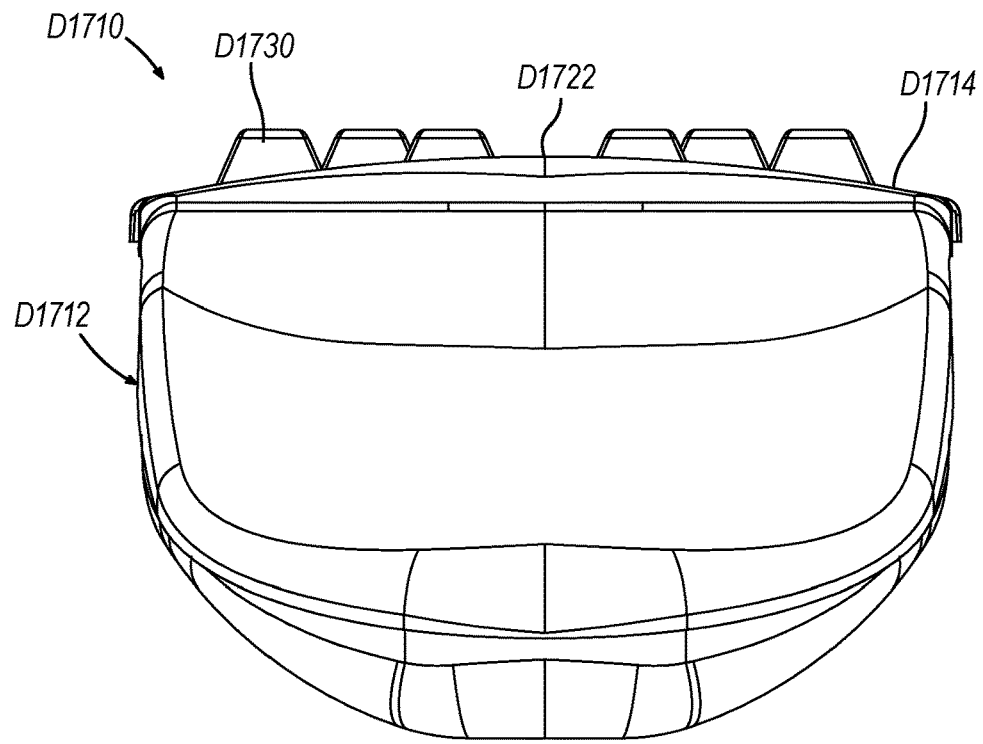
FIG. 41 depicts a front elevational view of another example of a staple cartridge for use with the end effector of FIG. 2 and having a convex deck surface and level pocket extenders.

C. Example of Staple Cartridge with Convex Deck Surface and Level Pocket Extenders FIG. 41 shows another example of a staple cartridge (D1710) configured to deploy staples (86) toward corresponding staple forming pockets of an anvil (not shown), such as staple forming pockets (66) of anvil (44). Staple cartridge (D1710) is configured for use with end effector (40), and is similar to staple cartridge (70) described above except as otherwise described below. In this regard, staple cartridge (D1710) of the present example includes a cartridge body (D1712) having an upwardly facing, convex deck (D1714), and a plurality of cartridge pockets (not shown) extending through deck (D1714) on each side of a knife slot (not shown). Convex deck (D1714) of the present example curves downwardly in the laterally outward direction on each side of the knife slot from a central peak (1722). Staple cartridge (D1710) of the present example further includes a plurality of raised features in the form of pocket extenders (D1730) that extend upwardly from deck (D1714) at or near proximal and distal ends of each cartridge pocket. In the example shown, the top surfaces of pocket extenders (D1730) are generally flat, and are generally level with each other.

Figure 42:
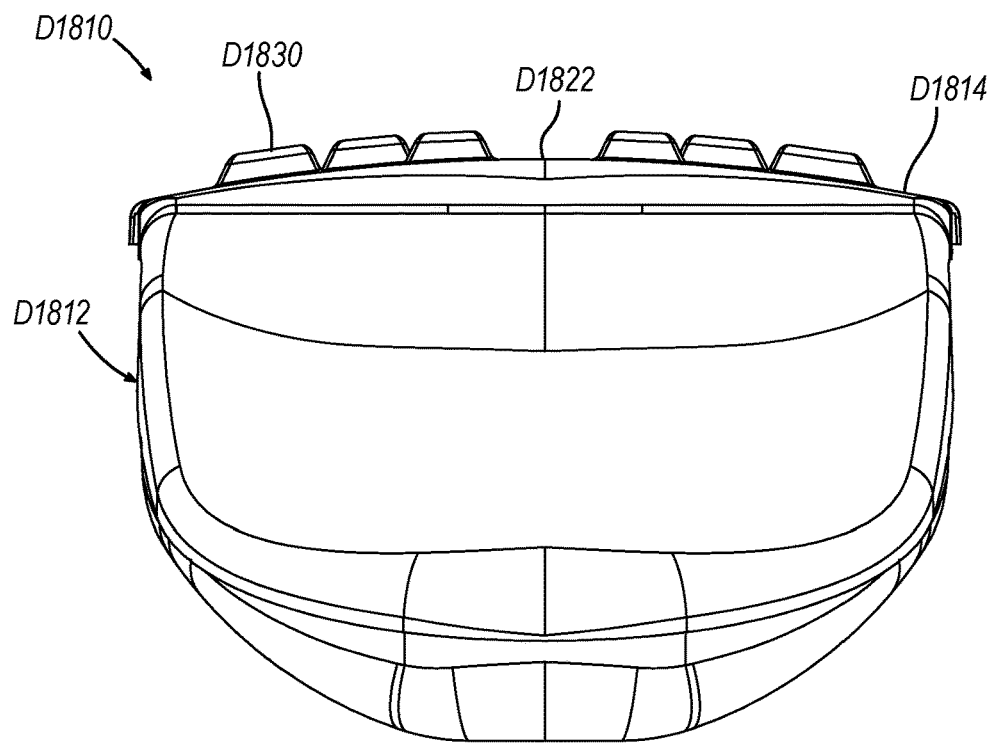
FIG. 42 depicts a front elevational view of another example of a staple cartridge for use with the end effector of FIG. 2 and having a convex deck surface and curved pocket extenders.

D. Example of Staple Cartridge with Convex Deck Surface and Curved Pocket Extenders FIG. 42 shows another example of a staple cartridge (D1810) configured to deploy staples (86) toward corresponding staple forming pockets of an anvil (not shown), such as staple forming pockets (66) of anvil (44). Staple cartridge (D1810) is configured for use with end effector (40), and is similar to staple cartridge (70) described above except as otherwise described below. In this regard, staple cartridge (D1810) of the present example includes a cartridge body (D1812) having an upwardly facing, convex deck (D1814), and a plurality of cartridge pockets (not shown) extending through deck (D1814) on each side of a knife slot (not shown). Convex deck (D1814) of the present example curves downwardly in the laterally outward direction on each side of the knife slot from a central peak (1822). Staple cartridge (D1810) of the present example further includes a plurality of raised features in the form of pocket extenders (D1830) that extend upwardly from deck (D1814) at or near proximal and distal ends of each cartridge pocket. In the example shown, the top surfaces of pocket extenders (D1830) are generally convex, and are generally arranged along an arc.

Figure 43:
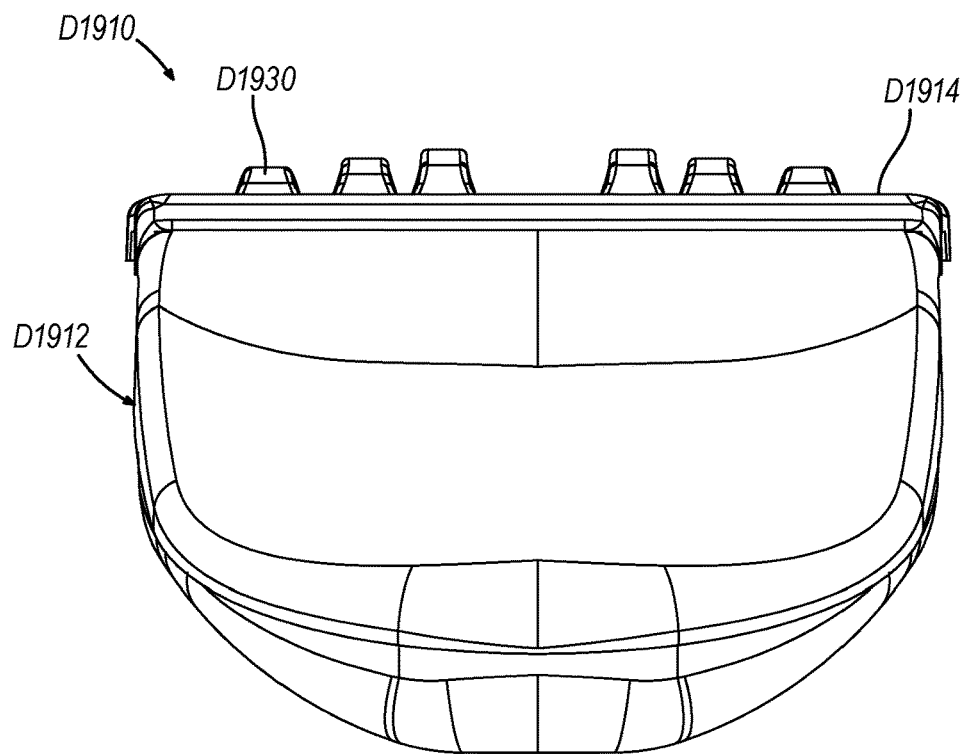
FIG. 43 depicts a front elevational view of another example of a staple cartridge for use with the end effector of FIG. 2 and having a flat deck surface and stepped pocket extenders.

E. Example of Staple Cartridge with Flat Deck Surface and Stepped Pocket Extenders FIG. 43 shows another example of a staple cartridge (D1910) configured to deploy staples (86) toward corresponding staple forming pockets of an anvil (not shown), such as staple forming pockets (66) of anvil (44). Staple cartridge (D1910) is configured for use with end effector (40), and is similar to staple cartridge (70) described above except as otherwise described below. In this regard, staple cartridge (D1910) of the present example includes a cartridge body (D1912) having an upwardly facing, flat deck (D1914), and a plurality of cartridge pockets (not shown) extending through deck (D1914) on each side of a knife slot (not shown). Staple cartridge (D1910) of the present example further includes a plurality of raised features in the form of pocket extenders (D1930) that extend upwardly from deck (D1914) at or near proximal and distal ends of each cartridge pocket. In the example shown, the top surfaces of pocket extenders (D1930) are generally flat, and are generally arranged in a stepped configuration. More particularly, the top surfaces of the pocket extenders (D1930) corresponding to an inner row of cartridge pockets are at a first height above deck (D1914), the top surfaces of the pocket extenders (D1930) corresponding to an middle row of cartridge pockets are at a second height above deck (D1914) less than the first height, and the top surfaces of the pocket extenders (D1930) corresponding to an outer row of cartridge pockets are at a third height above deck (D1914) less than the second height.

F. Example of Staple Cartridge with Stepped Deck and Stepped Pocket Extenders

Figure 44:
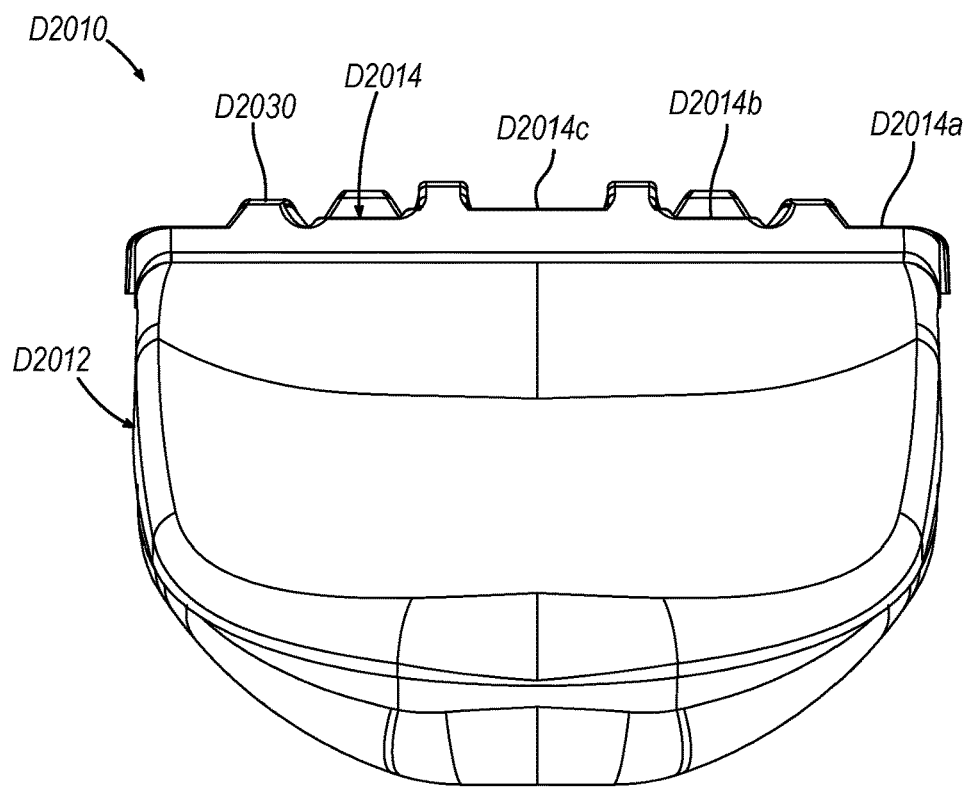
FIG. 44 depicts a front elevational view of another example of a staple cartridge for use with the end effector of FIG. 2 and having a stepped deck surface and stepped pocket extenders.

FIG. 44 shows another example of a staple cartridge (D2010) configured to deploy staples (86) toward corresponding staple forming pockets of an anvil (not shown), such as staple forming pockets (66) of anvil (44). Staple cartridge (D2010) is configured for use with end effector (40), and is similar to staple cartridge (70) described above except as otherwise described below. In this regard, staple cartridge (D2010) of the present example includes a cartridge body (D2012) having an upwardly facing, stepped deck (D2014), and a plurality of cartridge pockets (not shown) extending through deck (D2014) on each side of a knife slot (not shown).

Stepped deck (D2014) of the present example includes a lower deck surface (D2014*a*) spanning across the outer rows of cartridge pockets on each lateral side of the knife slot, an intermediate deck surface (D2014*b*) spanning across the middle rows of cartridge pockets on each lateral side of the knife slot, and an upper deck surface (D2014*c*) spanning across the inner rows of cartridge pockets on each lateral side of the knife slot.

Staple cartridge (D2010) of the present example further includes a plurality of raised features in the form of pocket extenders (D2030) that extend upwardly from deck (D2014) at or near proximal and distal ends of each cartridge pocket. In the example shown, the top surfaces of pocket extenders (D2030) are generally flat, and are generally arranged in a stepped configuration. More particularly, the top surfaces of the pocket extenders (D2030) corresponding to the inner rows of cartridge pockets are at a first height above a reference surface of deck (D2014) (e.g., lower deck surface (D2014*a*), the top surfaces of the pocket extenders (D2030) corresponding to the middle rows of cartridge pockets are at a second height above deck (D2014) less than the first height, and the top surfaces of the pocket extenders (D2030) corresponding to the outer rows of cartridge pockets are at a third height above deck (D2014) less than the second height.

G. Example of Staple Cartridge with Flat Deck and Outer Reliefs

Figure 45:
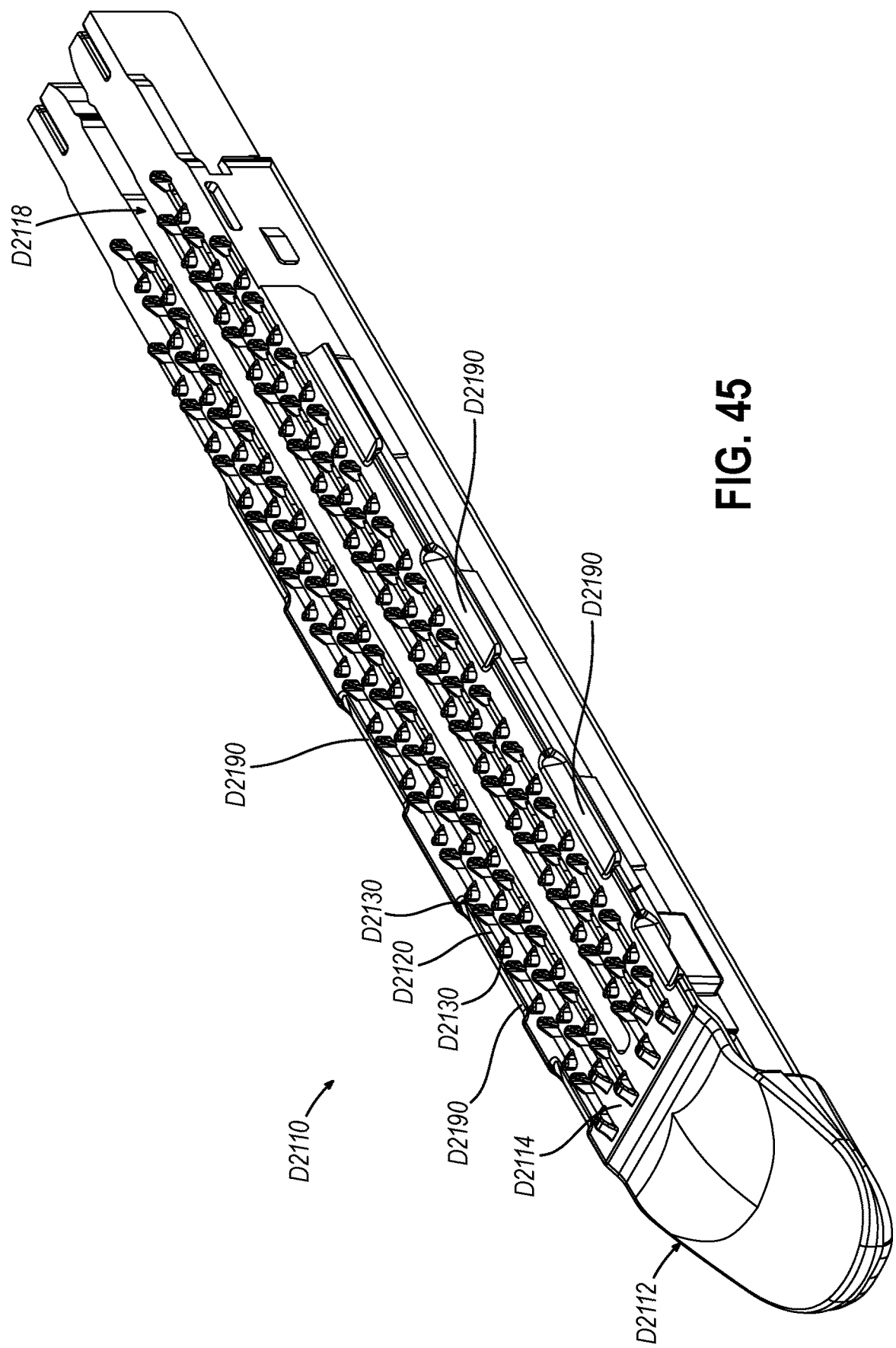
FIG. 45 depicts a front elevational view of another example of a staple cartridge for use with the end effector of FIG. 2 and having a flat deck and laterally outer reliefs.

FIG. 45 shows another example of a staple cartridge (D2110) configured to deploy staples (86) toward corresponding staple forming pockets of an anvil (not shown), such as staple forming pockets (66) of anvil (44). Staple cartridge (D2110) is configured for use with end effector (40), and is similar to staple cartridge (70) described above except as otherwise described below. In this regard, staple cartridge (D2110) of the present example includes a cartridge body (D2012) having an upwardly facing deck (D2114), and a plurality of cartridge pockets (D2120) extending through deck (D2114) on each side of a knife slot (D2118). Staple cartridge (D2110) of the present example further includes a plurality of raised features in the form of pocket extenders (D2130) that extend upwardly from deck (D2114) at or near proximal and distal ends of each cartridge pocket (D2120).

In the example shown, staple cartridge (D2110) also includes a plurality of reliefs (D2190) positioned along the laterally outer edges of deck (D2114), whereat tissue (T1, T2) may drape staple cartridge (D2110). In this regard, reliefs (D2190) may inhibit longitudinal movement (e.g., "flow") of the tissue (T1, T2) being severed and stapled.

In some versions, any one or more of the configurations shown in FIGS. 41-45 may be combined with each other.

It will be understood that while the features shown and described above are presented in the context of staple cartridges (D210, D310, D410, D510, D610, D710, D810, D910, D1010, D1110, D1210, D1310, D1410, D1510, D1610, D1710, D1810, D1910, D2010, D2110) for surgical stapler (10), such features may also be applied to staple cartridges configured for use with various other types of surgical staplers, such as linear surgical staplers.

VIII. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A stapling assembly (D210, D310, D410, D510, D610, D710, D810, D910, D1010, D1110, D1310, D1510, D1610) for a surgical instrument (10), the stapling assembly comprising: (a) a body (D212, D312, D412, D512, D612, D712, D812, D912, D1012, D1112, D1312, D1512, D1612) extending along a longitudinal axis and having an upper deck (D214, D314, D414, D514, D614, D714, D814, D914, D1014, D1114, D1314, D1514, D1614), wherein the upper deck defines a stapling surface; (b) a plurality of pockets (D220, D320, D420, D520, D620, D720, D820, D920, D1020, D1120, D1320, D1520, D1620) extending through the upper deck for receiving respective staples (86), wherein the plurality of pockets are arranged in at least two longitudinal rows; (c) a plurality of staple drivers (84), wherein each staple driver of the plurality of staple drivers is aligned with and movable vertically within a respective pocket of the plurality of pockets for actuating the respective staple into tissue (T1, T2); (d) a staple driver actuator (82) configured to translate distally relative to the body for lifting the plurality of staple drivers sequentially; (e) a plurality of pocket extenders (D230*a*, D230*b*, D330*a*, D330*b*, D430, D530, D630, D730, D830, D930, D1030*a*, D1030*b*, D1130*a*, D1130*b*, D1330*a*, D1330*b*, D1530, D1630) extending upwardly from the upper deck, wherein each pocket extender of the plurality of pocket extenders has a respective top surface (D246*a*, D246*b*, D346*a*, D346*b*, D446, D546, D646, D746, D846, D946, D1046*a*, D1046*b*, D1146*a*, D1146*b*, D1346*a*, D1346*b*) that defines an uppermost surface of the stapling assembly; and (f) at least one upwardly-facing surface (D256, D266, D356, D366, D456, D466, D556, D656, D666, D756, D856, D866, D956, D1066, D1166, D1364, D1514*b*, D1614*b*) configured to contact an adhesive portion (D116, D120, D166) of an adjunct (D110, D112, D160) for securing the adjunct to the stapling assembly, wherein the at least one upwardly-facing surface is disposed at least partially between at least a portion of the upper deck and the top surfaces of the plurality of pocket extenders, wherein the at least one upwardly-facing surface spans laterally at least partially across the at least two longitudinal rows of the plurality of pockets.

Example 2

The stapling assembly of Example 1, wherein the at least one upwardly-facing surface has a greater surface area than each top surface of the plurality of pocket extenders.

Example 3

The stapling assembly of any of Examples 1 through 2, wherein the plurality of pocket extenders a distalmost pocket extender, wherein the at least one upwardly-facing surface extends further distally than the top surface of the distalmost pocket extender.

Example 4

The stapling assembly of any of Examples 1 through 3, wherein the plurality of pocket extenders includes a proximal-most pocket extender, wherein the at least one upwardly-facing surface extends further proximally than the top surface of the proximal-most pocket extender.

Example 5

The stapling assembly of any of Examples 1 through 4, wherein the at least one upwardly-facing surface extends substantially parallel to the upper deck.

Example 6

The stapling assembly of any of Examples 1 through 4, wherein the at least one upwardly-facing surface extends substantially obliquely to the upper deck.

Example 7

The stapling assembly of Example 6, wherein the at least one upwardly-facing surface includes at least one upwardly and proximally-facing surface that extends upwardly and distally from the upper deck to a peak (D458, D558, D658).

Example 8

The stapling assembly of any of Examples 6 through 7, wherein the at least one upwardly-facing surface includes at least one upwardly and distally-facing surface that extends upwardly and proximally from the upper deck to a peak (D468, D558, D668, D1522).

Example 9

The stapling assembly of Example 8, wherein the peak of the at least one upwardly and distally-facing surface coincides with the peak of a corresponding upwardly and proximally-facing surface.

Example 10

The stapling assembly of any of Examples 8 through 9, further comprising at least one proximally-facing surface (D664) that extends substantially orthogonally relative to the upper deck from the upper deck to the peak of the at least one upwardly and distally-facing surface.

Example 11

The stapling assembly of any of Examples 1 through 10, wherein the at least one upwardly-facing surface includes at least one hemispherical surface (D556).

Example 12

The stapling assembly of any of Examples 1 through 11, wherein the at least one upwardly-facing surface is shaped to substantially match a pattern of the adhesive portion of the adjunct.

Example 13

The stapling assembly of any of Examples 1 through 12, further comprising at least one opening (D451, D461, D551, D651, D661, D861, D951) extending through the at least one upwardly-facing surface and overlying a corresponding pocket of the plurality of pockets for accommodating passage of the respective staple therethrough.

Example 14

The stapling assembly of any of Examples 1 through 13, further comprising at least one atraumatic, distally-facing surface (D254, D264, D354, D364, D459, D659, D754, D854, D1064, D1164) extending downwardly and distally from the at least one upwardly-facing surface and configured to lift tissue upwardly relative to the upper deck.

Example 15

A surgical instrument (10), comprising: (a) the stapling assembly of any of Examples 1 through 14; and (b) an adjunct (D110, D112, D160) secured to the stapling assembly, wherein the adjunct includes: (i) an adjunct material portion (D114, D118, D164), and (ii) an adhesive portion (D116, D120, D166) contacting the at least one upwardly-facing surface of the stapling assembly.

Example 16

A stapling assembly (D210, D310, D410, D510, D610, D710, D810, D910, D1010, D1110, D1310) for a surgical instrument (10), the stapling assembly comprising: (a) a body (D212, D312, D412, D512, D612, D712, D812, D912, D1012, D1112, D1312) extending along a longitudinal axis and having an upper deck (D214, D314, D414, D514, D614, D714, D814, D914, D1014, D1114, D1314), wherein the upper deck defines a stapling surface; (b) a plurality of pockets (D220, D320, D420, D520, D620, D720, D820, D920, D1020, D1120, D1320) extending through the upper deck for receiving respective staples (86), wherein the plurality of pockets are arranged in a plurality of longitudinal rows; (c) a plurality of staple drivers (84), wherein each staple driver of the plurality of staple drivers is aligned with and movable vertically within a respective pocket of the plurality of pockets for actuating the respective staple into tissue (T1, T2); (d) a staple driver actuator (82) configured to translate distally relative to the body for lifting the plurality of staple drivers sequentially; and (e) a plurality of pocket extenders (D230a, D230b, D232, D234, D330a, D330b, D332, D334, D430, D530, D630, D730, D830, D930, D1030a, D1030b, D1032, D1130a, D1130b, D1132, D1330a, D1330b, D1332) extending upwardly from the upper deck, wherein the plurality of pocket extenders includes a first distalmost pocket extender (D234, D334, D1032, D1132, D1332) having: (i) a first distally-facing surface (D264, D364, D1064, D1164, D1364) that is configured to lift tissue upwardly relative to the upper deck, wherein the first distally-facing surface extends substantially obliquely relative to the upper deck and spans laterally at least partially across at least two longitudinal rows of the plurality of longitudinal rows of the plurality of pockets, and (ii) an upwardly-facing surface (D266, D366, D1066, D1166, D1366) that defines an uppermost surface of the stapling assembly.

Example 17

The stapling assembly of Example 16, wherein the first distally-facing surface of the first distalmost pocket extender is rounded in a longitudinal direction.

Example 18

The stapling assembly of any of Examples 16 through 17, wherein the first distally-facing surface of the first distalmost pocket extender is rounded in a lateral direction.

Example 19

The stapling assembly of any of Examples 16 through 18, wherein the plurality of longitudinal rows of the plurality of pockets includes at least three longitudinal rows of the plurality of pockets.

Example 20

The stapling assembly of Example 19, wherein the first distally-facing surface of the first distalmost pocket extender spans laterally at least partially across only first and second rows of the plurality of pockets such that the first distally-facing surface of the first distalmost pocket extender does not span laterally at least partially across a third row of the plurality of pockets.

Example 21

The stapling assembly of Example 20, wherein the first and second rows of the plurality of pockets include laterally inner and laterally middle rows of the plurality of pockets, respectively, wherein the third row of the plurality of pockets includes a laterally outer row of the plurality of pockets.

Example 22

The stapling assembly of any of Examples 20 through 21, wherein the plurality of pocket extenders includes a second distalmost pocket extender (D232, D332) having a second distally-facing surface (D254, D354) that is configured to lift tissue upwardly relative to the upper deck, wherein the second distally-facing surface extends substantially obliquely relative to the upper deck and is aligned with the third row of the plurality of pockets.

Example 23

The stapling assembly of Example 22, wherein the first distally-facing surface of the first distalmost pocket extender and the second distally-facing surface of the second distalmost pocket extender are configured to lift tissue upwardly relative to the upper deck substantially simultaneously with each other.

Example 24

The stapling assembly of any of Examples 22 through 23, wherein the second distally-facing surface of the second distalmost pocket extender is rounded in a longitudinal direction.

Example 25

The stapling assembly of any of Examples 22 through 24, wherein the second distally-facing surface of the second distalmost pocket extender is rounded in a lateral direction.

Example 26

The stapling assembly of any of Examples 16 through 25, wherein the first distally-facing surface of the first distalmost pocket extender extends upwardly and proximally relative to the upper deck to the upwardly-facing surface of the first distalmost pocket extender.

Example 27

The stapling assembly of any of Examples 16 through 26, wherein the upwardly-facing surface extends substantially parallel to the upper deck.

Example 28

The stapling assembly of any of Examples 16 through 27, wherein the upwardly-facing surface is configured to contact an adhesive portion (D116, D120, D166) of an adjunct (D110, D112, D160) for securing the adjunct to the stapling assembly.

Example 29

The stapling assembly of Example 28, wherein the upwardly-facing surface is shaped to substantially match a pattern of the adhesive portion of the adjunct.

Example 30

A surgical instrument (10), comprising: (a) the stapling assembly of any of Examples 16 through 29; and (b) an adjunct (D110, D112, D160) secured to the stapling assembly, wherein the adjunct includes: (i) an adjunct material portion (D114, D118, D164), and (ii) an adhesive portion (D116, D120, D166) contacting the upwardly-facing surface of the stapling assembly.

Example 31

A stapling assembly (D210, D310, D410, D510, D610, D710, D810, D910, D1010, D1110, D1310, D1510, D1610) for a surgical instrument (10), the stapling assembly comprising: (a) a body (D212, D312, D412, D512, D612, D712, D812, D912, D1012, D1112, D1312, D1512, D1612) extending along a longitudinal axis and having an upper deck (D214, D314, D414, D514, D614, D714, D814, D914, D1014, D1114, D1314, D1514, D1614), wherein the upper deck defines a stapling surface; (b) a plurality of pockets (D220, D320, D420, D520, D620, D720, D820, D920, D1020, D1120, D1320, D1520, D1620) extending through the upper deck for receiving respective staples (86), wherein the plurality of pockets are arranged in a plurality of longitudinal rows on each lateral side of the longitudinal axis; (c) a plurality of staple drivers (84), wherein each staple driver of the plurality of staple drivers is aligned with and movable vertically within a respective pocket of the plurality of pockets for actuating the respective staple into tissue (T1, T2); (d) a staple driver actuator (82) configured to translate distally relative to the body for lifting the plurality of staple drivers sequentially; (e) a plurality of pocket extenders (D230a, D230b, D232, D234, D330a, D330b, D332, D334, D430, D530, D630, D730, D830, D930, D1030a, D1030b, D1032, D1130a, D1130b, D1132, D1330a, D1330b, D1332, D1530, D1630) extending upwardly from the upper deck, wherein each pocket extender of the plurality of pocket extenders has a respective top surface (D246a, D246b, D256, D266, D346a, D346b, D356, D366, D446, D546, D646, D746, D846, D946, D1066, D1166, D1346a, D1346b) that defines an uppermost surface of the stapling assembly; and (f) a pair of distally-facing surfaces (D254, D264, D354, D364, D459, D659, D754, D854, D1064, D1164) that are each configured to lift tissue upwardly relative to the upper deck, wherein each distally-facing surface of the pair of distally-facing surfaces is disposed on a respective lateral side of the longitudinal axis, extends proximally and upwardly relative to a distal end of the upper deck toward the top surface of a distalmost pocket extender of the plurality of pocket extenders on the respective lateral side of the longitudinal axis, and spans laterally at least partially across at least two longitudinal rows of the plurality of pockets on the respective lateral side of the longitudinal axis.

Example 32

The stapling assembly of Example 31, wherein each distally-facing surface of the pair of distally-facing surfaces is rounded in a longitudinal direction.

Example 33

The stapling assembly of any of Examples 31 through 32, wherein each distally-facing surface of the pair of distally-facing surfaces is rounded in a lateral direction.

Example 34

The stapling assembly of any of Examples 31 through 33, wherein each distally-facing surface of the pair of distally-facing surfaces is tapered in a longitudinal direction.

Example 35

The stapling assembly of any of Examples 31 through 34, wherein each distally-facing surface of the pair of distally-facing surfaces spans laterally at least partially across at least three longitudinal rows of the plurality of pockets on the respective lateral side of the longitudinal axis.

Example 36

The stapling assembly of any of Examples 31 through 35, wherein each distally-facing surface of the pair of distally-facing surfaces extends upwardly and proximally relative to the upper deck to an upwardly-facing surface (D256, D266, D356, D366, D456, D656, D756, D856, D1066, D1166).

Example 37

The stapling assembly of Example 36, wherein the upwardly-facing surface extends substantially parallel to the upper deck.

Example 38

The stapling assembly of any of Examples 36 through 37, wherein the upwardly-facing surface is configured to contact an adhesive portion (D116, D120, D166) of an adjunct (D110, D112, D160) for securing the adjunct to the stapling assembly.

Example 39

The stapling assembly of Example 38, wherein the upwardly-facing surface is shaped to substantially match a pattern of the adhesive portion of the adjunct.

Example 40

A surgical instrument (10), comprising: (a) the stapling assembly of any of Examples 36 through 39; and (b) an adjunct (D110, D112, D160) secured to the stapling assembly, wherein the adjunct includes: (i) an adjunct material portion (D114, D118, D164), and (ii) an adhesive portion (D116, D120, D166) contacting the upwardly-facing surface of the stapling assembly.

Example 41

A stapling assembly (D210, D310, D410, D510, D610, D710, D810, D910, D1010, D1110, D1310, D1510, D1610) for a surgical instrument (10), the stapling assembly comprising: (a) a body (D212, D312, D412, D512, D612, D712, D812, D912, D1012, D1112, D1312, D1512, D1612) extending along a longitudinal axis and having an upper deck (D214, D314, D414, D514, D614, D714, D814, D914, D1014, D1114, D1314, D1514, D1614), wherein the upper deck defines a stapling surface; (b) a plurality of pockets (D220, D320, D420, D520, D620, D720, D820, D920, D1020, D1120, D1320, D1520, D1620) extending through the upper deck for receiving respective staples (86), wherein the plurality of pockets are arranged in a plurality of longitudinal rows; (c) a plurality of staple drivers (84), wherein each staple driver of the plurality of staple drivers is aligned with and movable vertically within a respective pocket of the plurality of pockets for actuating the respective staple into tissue (T1, T2); (d) a staple driver actuator (82) configured to translate distally relative to the body for lifting the plurality of staple drivers sequentially; (e) a plurality of first pocket extenders (D230a, D230b, D330a, D330b, D430, D530, D630, D730, D830, D930, D1030a, D1030b, D1130a, D1130b, D1330a, D1330b, D1530, D1630) extending upwardly from the upper deck, wherein each of the plurality of first pocket extenders includes a first top surface (D246a, D246b, D346a, D346b, D1046a, D1046b, D1146a, D1146b, D1346a, D1346b) positioned at a first height above the upper deck; and (f) at least one second pocket extender (D232, D234, D332, D334, D1032, D1132, D1332) extending upwardly from the upper deck and positioned distal of the plurality of first pocket extenders, wherein the at least one second pocket extender includes: (i) a second top surface (D256, D266, D356, D366, D1066, D1166, D1366) positioned at a second height above the upper deck, wherein the second height is different from the first height, (ii) a distally-facing surface (D264, D364, D1064, D1164, D1364) having a first profile such that the distally-facing surface is configured to apply a first frictional force to tissue, and (iii) a proximally-facing surface (D1163) having a second profile that is different from the first profile of the distally-facing surface such that the proximally-facing surface is configured to apply a second frictional force to tissue that is greater than the first frictional force provided by the distally-facing surface.

Example 42

The stapling assembly of Example 41, wherein the distally-facing surface extends substantially obliquely relative to the upper deck.

Example 43

The stapling assembly of any of Examples 41 through 42, wherein the proximally-facing surface extends substantially orthogonally relative to the upper deck.

Example 44

The stapling assembly of any of Examples 41 through 43, wherein the proximally-facing surface spans laterally at least partially across at least two longitudinal rows of the plurality of longitudinal rows of the plurality of pockets.

Example 45

The stapling assembly of Example 44, wherein the proximally-facing surface (D1163) spans laterally at least partially across three longitudinal rows of the plurality of longitudinal rows of the plurality of pockets.

Example 46

The stapling assembly of any of Examples 41 through 45, wherein the second height is greater than the first height.

Example 47

The stapling assembly of any of Examples 41 through 46, wherein the second top surface is configured to contact an anvil (44) prior to the first top surface contacting the anvil during approximation of the anvil (44) toward the stapling assembly.

Example 48

The stapling assembly of any of Examples 41 through 47, wherein at least one of the proximally-facing surface or the second top surface has a first surface finish, wherein the distally-facing surface has a second surface finish different from the first surface finish.

Example 49

The stapling assembly of Example 48, wherein the first surface finish is textured.

Example 50

The stapling assembly of any of Examples 47 through 49, wherein the second surface finish is smooth.

Example 51

A stapling assembly (D210, D310, D410, D510, D610, D710, D810, D910, D1010, D1110, D1310, D1510, D1610) for a surgical instrument (10), the stapling assembly comprising: (a) a body (D212, D312, D412, D512, D612, D712, D812, D912, D1012, D1112, D1312, D1512, D1612) extending along a longitudinal axis and having an upper deck (D214, D314, D414, D514, D614, D714, D814, D914, D1014, D1114, D1314, D1514, D1614), wherein the upper deck defines a stapling surface; (b) a plurality of pockets (D220, D320, D420, D520, D620, D720, D820, D920, D1020, D1120, D1320, D1520, D1620) extending through the upper deck for receiving respective staples (86), wherein the plurality of pockets are arranged in a plurality of longitudinal rows; (c) a plurality of staple drivers (84), wherein each staple driver of the plurality of staple drivers is aligned with and movable vertically within a respective pocket of the plurality of pockets for actuating the respective staple into tissue (T1, T2); (d) a staple driver actuator (82) configured to translate distally relative to the body for lifting the plurality of staple drivers sequentially; (e) a plurality of first pocket extenders (D230a, D230b, D330a, D330b, D430, D530, D630, D730, D830, D930, D1030a, D1030b, D1130a, D1130b, D1330a, D1330b, D1530, D1630) extending upwardly from the upper deck, wherein each of the plurality of first pocket extenders includes a first top surface (D246a, D246b, D346a, D346b, D1046a, D1046b, D1146a, D1146b, D1346a, D1346b); (f) at least one second pocket extender (D232, D234, D332, D334, D1032, D1132, D1332) extending upwardly from the upper deck and positioned distal of the plurality of first pocket extenders, wherein the at least one second pocket extender includes: (i) a second top surface (D256, D266, D356, D366, D1066, D1166, D1366), and (ii) a distally-facing surface (D264, D364, D1064, D1164, D1364), wherein the distally-facing surface extends substantially obliquely relative to the upper deck; (g) at least one longitudinal rail (D1370) extending upwardly from the upper deck and proximally from the at least one second pocket extender, wherein the at least one longitudinal rail includes a third top surface (D1372); and (h) at least one bridge (D1374) extending upwardly from the upper deck and laterally between at least one of: (i) a corresponding pair of the plurality of first pocket extenders, or (ii) the at least one longitudinal rail (D1370) and a corresponding one of the plurality of first pocket extenders, wherein the at least one bridge includes a fourth top surface (D1376).

Example 52

The stapling assembly of Example 51, wherein the at least one longitudinal rail includes a pair of longitudinal rails disposed on respective lateral sides of the longitudinal axis.

Example 53

The stapling assembly of any of Examples 51 through 52, wherein the first, second, third, and fourth top surfaces are each positioned at a same height above the upper deck.

Example 54

The stapling assembly of any of Examples 51 through 53, wherein the first, second, third, and fourth top surfaces are continuous with each other.

Example 55

The stapling assembly of any of Examples 51 through 54, wherein the plurality of first pocket extenders, the at least one second pocket extender, the at least one rail, and the at least one bridge collectively define a continuous lattice structure.

Example 56

A stapling assembly (D210, D310, D410, D510, D610, D710, D810, D910, D1010, D1110, D1310, D1510, D1610) for a surgical instrument (10), the stapling assembly comprising: (a) a body (D212, D312, D412, D512, D612, D712, D812, D912, D1012, D1112, D1312, D1512, D1612) extending along a longitudinal axis and having an upper deck (D214, D314, D414, D514, D614, D714, D814, D914, D1014, D1114, D1314, D1514, D1614), wherein the upper deck defines a stapling surface; (b) a plurality of pockets (D220, D320, D420, D520, D620, D720, D820, D920, D1020, D1120, D1320, D1520, D1620) extending through the upper deck for receiving respective staples (86), wherein the plurality of pockets are arranged in a plurality of longitudinal rows; (c) a plurality of staple drivers (84), wherein each staple driver of the plurality of staple drivers is aligned with and movable vertically within a respective pocket of the plurality of pockets for actuating the respective staple into tissue (T1, T2); and (d) a staple driver actuator (82) configured to translate distally relative to the body for lifting the plurality of staple drivers sequentially, wherein the upper deck tapers or curves downwardly in a laterally outward direction from a laterally inner peak (D1522, D1622) toward a laterally outer edge of the upper deck.

Example 57

The stapling assembly of Example 56, wherein the upper deck tapers downwardly in the laterally outward direction from the laterally inner peak toward the laterally outer edge of the upper deck.

Example 58

The stapling assembly of Example 56, wherein the upper deck curves downwardly in the laterally outward direction from the laterally inner peak toward the laterally outer edge of the upper deck.

Example 59

The stapling assembly of Example 58, wherein the upper deck includes a convex deck surface.

Example 60

The stapling assembly of any of Examples 56 through 59, wherein the upper deck tapers downwardly in a distal direction from the laterally inner peak toward a distal end of the upper deck.

The following clauses also relate to various non-exhaustive ways in which the teachings herein may be combined or applied.

1. A stapling assembly for a surgical instrument, the stapling assembly comprising:
   (a) a body extending along a longitudinal axis and having an upper deck, wherein the upper deck defines a stapling surface;
   (b) a plurality of pockets extending through the upper deck for receiving respective staples, wherein the plurality of pockets are arranged in at least two longitudinal rows;
   (c) a plurality of staple drivers, wherein each staple driver of the plurality of staple drivers is aligned with and movable vertically within a respective pocket of the plurality of pockets for actuating the respective staple into tissue;
   (d) a staple driver actuator configured to translate distally relative to the body for lifting the plurality of staple drivers sequentially;
   (e) a plurality of pocket extenders extending upwardly from the upper deck, wherein each pocket extender of the plurality of pocket extenders has a respective top surface that defines an uppermost surface of the stapling assembly; and
   (f) at least one upwardly-facing surface configured to contact an adhesive portion of an adjunct for securing the adjunct to the stapling assembly, wherein the at least one upwardly-facing surface is disposed at least partially between at least a portion of the upper deck and the top surfaces of the plurality of pocket extenders, wherein the at least one upwardly-facing surface spans laterally at least partially across the at least two longitudinal rows of the plurality of pockets.

2. The stapling assembly of Clause 1, wherein the at least one upwardly-facing surface has a greater surface area than each top surface of the plurality of pocket extenders.

3. The stapling assembly of Clause 1, wherein the plurality of pocket extenders includes a distalmost pocket extender, wherein the at least one upwardly-facing surface extends further distally than the top surface of the distalmost pocket extender.

4. The stapling assembly of Clause 1, wherein the plurality of pocket extenders includes a proximal-most pocket extender, wherein the at least one upwardly-facing surface extends further proximally than the top surface of the proximal-most pocket extender.

5. The stapling assembly of Clause 1, wherein the at least one upwardly-facing surface extends substantially parallel to the upper deck.

6. The stapling assembly of Clause 1, wherein the at least one upwardly-facing surface extends substantially obliquely to the upper deck.

7. The stapling assembly of Clause 6, wherein the at least one upwardly-facing surface includes at least one upwardly and proximally-facing surface that extends upwardly and distally from the upper deck to a peak.

8. The stapling assembly of Clause 6, wherein the at least one upwardly-facing surface includes at least one upwardly and distally-facing surface that extends upwardly and proximally from the upper deck to a peak.

9. The stapling assembly of Clause 8, wherein the peak of the at least one upwardly and distally-facing surface coincides with the peak of a corresponding upwardly and proximally-facing surface.

10. The stapling assembly of Clause 8, further comprising at least one proximally-facing surface that extends substantially orthogonally relative to the upper deck from the upper deck to the peak of the at least one upwardly and distally-facing surface.

11. The stapling assembly of Clause 1, wherein the at least one upwardly-facing surface includes at least one hemispherical surface.

12. The stapling assembly of Clause 1, wherein the at least one upwardly-facing surface is shaped to substantially match a pattern of the adhesive portion of the adjunct.

13. The stapling assembly of Clause 1, further comprising at least one opening extending through the at least one upwardly-facing surface and overlying a corresponding pocket of the plurality of pockets for accommodating passage of the respective staple therethrough.

14. The stapling assembly of Clause 1, further comprising at least one atraumatic, distally-facing surface extending downwardly and distally from the at least one upwardly-facing surface and configured to lift tissue upwardly relative to the upper deck.

15. A surgical instrument, comprising:
   (a) the stapling assembly of Clause 1; and
   (b) an adjunct secured to the stapling assembly, wherein the adjunct includes:
      (i) an adjunct material portion, and
      (ii) an adhesive portion contacting the at least one upwardly-facing surface of the stapling assembly.

16. A stapling assembly for a surgical instrument, the stapling assembly comprising:
   (a) a body extending along a longitudinal axis and having an upper deck, wherein the upper deck defines a stapling surface;
   (b) a plurality of pockets extending through the upper deck for receiving respective staples, wherein the plurality of pockets are arranged in a plurality of longitudinal rows;
   (c) a plurality of staple drivers, wherein each staple driver of the plurality of staple drivers is aligned with and movable vertically within a respective pocket of the plurality of pockets for actuating the respective staple into tissue;
   (d) a staple driver actuator configured to translate distally relative to the body for lifting the plurality of staple drivers sequentially; and
   (e) a plurality of pocket extenders extending upwardly from the upper deck, wherein the plurality of pocket extenders includes a first distalmost pocket extender having:
      (i) a first distally-facing surface that is configured to lift tissue upwardly relative to the upper deck, wherein the first distally-facing surface extends substantially obliquely relative to the upper deck and spans laterally at least partially across at least two longitudinal rows of the plurality of longitudinal rows of the plurality of pockets, and
      (ii) an upwardly-facing surface that defines an uppermost surface of the stapling assembly.

17. The stapling assembly of Clause 16, wherein the first distally-facing surface of the first distalmost pocket extender is rounded in a longitudinal direction.

18. The stapling assembly of Clause 16, wherein the first distally-facing surface of the first distalmost pocket extender is rounded in a lateral direction.

19. The stapling assembly of Clause 16, wherein the plurality of longitudinal rows of the plurality of pockets includes at least three longitudinal rows of the plurality of pockets.

20. A stapling assembly for a surgical instrument, the stapling assembly comprising:
   (a) a body extending along a longitudinal axis and having an upper deck, wherein the upper deck defines a stapling surface;
   (b) a plurality of pockets extending through the upper deck for receiving respective staples, wherein the plurality of pockets are arranged in a plurality of longitudinal rows on each lateral side of the longitudinal axis;
   (c) a plurality of staple drivers, wherein each staple driver of the plurality of staple drivers is aligned with and movable vertically within a respective pocket of the plurality of pockets for actuating the respective staple into tissue;
   (d) a staple driver actuator configured to translate distally relative to the body for lifting the plurality of staple drivers sequentially;
   (e) a plurality of pocket extenders extending upwardly from the upper deck, wherein each pocket extender of the plurality of pocket extenders has a respective top surface that defines an uppermost surface of the stapling assembly; and
   (f) a pair of distally-facing surfaces that are each configured to lift tissue upwardly relative to the upper deck, wherein each distally-facing surface of the pair of distally-facing surfaces is disposed on a respective lateral side of the longitudinal axis, extends proximally and upwardly relative to a distal end of the upper deck toward the top surface of a distalmost pocket extender of the plurality of pocket extenders on the respective lateral side of the longitudinal axis, and spans laterally at least partially across at least two longitudinal rows of the plurality of pockets on the respective lateral side of the longitudinal axis.

IX. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application No. 18/588,147, filed Feb. 27, 2024, entitled "Surgical Stapler Cartridge Having Intermediate Raised Tissue Engagement Protrusions," published as U.S. Pat. Pub. No. 2024/0382197 on Nov. 21, 2024, filed on Feb. 27, 2024; U.S. patent application No. 18/588,175, filed Feb. 27, 2024, entitled "Surgical Stapler Cartridge Having Tissue Engagement Protrusions with Enlarged Engagement Surface," published as U.S. Pat. Pub. No. 2024/0382196 on Nov. 21, 2024, filed on Feb. 27, 2024; U.S. patent application No. 18/588,240, filed Feb. 27, 2024, entitled "Surgical Stapler Cartridge Having Cartridge Retention Features," published as U.S. Pat. Pub. No. 2024/0382203 on Nov. 21, 2024, filed on Feb. 27, 2024; U.S. patent application No. 18/588,269, filed Feb. 27, 2024, entitled "Surgical Stapler Anvil Having Staple Forming Pockets with Laterally Varying Orientations," published as U.S. Pat. Pub. No. 2024/0341761 on Oct. 17, 2024, filed on Feb. 27, 2024; U.S. patent application No. 18/588,684, filed Nov. 27, 2024, entitled "Method of Surgical Stapling," published as U.S. Pat. Pub. No. 2024/03510137 on Oct. 24, 2024, filed on Feb. 27, 2024; and/or U.S. patent application No. 18/588,094, filed Feb. 27, 2024, entitled "Incompatible Staple Cartridge Use Prevention Features for Surgical Stapler," published as U.S. Pat. Pub. No. 2024/0382201 on Nov. 21, 2024, filed on Feb. 27, 2024. The disclosure of each of these U.S. patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A stapling assembly for a surgical instrument, the stapling assembly comprising:
    (a) a body extending along a longitudinal axis and having an upper deck, wherein the upper deck defines a stapling surface;
    (b) a plurality of pockets extending through the upper deck for receiving respective staples, wherein the plurality of pockets are arranged in at least two longitudinal rows;
    (c) a plurality of staple drivers, wherein each staple driver of the plurality of staple drivers is aligned with and movable vertically within a respective pocket of the plurality of pockets for actuating the respective staple into tissue;
    (d) a staple driver actuator configured to translate distally relative to the body for lifting the plurality of staple drivers sequentially;
    (e) a plurality of pocket extenders extending upwardly from the upper deck, wherein each pocket extender of the plurality of pocket extenders has a respective top surface that defines an uppermost surface of the stapling assembly; and
    (f) at least one upwardly-facing surface configured to contact an adhesive portion of an adjunct for securing the adjunct to the stapling assembly, wherein the at least one upwardly-facing surface is disposed at least partially between at least a portion of the upper deck and the top surfaces of the plurality of pocket extenders, wherein the at least one upwardly-facing surface spans laterally at least partially across the at least two longitudinal rows of the plurality of pockets.

2. The stapling assembly of claim 1, wherein the at least one upwardly-facing surface has a greater surface area than each top surface of the plurality of pocket extenders.

3. The stapling assembly of claim 1, wherein the plurality of pocket extenders includes a distalmost pocket extender, wherein the at least one upwardly-facing surface extends further distally than the top surface of the distalmost pocket extender.

4. The stapling assembly of claim 1, wherein the plurality of pocket extenders includes a proximal-most pocket extender, wherein the at least one upwardly-facing surface extends further proximally than the top surface of the proximal-most pocket extender.

5. The stapling assembly of claim 1, wherein the at least one upwardly-facing surface extends substantially parallel to the upper deck.

6. The stapling assembly of claim 1, wherein the at least one upwardly-facing surface extends substantially obliquely to the upper deck.

7. The stapling assembly of claim 6, wherein the at least one upwardly-facing surface includes at least one upwardly and proximally-facing surface that extends upwardly and distally from the upper deck to a peak.

8. The stapling assembly of claim 6, wherein the at least one upwardly-facing surface includes at least one upwardly and distally-facing surface that extends upwardly and proximally from the upper deck to a peak.

9. The stapling assembly of claim 8, wherein the peak of the at least one upwardly and distally-facing surface coincides with the peak of a corresponding upwardly and proximally-facing surface.

10. The stapling assembly of claim 8, further comprising at least one proximally-facing surface that extends substantially orthogonally relative to the upper deck from the upper deck to the peak of the at least one upwardly and distally-facing surface.

11. The stapling assembly of claim 1, wherein the at least one upwardly-facing surface includes at least one hemispherical surface.

12. The stapling assembly of claim 1, wherein the at least one upwardly-facing surface is shaped to substantially match a pattern of the adhesive portion of the adjunct.

13. The stapling assembly of claim 1, further comprising at least one opening extending through the at least one upwardly-facing surface and overlying a corresponding pocket of the plurality of pockets for accommodating passage of the respective staple therethrough.

14. The stapling assembly of claim 1, further comprising at least one atraumatic, distally-facing surface extending downwardly and distally from the at least one upwardly-facing surface and configured to lift tissue upwardly relative to the upper deck.

15. A surgical instrument, comprising:
(a) the stapling assembly of claim 1; and
(b) an adjunct secured to the stapling assembly, wherein the adjunct includes:
(i) an adjunct material portion, and
(ii) an adhesive portion contacting the at least one upwardly-facing surface of the stapling assembly.

16. A stapling assembly for a surgical instrument, the stapling assembly comprising:
(a) a body extending along a longitudinal axis and having an upper deck, wherein the upper deck defines a stapling surface;
(b) a plurality of pockets extending through the upper deck for receiving respective staples, wherein the plurality of pockets are arranged in a plurality of longitudinal rows;
(c) a plurality of staple drivers, wherein each staple driver of the plurality of staple drivers is aligned with and movable vertically within a respective pocket of the plurality of pockets for actuating the respective staple into tissue;
(d) a staple driver actuator configured to translate distally relative to the body for lifting the plurality of staple drivers sequentially; and
(e) a plurality of pocket extenders extending upwardly from the upper deck, wherein the plurality of pocket extenders includes a first distalmost pocket extender having:
(i) a first distally-facing surface that is configured to lift tissue upwardly relative to the upper deck, wherein the first distally-facing surface extends substantially obliquely relative to the upper deck and spans laterally at least partially across at least two longitudinal rows of the plurality of longitudinal rows of the plurality of pockets, and
(ii) an upwardly-facing surface that defines an uppermost surface of the stapling assembly.

17. The stapling assembly of claim 16, wherein the first distally-facing surface of the first distalmost pocket extender is rounded in a longitudinal direction.

18. The stapling assembly of claim 16, wherein the first distally-facing surface of the first distalmost pocket extender is rounded in a lateral direction.

19. The stapling assembly of claim 16, wherein the plurality of longitudinal rows of the plurality of pockets includes at least three longitudinal rows of the plurality of pockets.

20. A stapling assembly for a surgical instrument, the stapling assembly comprising:
(a) a body extending along a longitudinal axis and having an upper deck, wherein the upper deck defines a stapling surface;
(b) a plurality of pockets extending through the upper deck for receiving respective staples, wherein the plurality of pockets are arranged in a plurality of longitudinal rows on each lateral side of the longitudinal axis;
(c) a plurality of staple drivers, wherein each staple driver of the plurality of staple drivers is aligned with and movable vertically within a respective pocket of the plurality of pockets for actuating the respective staple into tissue;
(d) a staple driver actuator configured to translate distally relative to the body for lifting the plurality of staple drivers sequentially;
(e) a plurality of pocket extenders extending upwardly from the upper deck, wherein each pocket extender of the plurality of pocket extenders has a respective top surface that defines an uppermost surface of the stapling assembly; and
(f) a pair of distally-facing surfaces that are each configured to lift tissue upwardly relative to the upper deck, wherein each distally-facing surface of the pair of distally-facing surfaces is disposed on a respective lateral side of the longitudinal axis, extends proximally and upwardly relative to a distal end of the upper deck toward the top surface of a distalmost pocket extender of the plurality of pocket extenders on the respective lateral side of the longitudinal axis, and spans laterally at least partially across at least two longitudinal rows of the plurality of pockets on the respective lateral side of the longitudinal axis.

* * * * *